US007109319B2

(12) United States Patent
Fraser

(10) Patent No.: US 7,109,319 B2
(45) Date of Patent: Sep. 19, 2006

(54) FAIL MOLECULES AND USES THEREOF

(75) Inventor: Christopher C. Fraser, Lexington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 10/384,850

(22) Filed: Mar. 10, 2003

(65) Prior Publication Data

US 2003/0175890 A1 Sep. 18, 2003

Related U.S. Application Data

(63) Continuation of application No. 09/702,021, filed on Oct. 30, 2000, now abandoned.

(51) Int. Cl.
 C12N 15/12 (2006.01)
 C12N 15/63 (2006.01)
 C12P 21/00 (2006.01)
(52) U.S. Cl. ............... 536/23.5; 435/69.1; 435/320.1; 435/252.3; 435/254.2
(58) Field of Classification Search ............ 435/69.1, 435/325; 530/300, 350
 See application file for complete search history.

(56) References Cited

U.S. PATENT DOCUMENTS

| 5,198,342 | A | * | 3/1993 | Maliszewski ............ 435/69.1 |
| 5,328,987 | A | * | 7/1994 | Maliszewski ............ 530/350 |
| 5,506,126 | A | | 4/1996 | Seed et al. |
| 5,985,599 | A | * | 11/1999 | McKenzie et al. ........ 435/69.1 |
| 6,287,820 | B1 | * | 9/2001 | Umansky et al. .......... 435/91.1 |
| 2004/0034192 | A1 | | 2/2004 | Kato et al. |

FOREIGN PATENT DOCUMENTS

| WO | WO 99/40117 A1 | | 8/1999 |
| WO | WO 99/46281 A2 | | 9/1999 |
| WO | WO 00/28032 | * | 5/2000 |
| WO | WO 00/28032 A2 | | 5/2000 |
| WO | WO 00/32767 A1 | | 6/2000 |
| WO | WO 01/49728 | * | 7/2001 |
| WO | WO 01/49728 A2 | | 7/2001 |

OTHER PUBLICATIONS

Skolnick and Fetrow (2000) From Genes to Protein Structure and Function: Novel Applications of Compuational Approaches the Genomic Era. Trends in Biotech 18(1); 34-39.*
Wells, J.A. Additivity of Mutational Effects of Proteins (1990) Biochemistry 29(37): 8509-8517.*
Davis et al. (2002) Identification of a family of Fc Receptor homologs with referential B cell expression. PNAS 98(17): 9772-9777.*
Bork (2000) Powers and Pitfalls in Sequence Analysis: The 70% Hurdle. Genome Research 10: 398-400.*
Doerks (1998) Protein Annotation: detective work for function prediction. TIG 14(6): 248-250.*
Smith and Zhang (1997) The Challenges of genome sequence annotation or "The Devil is in the details". Nature Biotechnology 15: 1222-1223.*
Brenner (1999) Erros in genome annotation TIG 15(4): 132-133.*
Bork and Bairoch (1996) Go Hunting in sequence databases but watch out for the traps. TIG 12(10): 425-427.*
Bendayan (1995) Possibilities of False Immunocytochemical Results Generated by the Use of Monoclonal Antibodies: The Example of the Anti-proinsulin Antibody. The Journal of Histochemistry and Cytochemistry 43(9): 881-886.*
Seaman et al. (1991) Molecular Cloning of gp42, A cell-sruface molecule that is selectively induced on rat natural kill cell by interluekin 2: Glycolipid membrane anchoring and capacity for transmembrane signaling. J. Exp. Med. 251-260.*
Mechetina et al. (Jan. 2002) "FCRL, a novel member of the leukocyte Fc receptor family possesses unique structural features." European Journal of Immunology 32(1): 87-96.*
Neto et al. (Mar. 28, 2000) "Shotgun sequencing of the human transcriptome with ORF expressed sequence tags." PNAS 97(7): 3491-3496.*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*
Bieber et al. (Oct. 1996) "New insights in the structure and biology of the high affinity receptor for lgE (FceRl) on human epidermal Langerhans cells." J Dermatol Sci. 13(1): 71-75.*
Capel et al. (Feb. 1994) "Heterogeneity of human lgG Fc Receptors." Immunomethods 4(1): 25-34.*
"Nucleic Acid Hybridization- General Aspects" pp. 33-37 Roche website retrieved on May 12, 2004.*
NIH Division of Intramural Research "Nucleic Acid Hybridization" retrieved from NIH website on May 12,2004.*
Marshall "Gene Therapy's Growing Pains". Science, vol. 269 (1995), pp. 1050-1055.*
Verma I.M. et al. 1997. Nature 389:239-242.*
Orkin S.H. et al. 1995. "Report and Recommendations of the Panel to Assess the NIH Investment in Research on Gene Therapy".*
Hopp et al., Proc Natl Acad Sci USA 78:3824-2828.*
Stratagene Catalog, 1991, p. 66.*
Wiesmann 2000. J. Mol. Med 78:247-260.*

(Continued)

Primary Examiner—Sharon Turner
Assistant Examiner—Daniel E. Kolker
(74) Attorney, Agent, or Firm—Millennium Pharmaceuticals, Inc.

(57) ABSTRACT

The invention provides isolated nucleic acid molecules, designated FAIL, which encode polypeptide molecules containing Ig and Ig-like domains and which are homologous to FcγRI. The invention also provides antisense nucleic acid molecules, expression vectors containing the nucleic acid molecules of the invention, host cells into which the expression vectors have been introduced, and non-human transgenic animals in which a nucleic acid molecule of the invention has been introduced or disrupted. The invention still further provides isolated polypeptides, fusion polypeptides, antigenic peptides and antibodies. Diagnostic, screening and therapeutic methods utilizing compositions of the invention are also provided.

20 Claims, 13 Drawing Sheets

OTHER PUBLICATIONS

Van de Winkel, J.F.J. et al. "IgG Fc receptor 1" Apr. 27, 1993 (sequence) GenBank [online] Bethesda, MD, USA: National Center for Biotechnology Information [retrieved on Apr. 9, 2001]. GenBank Accession No. AAA35678.

"FC gamma Rlla [Homo sapiens]" Jul. 21, 1994 (sequence) GenBank [online] Bethesda, MD, USA: National Center for Biotechnology Information [retrieved on Apr. 9, 2001]. GenBank Accession No. CAA01563.

Kochan, J., et al. "High Affinity Immunoglobulin Epsilon Receptor Alpha-Subunit Precursor (FCERI) (IGE FC Receptor, Alpha-Subunit) (FC-Epsilon Rl-Alpha)" Oct. 1, 2000 (sequence) GenBank [online] Bethesda, MD, USA: National Center for Biotechnology Information [retrieved on Apr. 9, 2001]. GenBank Accession No. P12319.

Ng, S. et al. "Low Affinity Immunoglobulin Gamma FC Region Receptor II-B Precursor (FC-Gamma RII-B) (FCRII-B) (IGG FC receptor II-B) (FC Gamma-RIIB) (CD32) (CDW32)". May 30, 2000 (sequence) GenBank [online] Bethesda, MD, USA: National Center for Biotechnology Information [retrieved on Apr. 9, 2001]. GenBenk Accession No. P31994.

Stuart S.G., et al. "Low Affinity Immunoglobulin Gamma FC Region Receptor II-C Precursor (FC-Gamma RII-C) (FCRII-C) (IGG FC Receptor II-C) (FC-GAMMARIIC) (CD32) (CDW32)". Oct. 1, 2000 (sequence) GenBank [online] Bethesda, MD, USA: National Center for Biotechnology Information [retrieved on Apr. 9, 2001]. GenBank Accession No. P31995.

Ravetch, J.V. and Perussia, B. "Low Affinity Immunoglobulin Gamma FC Region Receptor III-A Precursor (IGG FC Receptor III-2_ (FC-Gamma RIII-Alpha) (FC-Gamma RIIIA) (FCRIIIA) (FC-GAMMA RIII) (FCRIII) (CD16-A) (FCR-10)" May 30, 2000 (sequence) GenBank [online] Bethesda, MD, USA: National Center for Biotechnology Information [retrieved on Apr. 9, 2001]. GenBank Accession No. P08637.

Allen, J.M. and Seed, B. "Human mRNA for High Affinity Fc Receptor (FcRI) 'b form'" Sep. 12, 1993 (sequence) GenBank [online] Bethesda, MD, USA: National Center for Biotechnology Information [retrieved on Apr. 9, 2001]. GenBank Accession No. X14355.

Bateman, A. et al. "Immunoglobulin Domain" (database result) Pfam [online] St. Louis, MO, USA, Washington University School of Medicine [retrieved Apr. 9, 2001]. Accession No. PF00047.

Altschul, Stephen F. et al., "Gapped BLAST and PSI-BLAST: A New Generation of Protein Database Search Programs" *Nucleic Acids Research* vol. 25, No. 17 (Sep. 1, 1997), pp. 3389-3402.

Atschul, Stephen F. et al., "Basic Local Alignment Search Tool" *Journal of Molecular Biology* vol. 215 (Oct. 5, 1990), pp. 403-410.

Barnes, Peter J. "Therapeutic Strategies for Allergic Diseases" *Nature* vol. 402 (supp) (Nov. 25, 1999) pp. B31-B38.

Buck, Clayton A., "Immunoglobulin Superfamily: Structure, Function and Relationship to other Receptor Molecules" *Seminars in Cell Biology* vol. 3 (Jun. 1992) pp. 179-188.

Corry, David B. and Kheradmand, F. "Induction and Regulation of the IgE Response" *Nature* vol. 402 (supp) (Nov. 25, 1999) pp. B18-B23.

Daëron, Marc, "Fc Receptor Biology" *Annual Review Immunology* vol. 15 (1997) pp. 203-234.

Emara, Mohamed and Sanfilippo, F. "The Inhibition of T Cell Proliferative Responses by Crosslinking CD7 and IgM-Fc Receptors" *Cellular Immunology* vol. 144 (Oct. 1, 1992) pp. 143-154.

Emara, Mohamed and Carroll, R.G., "Signal Transduction Through Crosslinking CD7 and IgM-Fc Receptors that Inhibits T-Cell Proliferation" *Human Immunology* vol. 34 (Jul. 1992) pp. 181-195.

Heyman, Birgitta, "Regulation of Antibody Responses Via Antibodies, complement, and Fc Receptors" *Annual Review Immunology* vol. 18 (2000) pp. 709-737.

Holgate, Stephen T. "The Epidemic of Allergy and Asthma" *Nature* vol. 402 (supp) ( Nov. 25, 1999) pp. B2-B4.

Karlin, Samuel and Altschul, S.F., "Applications and Statistics for Multiple High-Scoring Seqments in Molecular Sequences" *Proceedings of the National Academy of Sciences of the United States of America* vol. 90 (Jun. 1993) pp. 5873-5877.

Karlin, Samuel and Altschul, S.F., "Methods for Assessing the Statistical Significance of Molecular Sequence Features by Using General Scoring Schemes" *Proceedings of the National Academy of Sciences of the United States of America* vol. 87 (Mar. 1990) pp. 2264-2268.

Kleinau, Sandra et al., "Induction and Suppression of Collagen-induced Arthritis is Dependent on Distinct Fcγ Receptors" *The Journal of Experimental Medicine* vol. 191, No. 9, (May 1, 2000) pp. 1611-1616.

Mathur, Ambika et al. "The Contribution of Constant Region Domains to the Binding of Murine IgM to Fcμ Receptors on T Cells[1]" *The Journal of Immunology* vol. 140, No. 1 (Jan, 1, 1988) pp. 143-147.

Metzger, Henry "It's Spring, and Thoughts Turn to . . . Allergies" *Cell* vol. 97 (Apr. 30, 1999) pp. 287-290.

Myers, Eugene and Miller, W., "Optimal Alignments in Linear Space" *Computer Applications in the Biosciences* vol. 4, No. 1 (1988) pp. 11-17.

Nakamura, Tetsuya et al. "Characterization of an IgM Fc-Binding Receptor on Human T Cells" *The Journal of Immunology* vol. 151, No. 12 (Dec. 15, 1993) pp. 6933-6941.

Ohno, Tatsuharu et al. "Biochemical Nature of an Fcμ Receptor on Human B-Lineage Cells" *The Journal of Experimental Medicine* vol. 172 (Oct. 1990) pp. 1165-1175.

Pearson, William R. and Lipman, D.I., "Improved Tools for Biological Sequence Comparison" *Proceedings of the National Academy of Sciences of the United States of America* vol. 85 (Apr. 1988) pp. 2444-2448.

Pricop, Luminita, et al. "Characterization of the Fcμ Receptor on Human Natural Killer Cells" *The Journal of Immunology* vol. 151, No. 6 (Sep. 15, 1993) pp. 3018-3029.

Rabinowich, Hannah et al. "Physical and Functional Association of Fcμ Receptor on Human Natural Killer Cells with the ζ- and Fc∈RI γ-Chains and the *src* Family Protein Tyrosine Kinases" *The Journal of Immunology* vol. 157 (1996) pp. 1485-1491.

Ravetch, Jeffrey V. and Clynes, R.A., "Divergent Roles for Fc Receptors and Complement in Vivo" *Annual Review of Immunology* vol. 16 (1998) pp. 421-432.

Torelli, Alberto and Robotti, C.A., "ADVANCE and ADAM: Two Algorithms for the Analysis of Global Similarity Between Homologous Informational Sequences" *Computer Applications in the Biosciences* vol. 10, No. 1 (1994) pp. 3-5.

Turner, Helen and Kinet, Jean-Pierre., "Signalling Through the High-Affinity IgE Receptor Fc∈RI" *Nature* vol. 402 (supp) (Nov. 25, 1999) pp. B24-B30.

Strausberg, Robert "tz82g10.×1 NCI_CGAP_Pan1 Homo sapiens cDNA clone IMAGE:2295138 3' similar to contains MER29.b2 MER29 repetitive element; mRNA sequence" Apr. 27, 1999 (sequence) srs@EMBL-EBI [online]. Hinxton, Cambridge, UK: European Bioinformatics Institute. EMBL Accession No. A1631310.

Strausberg, Robert "wc88a09.×1 NCI_CGAP_Co3 Homo sapiens cDNA clone IMAGE: 2325688 3' similar to contains MER29.b2 MER29 repetitive element; mRNA sequence" May 27, 1999 (sequence) srs@EMBL-EBI [online]. Hinxton, Cambridge, UK: European Bioinformatics Institute. EMBL Accession No. AI677739.

Seaman, William E. et al. "Molecular Cloning of gp42 , A Cell-Surface Molecule that is Selectively Induced on Rat Natural Killer Cells by Interleukin 2: Glycolipid Membrane Anchoring and Capacity for Transmembrane Signaling" *The Journal of Experimental Medicine* vol. 173 (Jan. 1991) pp. 251-260.

Mechetina, Ludmila V. et al., "FCRL, A Novel Member of the Leukocyte Fc Receptor Family Possesses Unique Structural Features" *European Journal of Immunology*, vol. 32, (2002), pp. 87-96.

Patel, Ashok M., et al., "Hypersensitivity Pneumonitis: Currect Concepts and Future Questions" *Journal of Allergy and Clinical Immunology*, vol. 108, No. 5 (Nov. 2001), pp. 661-670.

Neumann, Harald et al. "Cytotoxic T Lymphocytes in Autoimmune and Degenerative CNS Diseases" *Trends in Neurosciences*, vol. 25, No. 6 (Jun. 2002) pp. 313-319.

Liblau, Roland S. et al. "Autoreactive CD8 T Cells in Organ-Specific Autoimmunity: Emerging Targets for Therapeutic Intervention" *Immunity*, vol. 17 (Jul. 2002) pp. 1-6.

Hillier, L., et al., "zw67f05.r1 Soares_testis_NHT Homo sapiens cDNA clone IMAGE:781281 5' similar to SW:FCGA_HUMAN P12318 Low Affinity Immunoglobulin Gamma FC Receptor II-A Precursor;, MRNA sequence" Jun. 3, 1997 (sequence) GenBank [online] Bethesda, MD, USA: National Center for Biotechnology Information [retrieved on Mar. 3, 2005]. Retrieved from the Internet : URL: http://www.ncbi.nlm.gov/>. GenBank Accession No. AA446524.

* cited by examiner

```
Input file FA.seq; Output File FA.pat
Sequence length 1872
                                                                          M   L   P     3
GTCGACCCACGCGTCCGCAACTCAGGAGATCTGTTGGAAAGAGAACGATAGAGGAAAATATATGA ATG TTG CCA    74

S   L   V   P   C   V   G   K   T   V   W   L   Y   L   Q   A   W   P   N   P    23
TCT TTA GTT CCC TGT GTT GGG AAA ACT GTC TGG CTG TAC CTC CAA GCC TGG CCA AAC CCT   134

V   F   E   G   D   A   L   T   L   R   C   Q   G   W   K   N   T   P   L   S    43
GTG TTT GAA GGA GAT GCC CTG ACT CTG CGA TGT CAG GGA TGG AAG AAT ACA CCA CTG TCT   194

Q   V   K   F   Y   R   D   G   K   F   L   H   F   S   K   E   N   Q   T   L    63
CAG GTG AAG TTC TAC AGA GAT GGA AAA TTC CTT CAT TTC TCT AAG GAA AAC CAG ACT CTG   254

S   M   G   A   A   T   V   Q   S   R   G   Q   Y   S   C   S   G   Q   V   M    83
TCC ATG GGA GCA GCA ACA GTG CAG AGC CGT GGC CAG TAC AGC TGC TCT GGG CAG GTG ATG   314

Y   I   P   Q   T   F   T   Q   T   S   E   T   A   M   V   Q   V   Q   E   L   103
TAT ATT CCA CAG ACA TTC ACA CAA ACT TCA GAG ACT GCC ATG GTT CAA GTC CAA GAG CTG   374

F   P   P   P   V   L   S   A   I   P   S   P   E   P   R   E   G   S   L   V   123
TTT CCA CCT CCT GTG CTG AGT GCC ATC CCC TCT CCT GAG CCC CGA GAG GGT AGC CTG GTG   434

T   L   R   C   Q   T   K   L   H   P   L   R   S   A   L   R   L   L   F   S   143
ACC CTG AGA TGT CAG ACA AAG CTG CAC CCC CTG AGG TCA GCC TTG AGG CTC CTT TTC TCC   494

F   H   K   D   G   H   T   L   Q   D   R   G   P   H   P   E   L   C   I   P   163
TTC CAC AAG GAC GGC CAC ACC TTG CAG GAC AGG GGC CCT CAC CCA GAA CTC TGC ATC CCG   554

G   A   K   E   G   D   S   G   L   Y   W   C   E   V   A   P   E   G   G   Q   183
GGA GCC AAG GAG GGA GAC TCT GGG CTT TAC TGG TGT GAG GTG GCC CCT GAG GGT GGC CAG   614

V   Q   K   Q   S   P   Q   L   E   V   R   V   Q   A   P   V   S   R   P   V   203
GTC CAG AAG CAG AGC CCC CAG CTG GAG GTC AGA GTG CAG GCT CCT GTA TCC CGT CCT GTG   674

L   T   L   H   H   G   P   A   D   P   A   V   G   D   M   V   Q   L   L   C   223
CTC ACT CTG CAC CAC GGG CCT GCT GAC CCT GCT GTG GGG GAC ATG GTG CAG CTC CTC TGT   734

E   A   Q   R   G   S   P   P   I   L   Y   S   F   Y   L   D   E   K   I   V   243
GAG GCA CAG AGG GGC TCC CCT CCG ATC CTG TAT TCC TTC TAC CTT GAT GAG AAG ATT GTG   794

G   N   H   S   A   P   C   G   G   T   T   S   L   L   F   P   "   K   S   E   263
GGG AAC CAC TCA GCT CCC TGT GGT GGA ACC ACC TCC CTC CTC TTC CCA GT  AAG TCA GAA   854

Q   D   A   G   N   Y   S   C   E   A   E   N   S   V   S   R   L   R   S   E   283
CAG GAT GCT GGG AAC TAC TCC TGC GAG GCT GAG AAC AGT GTC TCC AGA GAG AGG AGT GAG   914

P   K   K   L   S   L   K   G   S   Q   V   L   F   T   P   A   S   N   W   L   303
CCC AAG AAG CTG TCT CTG AAG GGT TCT CAA GTC TTG TTC ACT CCC GCC AGC AAC TGG CTG   974

V   P   W   L   P   A   S   L   L   G   L   M   V   I   A   A   A   L   L   V   323
GTT CCT TGG CTT CCT GCG AGC CTG CTT GGC CTG ATG GTT ATT GCT GCT GCA CTT CTG GTT  1034
```

FIG.1A

```
  Y   V   R   S   W   R   K   A   V   H   H   Q   K   G   K   D   E   G   V   V     343
TAT GTG AGA TCC TGG AGA AAA GCT GTG CAT CAC CAG AAA GGG AAA GAT GAA GGT GTT GTC    1094

Y   S   V   V   H   R   T   S   K   R   S   E   G   Q   F   Y   H   L   C   G     363
TAC TCT GTG GTG CAT AGA ACC TCA AAG AGG AGT GAA GGA CAG TTC TAT CAT CTG TGC GGA    1154

G   E   M   P   A   A   Q   *                                                      371
GGT GAG ATG CCT GCA GCC CAG TGA                                                     1178
```

GGTTTCATCCACGGAGGTGAATATGAGAAGCAGGACTCTCCAAGAACCCCTTAGCGACTGTGAGGAGGTTCTCTGCTAG 1257

TGATGGTGTTCTCCTATCAACACACGCCCACCCCCAGTCTCCAGTGCTCCTCAGGAAGACAGTGGGGTCCTCAACTCTT 1336

TCTGTGGGTCCTTCAGTTCCCAAGCCCAGCATCACAGAGCCCCCTGAGCCCTTGTCCTGGTCAGGAGCACCTGAACCCT 1415

GGGTTCTTTTCTTAGCAGAAGACCAACCAATGGAATGGGAAGGGAGATGCTCCCACCAACACACACACTTAGGTTCAAT 1494

CAGTGACACTGGACACATAAGCCACAGATGTCTTCTTTCGATACAAGCATGTTAGTTCGCCCCAATATACATATATATA 1573

TGAAATAGTCATGTGCCGCATAACAACATTTCAGTCAGTGATAGACTGCATACACAACAGTGGTCCCATAAGACTGTAA 1652

TGGAGTTTAAAAATTCCTACGCCTAGTGATATCATAGTTGCCTTAAGATCATAACACAACACATTTCTCACGCGTTTGT 1731

GGTGATGCTGGTACAAACAAGCTACAGCGCCGCTAGTCATATACAAATATAGCACATACAATTATGTACAGTACACTAT 1810

ACTTGATAATGATAATAAACAACTATGTTACTGGTTTATGTAAAAAAAAAAAAAAAAAAAAAA               1872

FIG. 1B ig: domain 1 of 3, from 27 to 80: score 15.3, E = 0.0035
```
              *->GesvtLtCsvsgfgpp.p.vtWlrngk........lslti.svtpeD
                 G+ vtL+C    + p  +v+ +r+gk  + ++++ +] ++ +t
     FAIL  27    GDALTLRCQGW-KNTPlSqVKFYRDGKflhfskenQTLSMgAATVQS 72 sgGtYtCvv<-*
                 G  Y+C
     FAIL  73 R-GQYSCSG    80
```

FIG.3A ig: domain 2 of 3, from 120 to 177: score 25.0, E = 3.5e-06
```
              *->GesvtLtCsvsgfgpp.p.vtWl....rngk........lslti.sv
                 G+ vtL+C +  +p +  +++] + +++g++ ++++++  ] i+ +
     FAIL  120   GSLVTLRCQTK-LHPLrSaLRLLfsfhKDGHtlqdrgphPELCIpGA 165 tpeDsgGtYtCvv<-*
                 +++Ds G Y+C+v
     FAIL  166 KEGDS-GLYWCEV    177
```

FIG.3B ig: domain 3 of 3, from 216 to 273: score 16.7, E = 0.0013
```
              *->GesvtLtCsvsgfgpp.p.vtWlrngk............islti.sv
                 G+ v L C++    g+p++ ++ + + k  ++++ + ++++sl+++
     FAIL  216   GDMVQLLCEAQ-RGSPpIlYSFYLDEKivgnhsapcggtTSLLFpVK 261 tpeDsgGtYtCvv<-*
                 ++ D+ G+Y+C++
     FAIL  262 SEQDA-GNYSCEA    273
```

FIG.3C

Alignment Report of FAIL aligned, using Clustal method with PAM250 residue weight table.
Friday, July 28, 2000 7:49 AM

```
hFAIL        M . . . . . . . L P S L V P . . . . . C V G K T V L . . . . . . . Y L Q A . . . . . . . . . . . . . . . .     19
hFC-GAMMA RI M . . . . . . . . . . . . . . . . . . . . . . . . . . . . . . . . F L I T L L W V P V D G Q V D T T - K A     22
hFC-GAMMA RIIA  M A . . . . . . . . . . . . . . . . . . . . . . . . . . . F L L Q P L - L V L L L A S A D S Q A A A P P K A     41
hFC-GAMMA RIIB  M G I L S F L P V L . . M E Q M S Q N V C . P R N L L L Q P G H M L W T A V L F L A P V A G T P A A P P K A     50
hFC-GAMMA RIIC  M G I L S F L P V L A I E S D W A D C K S P Q P G H M L W T A V L F L A P V A G T P A A P P K A     50
hFC-GAMMA RIIIa M . . . . . . . . . . A I E S D W A D C K S P Q P W . . . . . . . . . . . . . . . . . . . . . . .     26
hFCERI          M A . . . . . P A M E S P T . . . . . . . . . . . Q L L P T A L L L L V S A G M R T E D L P K A     30 hFAIL        . . . . . . . V I S Q P P W V S . V F Q E E T V I H C E V L L P G S S S T Q W F L N C T A T Q . . . I S L P S     62
hFC-GAMMA RI M P N P V F E G D A L L R C Q E W K N T P L S Q V K F Y R D C K F L H F S K E N Q T     69
hFC-GAMMA RIIA V L K L E P P W I N . V L Q E D S V T L T C Q G A R S P E S D S I Q W F H N G N L I P . . . I H T Q P     88
hFC-GAMMA RIIB V L K L E P P W I N . V L Q E D S V T L T C R E T H S P E S D S I Q W F H N G N L I P . . . L H T Q P     97
hFC-GAMMA RIIC V L K L E P Q W I N . V L Q E D S V T L T C R E T H S P E S D S I Q W F H N G N L I P . . . L H T Q P     97
hFC-GAMMA RIIIa V V F L E P Q W Y R . V L E K D S V T L K C Q G A Y S P E D N S T Q W F H N E S L I S . . S Q A S S     73
hFCERI       K V S L N P P W N R . I F K G E N V T L T C N G N N F F E V S S T K W F H N G S L S E . . E T N S S     77 hFAIL        L S M G A A T V Q S R C Q V S G Q V M Y I P Q T F T Q T S E T A M V Q V Q E L F P P P V L S A I     112
hFC-GAMMA RI Y R I T S A S V N D S G E Y R C Q R E . . . . . . . L S G R S D P I Q L . E I H R G W L L Q V     109
hFC-GAMMA RIIA S Y R F K A N N D S G E Y T C Q T G . . . . . . . Q T S L S D P V H L . T V L S E W L V L Q I     128
hFC-GAMMA RIIB S Y R F K A N N D S G E Y T C Q T G . . . . . . . Q T S L S D P V H L . T V L S E W L V L Q I     137
hFC-GAMMA RIIC S Y R F K A N N D S G E Y T C Q T G . . . . . . . Q T S L S D P V H L . T V L S E W L V L Q I     137
hFC-GAMMA RIIIa Y F D A A T V D D S G E Y R C Q T N . . . . . . . L S T L S D P V Q L . E V H I G W L L L Q A     113
hFCERI        L N I V N A K F E D S G E Y K C Q H Q . . . . . . . Q V N E S E P V Y L . E V F S D W L L L Q A     117
```

```
Alignment Report of FAIL aligned, using Clustal method with PAM250 residue weight table.
Friday, July 28, 2000 7:49 AM hFAIL          PVKSEQDAGNYSCEAENSVSRERSEPKLSLKGSQVLFTPASNWLVPWLP    308
hFC-GAMMA RI   TARRE-DSGLYWEA-ATEDGNVLKRSPELELQVLELPTPVWF-------    291
hFC-GAMMA RIIA -------------CRK--KRISANSTDPVKAAQFEPPGRQMIA------    268
hFC-GAMMA RIIB -------------CRK--KRISA-----LPGY-PECREWGE--------    266
hFC-GAMMA RIIC -------------CRK--KRISANSTDPVKAAQFEPPGRQMIA------    274
hFC-GAMMA RIIIa ---------------------------SSFPPGYQVSF----------    211
hFCERI         ------------------AVDTGLFISTQQVTF---------------    232 hFAIL          ASLLGLMVIAAALLVYVRSWRKAVHHQKGKDE---GVVYSVVHRTSKRS   354
hFC-GAMMA RI   -HVLFYLAVGIMFLVNTVLWVTIRKELKRKKKWDLEISLDSGHEKKVTS   340
hFC-GAMMA RIIA --------------------IRKRQLETNNDYETADGGYMLNP--RAP   296
hFC-GAMMA RIIB ---------------------TLPEKPANPTNPDEADKVG--------   285
hFC-GAMMA RIIC --------------------IRKRQPETNNDYETADGGYMLNP--RAP   302
hFC-GAMMA RIIIa ---------------------CLVMVL----FAVDTELVFSVKTNIRS   236
hFCERI         --------------------LLKIKRTRK-------CFRLLNPHPKPN   253 hFAIL          EGQ----FYHLCGGEMPAAQ                              370
hFC-GAMMA RI   LQEDRHLEEELKCQEQKEEQLQEGVHRKEPQGAT                374
hFC-GAMMA RIIA IDDDKNIYLTLPPNDHVNSNN                             317
hFC-GAMMA RIIB AENTITYSLMHPDALEEPDDQNRI                          310
hFC-GAMMA RIIC IDDDKNIYLTLPPNDHVNSNN                             323
hFC-GAMMA RIIIa IRDWKDHKFKWRKDPQDK                                254
hFCERI         PKNN                                              257
```

Decoration 'Decoration #1': Shade (with solid black) residues that match the Consensus exactly.

FIG.4C

Alignment Report of Untitled, using Clustal method with Weighted residue weight table.
Wednesday, October 4, 2000 9:08 AM

```
FAIL ORF        ATGTTGCCATCTTTAGTTCCCTGTGTTGGGAAAACTGTCT  40
Fc-gammaRI ORF  ATGTGGTTCTTGACAACTCTGCTCCTTTGGGTTCCAGT-T  39

FAIL ORF        GGCTGTACCTCCAAGCCTGGCCAAACCCTGTGTTTGAA    78
Fc-gammaRI ORF  GA-TGGGCAAGTGGACACCAC-AAAGGCAGTGATTCACTTT 77

FAIL ORF        GGAGATGCCCTGACTCTGCGATGTCAGGGATGGAAGAATA 118
Fc-gammaRI ORF  GCAGCCTCCATGGGTCAGCGTGTTCCAAGAGGAAACCGTA 117

FAIL ORF        CACCACTGTCTCAGGTGAAGTTCTACAGAGATGGAAA AT 157
Fc-gammaRI ORF  -ACC-TTGCACTGTGAGGTGCTCCATCTGCCTGGGAGCAG 155

FAIL ORF        TCCTTCA----    TTTCTCTAAGGAAAACCAGACTCTGTC 191
Fc-gammaRI ORF  CTCTACACAGTGGTTTCTCAATGGCACAGCC-ACTCAGAC 194

FAIL ORF        CATGGAGCAGCAACAGTGCAGAGCCGTGGCCAGTACAGC  231
Fc-gammaRI ORF  CTC--GACCCCAGC--TACAGAATCACCTCTGCCAGTGT  230

FAIL ORF        TGCTCTGGGCAGGTGATGTATATTCCACAGACATTCACAC 271
Fc-gammaRI ORF  CAATGACAGTGGTGAATACAGGTGCCAGAGAGGTCT-CTC 269

FAIL ORF        AAACTTCAGAGACTGC-CATGGTTCAAGTCCAAGAGCTGT 310
Fc-gammaRI ORF  AGGGCGAAGTGACCCCATACAGCTGGAAATCCACAGAGGC 309

FAIL ORF        TTCCACCTCCTGTGCTGAGTGCCATCCCCTCTCCTGAGCC 350
Fc-gammaRI ORF  TGGCTACTACTGCA---GGTCTCCAGCAGAGTCTTCA--- 343

FAIL ORF        CCGAGAGGGTAGCCTGGTGACCCTGAGATGTCAGACAAAG 390
Fc-gammaRI ORF  -CGGAAGGAGAACCTC-TGGCCTTGAGGTGTCATGCG--- 378

FAIL ORF        CTGCACCCCCTGAGGTCAGCCTTGAGGCTCCTTTTCTCCT 430
Fc-gammaRI ORF  -TGGA------AGGATAAGC--TGGTGTACAATGTGCTTT 409

FAIL ORF        TCCACAAGGACGGCCACACCTTGCAGGACAGGGGCCCTCA 470
Fc-gammaRI ORF  ACTATCGAAATGGCAAAGCCTTTAAGTTTTCCACTGGAA  449

FAIL ORF        CCCAGAACTCTGCATCCCGGGAGCCAAGGAGGGAGACTCT 510
Fc-gammaRI ORF  TTCTAACCTCACCATTCTGAAAACCAACATAAGTCACAAT 489

FAIL ORF        GGGCTTTACTGGTGTGAGGTGGCCCCTGAGGGTGGCCAGG 550
Fc-gammaRI ORF  GGCACCTACCATTGCTCAG--GCATGGGAAAGCATCGCTA 527

FAIL ORF        TCCAGAAGCAGAGCCCCCAGCTGGAGGTCAGAGTGCAGGC 590
Fc-gammaRI ORF  CACATCAGCAGGAATATCTGTCACTG-TGAAAGAGCTATT 566

FAIL ORF        TCCTGTATCCCGTCCTGTGCTCACTCTGCACCACGGGCCT 630
Fc-gammaRI ORF  TCCAGC-TCCAGTGCTGAATGCA-TCTGTGACATC--CCC 602

FAIL ORF        GCTGACCCTGCTGTGGGGGACATGGTGCAGCTCCTCTGTG 670
Fc-gammaRI ORF  ACT---CCTG--GAGGGGAATCTGGTTCACCCTGAGCTGTG 637
```

FIG.5A

```
FAIL ORF        AGGCACAGAGGGGCTCCCCTCCGATCCTGTATTCCTTCTA  710
Fc-gammaRI ORF  AA--ACAAAGTTGCTCTTGCAGAGGCCTG-GTTT--TGCAG  672

FAIL ORF        CCTTGATGAGAAGATTGTGGGGAACCACTCAGCTCCCTGT  750
Fc-gammaRI ORF  CTTTACTTCTCCTTCTACATGGG-CAGCAAGACCCTGCGA  711

FAIL ORF        GGTGGAACCACCTCCCTCCTCTTCCCAGTG--AA  GTCA  786
Fc-gammaRI ORF  GGCAGGAACACATCCTCTGAATACCAAATTACTAACTGCTA 751

FAIL ORF        GAACAG- GATGCTGGGAACTACTCCTGCGAGGCTGAGAA  824
Fc-gammaRI ORF  GAAGAGAAGACTCTGGGTTATACTGGTGCGAGGCTG----  787

FAIL ORF        CAGTGTCTCCAGAGAGAGGAGTGAGCCCAAGAAGCTGTCT  864
Fc-gammaRI ORF  ------CCACAGAGGATGGAAATGTCCTTAAGCGCAGCC-  820

FAIL ORF        CTGAA--GGGTTCTCAAGTCTTGTTCACTCCCGCCAGCAA  902
Fc-gammaRI ORF  CTGAGTTGGAGCTTCAAGT---GCTTGGCCTC--CAGTTA  855

FAIL ORF        CTGGCTGGTTCCTTGGCTTCCTGCGAGCCTGCTTGGCCTG  942
Fc-gammaRI ORF  CCAACTC-CTTGTCTGGTTTCATCT---CCTTTTCTATCTG 891

FAIL ORF        ATGGTTATTGCTGCTGCACTTCTGGTTTATGTGAGATCCT  982
Fc-gammaRI ORF  GCAGTT---GGGAATAATGTTTTTAGTGAACACTGTTCTCT 928

FAIL ORF        GGA-GAAAAGCTGTGCATCACCAGAAAGGGAAAGATGAAG 1021
Fc-gammaRI ORF  GGGTGACAATACGTAAAGAACTGAAAAGAAAGAAAAAGTG  968

FAIL ORF        GTGTTGTCTACTCTGTGGTGCATAGAACCTCAAAGAGGAG 1061
Fc-gammaRI ORF  GGATTTAGAAATCTCTT-----TGGATTCTGGAGGCCAAG 1003

FAIL ORF        TGAAGGACAGTTCTATCATCTGTGCGGAGGTGAGATGCCT 1101
Fc-gammaRI ORF  CACTTGA-AGCTC---CAACT---CAGGG--------CT  1027

FAIL ORF        GCAGCCCAGTGA                              1113
Fc-gammaRI ORF  GC-GCTTA---A                              1035

Decoration 'Decoration #1': Shade (with solid black) residues that
match FAIL ORF exactly.
```

FIG.5B

```
hFAIL          M--LPSL---VPCVGKT--------------VWL--------          15
hFC-GAMMA RI   MWFLTTLLLWVPVDGQVDTTKAVISLQPPWVSVFQEETVT            40 hFAIL          ----------------YLQA--------------------            19
hFC-GAMMA RI   LHCEVLHLPGSSSTQWFLNGTATQTSTPSYRITSASVNDS            80 hFAIL          ------------------------W-----PNPVF-EGDAL          30
hFC-GAMMA RI   GEYRCQRGLSGRSDPIQLEIHRGWLLLQVSSRVFTEGEPL           120 hFAIL          TLRCQGWKNTPLSQVKFYRDGKFLHFSKENQTLSMGAATV            70
hFC-GAMMA RI   ALRCHAWKDKLVYNVLYYRNGKAFKFFHWNSNLTILKTNI           160 hFAIL          QSRGQYSCSGQVMYIPQTFTQTSETAMVQVQELFPPPVLS           110
hFC-GAMMA RI   SHNGTYHCSGMGK---HRYTSAGIS--VTVKELFPAPVLN           195 hFAIL          AIPSPEPREGSLVTLRCQTKLHPLRSALRLLFSFHKDGHT           150
hFC-GAMMA RI   ASVTSPLLEGNLVTLSCETKLLLQRPGLQLYFSFYMGSKT           235 hFAIL          LQDRGPHPELCIPGAKEGDSGLYWCEVAPEGGQVQKQSPQ           190
hFC-GAMMA RI   LRGRNTSSEYQILTARREDSGLYWCEAATEDGNVLKRSPE           275 hFAIL          LEVRVQAPVSRPVLTLHHGPADPAVGDMVQLLCEAQRGSP           230
hFC-GAMMA RI   LELQV--------LGLQL------------------PT             287 hFAIL          PILYS--FYLDEKIVGNHSAPCGGTTSLLFPVKSEQDAGN           268
hFC-GAMMA RI   PVWFHVLFYL-------------AVGIMFLVNTVLWV--           311 hFAIL          YSCEAENSVSRERSEPKKLSLKGSQVLFTPASNWLVPWLP           308
hFC-GAMMA RI   -------TIRKELKRKKKWDLEIS--LDSGHEKKVTSSLQ           342 hFAIL          ASLLGLMVIAAALLVYVRSWRKAVHHQKGKDEGVVYSVVH           346
hFC-GAMMA RI   ED--------------------RHLEEELKCQEQKEEQLQ-EGVH       366 hFAIL          RTSKRSEGQFYHLCGGEMPAAQ                              370
hFC-GAMMA RI   RK--------EPQGAT                                    374
```

Percent identity:22.7% between FAIL and FcgammaR1 (genbank accession no. AAA35678)

FIG.6

SEQUENCE LISTING

<160> NUMBER OF SEQ ID NOS: 45

<210> SEQ ID NO 1
<211> LENGTH: 1872
<212> TYPE: DNA
<213> ORGANISM: Homo sapiens

<400> SEQUENCE: 1

```
gtcgacccac gcgtccgcaa ctcaggagat ctgttggaaa gagaacgata gaggaaaata      60
tatgaatgtt gccatcttta gttccctgtg ttgggaaaac tgtctggctg tacctccaag     120
cctggccaaa ccctgtgttt gaaggagatg ccctgactct gcgatgtcag ggatggaaga     180
atacaccact gtctcaggtg aagttctaca gagatggaaa attccttcat ttctctaagg     240
aaaaccagac tctgtccatg ggagcagcaa cagtgcagag ccgtggccag tacagctgct     300
ctgggcaggt gatgtatatt ccacagacat tcacacaaac ttcagagact gccatggttc     360
aagtccaaga gctgtttcca cctcctgtgc tgagtgccat cccctctcct gagccccgag     420
agggtagcct ggtgaccctg agatgtcaga caaagctgca cccctgagg tcagccttga     480 ggctcctttt ctccttccac aaggacggcc acaccttgca ggacagggc cctcacccag     540 aactctgcat cccgggagcc aaggaggag actctgggct ttactggtgt gaggtggccc     600
ctgagggtgg ccaggtccag aagcagagcc cccagctgga ggtcagagtg caggctcctg     660
tatcccgtcc tgtgctcact ctgcaccacg ggcctgctga ccctgctgtg ggggacatgg     720
tgcagctcct ctgtgaggca cagagggct cccctccgat cctgtattcc ttctaccttg     780
atgagaagat tgtggggaac cactcagctc cctgtggtgg aaccacctcc ctcctcttcc     840
cagtgaagtc agaacaggat gctgggaact actcctgcga ggctgagaac agtgtctcca     900
gagagaggag tgagcccaag aagctgtctc tgaagggttc tcaagtcttg ttcactcccg     960
ccagcaactg gctggttcct tggcttcctg cgagcctgct tggcctgatg gttattgctg    1020
ctgcacttct ggtttatgtg agatcctgga gaaagctgt gcatcaccag aaagggaaag    1080
```

-continued

```
atgaaggtgt tgtctactct gtggtgcata gaacctcaaa gaggagtgaa ggacagttct    1140
atcatctgtg cggaggtgag atgcctgcag cccagtgagg tttcatccac ggaggtgaat    1200
atgagaagca ggactctcca agaacccctt agcgactgtg aggaggttct ctgctagtga    1260
tggtgttctc ctatcaacac acgcccaccc ccagtctcca gtgctcctca ggaagacagt    1320
ggggtcctca actctttctg tgggtccttc agttcccaag cccagcatca cagagccccc    1380
tgagcccttg tcctggtcag gagcacctga accctgggtt cttttcttag cagaagacca    1440
accaatggaa tgggaaggga gatgctccca ccaacacaca cacttaggtt caatcagtga    1500
cactggacac ataagccaca gatgtcttct ttccatacaa gcatgttagt tcgccccaat    1560
atacatatat atatgaaata gtcatgtgcc gcataacaac atttcagtca gtgatagact    1620
gcatacacaa cagtggtccc ataagactgt aatggagttt aaaaattcct acgcctagtg    1680
atatcatagt tgccttaaca tcataacaca acacatttct cacgcgtttg tggtgatgct    1740
ggtacaaaca agctacagcg ccgctagtca tatacaaata tagcacatac aattatgtac    1800
agtacactat acttgataat gataataaac aactatgtta ctggtttatg taaaaaaaaa    1860
aaaaaaaaaa aa                                                        1872
```

<210> SEQ ID NO 2
<211> LENGTH: 1110
<212> TYPE: DNA
<213> ORGANISM: Homo sapiens

<400> SEQUENCE: 2

```
atgttgccat ctttagttcc ctgtgttggg aaaactgtct ggctgtacct ccaagcctgg      60
ccaaaccctg tgtttgaagg agatgccctg actctgcgat gtcagggatg aagaataca     120 ccactgtctc aggtgaagtt ctacagagat ggaaaattcc ttcatttctc taaggaaaac    180
cagactctgt ccatgggagc agcaacagtg cagagccgtg gccagtacag ctgctctggg    240
caggtgatgt atattccaca gacattcaca caaacttcag agactgccat ggttcaagtc    300
caagagctgt ttccacctcc tgtgctgagt gccatcccct ctcctgagcc ccgagagggt    360
agcctggtga ccctgagatg tcagacaaag ctgcaccccc tgaggtcagc cttgaggctc    420
cttttctcct tccacaagga cggccacacc ttgcaggaca ggggccctca cccagaactc    480
tgcatcccgg gagccaagga gggagactct gggctttact ggtgtgaggt ggcccctgag    540
ggtggccagg tccagaagca gagccccag ctggaggtca gagtgcaggc tcctgtatcc    600
cgtcctgtgc tcactctgca ccacgggcct gctgaccctg ctgtggggga catggtgcag    660
ctcctctgtg aggcacagag gggctcccct ccgatcctgt attccttcta ccttgatgag    720
aagattgtgg ggaaccactc agctcccctgt ggtggaacca cctccctcct cttcccagtg    780
aagtcagaac aggatgctgg gaactactcc tgcgaggctg agaacagtgt ctccagagag    840
aggagtgagc ccaagaagct gtctctgaag ggttctcaag tcttgttcac tcccgccagc    900
aactggctgg ttccttggct tcctgcgagc ctgcttggcc tgatggttat gctgctgca     960 cttctggttt atgtgagatc ctggagaaaa gctgtgcatc accagaaagg gaaagatgaa    1020
ggtgttgtct actctgtggt gcatagaacc tcaaagagga gtgaaggaca gttctatcat    1080
ctgtgcggag gtgagatgcc tgcagcccag                                     1110
```

<210> SEQ ID NO 3
<211> LENGTH: 370
<212> TYPE: PRT
<213> ORGANISM: Homo sapiens

```
<400> SEQUENCE: 3

Met Leu Pro Ser Leu Val Pro Cys Val Gly Lys Thr Val Trp Leu Tyr
  1               5                  10                  15

Leu Gln Ala Trp Pro Asn Pro Val Phe Glu Gly Asp Ala Leu Thr Leu
             20                  25                  30

Arg Cys Gln Gly Trp Lys Asn Thr Pro Leu Ser Gln Val Lys Phe Tyr
         35                  40                  45

Arg Asp Gly Lys Phe Leu His Phe Ser Lys Glu Asn Gln Thr Leu Ser
     50                  55                  60

Met Gly Ala Ala Thr Val Gln Ser Arg Gly Gln Tyr Ser Cys Ser Gly
 65                  70                  75                  80

Gln Val Met Tyr Ile Pro Gln Thr Phe Thr Gln Thr Ser Glu Thr Ala
                 85                  90                  95

Met Val Gln Val Gln Glu Leu Phe Pro Pro Val Leu Ser Ala Ile
            100                 105                 110

Pro Ser Pro Glu Pro Arg Glu Gly Ser Leu Val Thr Leu Arg Cys Gln
            115                 120                 125

Thr Lys Leu His Pro Leu Arg Ser Ala Leu Arg Leu Leu Phe Ser Phe
130                 135                 140

His Lys Asp Gly His Thr Leu Gln Asp Arg Gly Pro His Pro Glu Leu
145                 150                 155                 160

Cys Ile Pro Gly Ala Lys Glu Gly Asp Ser Gly Leu Tyr Trp Cys Glu
                165                 170                 175

Val Ala Pro Glu Gly Gly Gln Val Gln Lys Gln Ser Pro Gln Leu Glu
            180                 185                 190

Val Arg Val Gln Ala Pro Val Ser Arg Pro Val Leu Thr Leu His His
        195                 200                 205

Gly Pro Ala Asp Pro Ala Val Gly Asp Met Val Gln Leu Leu Cys Glu
210                 215                 220

Ala Gln Arg Gly Ser Pro Pro Ile Leu Tyr Ser Phe Tyr Leu Asp Glu
225                 230                 235                 240

Lys Ile Val Gly Asn His Ser Ala Pro Cys Gly Thr Thr Ser Leu
                245                 250                 255

Leu Phe Pro Val Lys Ser Glu Gln Asp Ala Gly Asn Tyr Ser Cys Glu
            260                 265                 270

Ala Glu Asn Ser Val Ser Arg Glu Arg Ser Glu Pro Lys Lys Leu Ser
        275                 280                 285

Leu Lys Gly Ser Gln Val Leu Phe Thr Pro Ala Ser Asn Trp Leu Val
    290                 295                 300

Pro Trp Leu Pro Ala Ser Leu Leu Gly Leu Met Val Ile Ala Ala Ala
305                 310                 315                 320

Leu Leu Val Tyr Val Arg Ser Trp Arg Lys Ala Val His Gln Lys
                325                 330                 335

Gly Lys Asp Glu Gly Val Val Tyr Ser Val Val His Arg Thr Ser Lys
            340                 345                 350

Arg Ser Glu Gly Gln Phe Tyr His Leu Cys Gly Gly Glu Met Pro Ala
        355                 360                 365

Ala Gln
    370

<210> SEQ ID NO 4
<211> LENGTH: 27
<212> TYPE: PRT
```

-continued

<213> ORGANISM: Homo sapiens

<400> SEQUENCE: 4

Met Leu Pro Ser Leu Val Pro Cys Val Gly Lys Thr Val Trp Leu Tyr
1               5                   10                  15

Leu Gln Ala Trp Pro Asn Pro Val Phe Glu Gly
            20                  25

<210> SEQ ID NO 5
<211> LENGTH: 343
<212> TYPE: PRT
<213> ORGANISM: Homo sapiens

<400> SEQUENCE: 5

Asp Ala Leu Thr Leu Arg Cys Gln Gly Trp Lys Asn Thr Pro Leu Ser
1               5                   10                  15

Gln Val Lys Phe Tyr Arg Asp Gly Lys Phe Leu His Phe Ser Lys Glu
            20                  25                  30

Asn Gln Thr Leu Ser Met Gly Ala Ala Thr Val Gln Ser Arg Gly Gln
        35                  40                  45

Tyr Ser Cys Ser Gly Gln Val Met Tyr Ile Pro Gln Thr Phe Thr Gln
    50                  55                  60

Thr Ser Glu Thr Ala Met Val Gln Val Gln Glu Leu Phe Pro Pro Pro
65                  70                  75                  80

Val Leu Ser Ala Ile Pro Ser Pro Glu Pro Arg Glu Gly Ser Leu Val
                85                  90                  95

Thr Leu Arg Cys Gln Thr Lys Leu His Pro Leu Arg Ser Ala Leu Arg
            100                 105                 110

Leu Leu Phe Ser Phe His Lys Asp Gly His Thr Leu Gln Asp Arg Gly
        115                 120                 125

Pro His Pro Glu Leu Cys Ile Pro Gly Ala Lys Glu Gly Asp Ser Gly
    130                 135                 140

Leu Tyr Trp Cys Glu Val Ala Pro Glu Gly Gly Gln Val Gln Lys Gln
145                 150                 155                 160

Ser Pro Gln Leu Glu Val Arg Val Gln Ala Pro Val Ser Arg Pro Val
                165                 170                 175

Leu Thr Leu His His Gly Pro Ala Asp Pro Ala Val Gly Asp Met Val
            180                 185                 190

Gln Leu Leu Cys Glu Ala Gln Arg Gly Ser Pro Pro Ile Leu Tyr Ser
        195                 200                 205

Phe Tyr Leu Asp Glu Lys Ile Val Gly Asn His Ser Ala Pro Cys Gly
    210                 215                 220

Gly Thr Thr Ser Leu Leu Phe Pro Val Lys Ser Glu Gln Asp Ala Gly
225                 230                 235                 240

Asn Tyr Ser Cys Glu Ala Glu Asn Ser Val Ser Arg Glu Arg Ser Glu
                245                 250                 255

Pro Lys Lys Leu Ser Leu Lys Gly Ser Gln Val Leu Phe Thr Pro Ala
            260                 265                 270

Ser Asn Trp Leu Val Pro Trp Leu Pro Ala Ser Leu Leu Gly Leu Met
        275                 280                 285

Val Ile Ala Ala Ala Leu Leu Val Tyr Val Arg Ser Trp Arg Lys Ala
    290                 295                 300

Val His His Gln Lys Gly Lys Asp Glu Gly Val Val Tyr Ser Val Val
305                 310                 315                 320

His Arg Thr Ser Lys Arg Ser Glu Gly Gln Phe Tyr His Leu Cys Gly

```
                    325                 330                 335
Gly Glu Met Pro Ala Ala Gln
                340

<210> SEQ ID NO 6
<211> LENGTH: 278
<212> TYPE: PRT
<213> ORGANISM: Homo sapiens

<400> SEQUENCE: 6

Asp Ala Leu Thr Leu Arg Cys Gln Gly Trp Lys Asn Thr Pro Leu Ser
 1               5                  10                  15

Gln Val Lys Phe Tyr Arg Asp Gly Lys Phe Leu His Phe Ser Lys Glu
            20                  25                  30

Asn Gln Thr Leu Ser Met Gly Ala Ala Thr Val Gln Ser Arg Gly Gln
        35                  40                  45

Tyr Ser Cys Ser Gly Gln Val Met Tyr Ile Pro Gln Thr Phe Thr Gln
    50                  55                  60

Thr Ser Glu Thr Ala Met Val Gln Val Gln Glu Leu Phe Pro Pro Pro
65                  70                  75                  80

Val Leu Ser Ala Ile Pro Ser Pro Glu Pro Arg Glu Gly Ser Leu Val
                85                  90                  95

Thr Leu Arg Cys Gln Thr Lys Leu His Pro Leu Arg Ser Ala Leu Arg
            100                 105                 110

Leu Leu Phe Ser Phe His Lys Asp Gly His Thr Leu Gln Asp Arg Gly
        115                 120                 125

Pro His Pro Glu Leu Cys Ile Pro Gly Ala Lys Glu Gly Asp Ser Gly
    130                 135                 140

Leu Tyr Trp Cys Glu Val Ala Pro Glu Gly Gly Gln Val Gln Lys Gln
145                 150                 155                 160

Ser Pro Gln Leu Glu Val Arg Val Gln Ala Pro Val Ser Arg Pro Val
                165                 170                 175

Leu Thr Leu His His Gly Pro Ala Asp Pro Ala Val Gly Asp Met Val
            180                 185                 190

Gln Leu Leu Cys Glu Ala Gln Arg Gly Ser Pro Pro Ile Leu Tyr Ser
        195                 200                 205

Phe Tyr Leu Asp Glu Lys Ile Val Gly Asn His Ser Ala Pro Cys Gly
    210                 215                 220

Gly Thr Thr Ser Leu Leu Phe Pro Val Lys Ser Glu Gln Asp Ala Gly
225                 230                 235                 240

Asn Tyr Ser Cys Glu Ala Glu Asn Ser Val Ser Arg Glu Arg Ser Glu
                245                 250                 255

Pro Lys Lys Leu Ser Leu Lys Gly Ser Gln Val Leu Phe Thr Pro Ala
            260                 265                 270

Ser Asn Trp Leu Val Pro
        275

<210> SEQ ID NO 7
<211> LENGTH: 20
<212> TYPE: PRT
<213> ORGANISM: Homo sapiens

<400> SEQUENCE: 7

Trp Leu Pro Ala Ser Leu Leu Gly Leu Met Val Ile Ala Ala Ala Leu
 1               5                  10                  15

Leu Val Tyr Val
```

```
<210> SEQ ID NO 8
<211> LENGTH: 45
<212> TYPE: PRT
<213> ORGANISM: Homo sapiens

<400> SEQUENCE: 8

Arg Ser Trp Arg Lys Ala Val His His Gln Lys Gly Lys Asp Glu Gly
  1               5                  10                  15

Val Val Tyr Ser Val Val His Arg Thr Ser Lys Arg Ser Glu Gly Gln
             20                  25                  30

Phe Tyr His Leu Cys Gly Gly Glu Met Pro Ala Ala Gln
         35                  40                  45

<210> SEQ ID NO 9
<211> LENGTH: 54
<212> TYPE: PRT
<213> ORGANISM: Homo sapiens

<400> SEQUENCE: 9

Gly Asp Ala Leu Thr Leu Arg Cys Gln Gly Trp Lys Asn Thr Pro Leu
  1               5                  10                  15

Ser Gln Val Lys Phe Tyr Arg Asp Gly Lys Phe Leu His Phe Ser Lys
             20                  25                  30

Glu Asn Gln Thr Leu Ser Met Gly Ala Ala Thr Val Gln Ser Arg Gly
         35                  40                  45

Gln Tyr Ser Cys Ser Gly
     50

<210> SEQ ID NO 10
<211> LENGTH: 58
<212> TYPE: PRT
<213> ORGANISM: Homo sapiens

<400> SEQUENCE: 10

Gly Ser Leu Val Thr Leu Arg Cys Gln Thr Lys Leu His Pro Leu Arg
  1               5                  10                  15

Ser Ala Leu Arg Leu Leu Phe Ser Phe His Lys Asp Gly His Thr Leu
             20                  25                  30

Gln Asp Arg Gly Pro His Pro Glu Leu Cys Ile Pro Gly Ala Lys Glu
         35                  40                  45

Gly Asp Ser Gly Leu Tyr Trp Cys Glu Val
     50                  55

<210> SEQ ID NO 11
<211> LENGTH: 58
<212> TYPE: PRT
<213> ORGANISM: Homo sapiens

<400> SEQUENCE: 11

Gly Asp Met Val Gln Leu Leu Cys Glu Ala Gln Arg Gly Ser Pro Pro
  1               5                  10                  15

Ile Leu Tyr Ser Phe Tyr Leu Asp Glu Lys Ile Val Gly Asn His Ser
             20                  25                  30

Ala Pro Cys Gly Gly Thr Thr Ser Leu Leu Phe Pro Val Lys Ser Glu
         35                  40                  45

Gln Asp Ala Gly Asn Tyr Ser Cys Glu Ala
     50                  55
```

-continued

<210> SEQ ID NO 12
<211> LENGTH: 44
<212> TYPE: PRT
<213> ORGANISM: Homo sapiens

<400> SEQUENCE: 12

Gly Glu Ser Val Thr Leu Thr Cys Ser Val Gly Phe Gly Pro Pro Pro
1               5                   10                  15

Val Thr Trp Leu Arg Asn Gly Lys Ile Ser Leu Thr Ile Ser Val Thr
            20                  25                  30

Pro Glu Asp Ser Gly Gly Thr Tyr Thr Cys Val Val
        35                  40

<210> SEQ ID NO 13
<211> LENGTH: 1035
<212> TYPE: DNA
<213> ORGANISM: Homo sapiens

<400> SEQUENCE: 13
atgtggttct tgacaactct gctcctttgg gttccagttg atgggcaagt ggacaccaca      60
aaggcagtga tcactttgca gcctccatgg gtcagcgtgt tccaagagga aaccgtaacc     120
ttgcactgtg aggtgctcca tctgcctggg agcagctcta cacagtggtt tctcaatggc     180
acagccactc agacctcgac ccccagctac agaatcacct ctgccagtgt caatgacagt     240
ggtgaataca ggtgccagag aggtctctca gggcgaagtg accccataca gctggaaatc     300
cacagaggct ggctactact gcaggtctcc agcagagtct tcacggaagg agaacctctg     360
gccttgaggt gtcatgcgtg gaaggataag ctggtgtaca atgtgcttta ctatcgaaat     420
ggcaaagcct ttaagttttt ccactggaat tctaacctca ccattctgaa accaacata      480 agtcacaatg gcacctacca ttgctcaggc atgggaaagc atcgctacac atcagcagga     540
atatctgtca ctgtgaaaga gctatttcca gctccagtgc tgaatgcatc tgtgacatcc     600
ccactcctgg aggggaatct ggtcaccctg agctgtgaaa caaagttgct cttgcagagg     660
cctggtttgc agctttactt ctccttctac atgggcagca agaccctgcg aggcaggaac     720
acatcctctg aataccaaat actaactgct agaagagaag actctgggtt atactggtgc     780
gaggctgcca cagaggatgg aaatgtcctt aagcgcagcc tgagttgga gcttcaagtg      840 cttggcctcc agttaccaac tcctgtctgg tttcatgtcc ttttctatct ggcagtggga     900
ataatgtttt tagtgaacac tgttctctgg gtgacaatac gtaaagaact gaaaagaaag     960
aaaaagtggg atttagaaat ctctttggat tctggaggcc aagcacttga agctccaact    1020
cagggctgcg cttaa                                                     1035

<210> SEQ ID NO 14
<211> LENGTH: 374
<212> TYPE: PRT
<213> ORGANISM: Homo sapiens

<400> SEQUENCE: 14

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln

```
                50                   55                   60
Thr Ser Thr Pro Ser Tyr Arg Ile Thr Ser Ala Ser Val Asn Asp Ser
 65                   70                   75                   80

Gly Glu Tyr Arg Cys Gln Arg Gly Leu Ser Gly Arg Ser Asp Pro Ile
                     85                   90                   95

Gln Leu Glu Ile His Arg Gly Trp Leu Leu Gln Val Ser Ser Arg
                100                  105                  110

Val Phe Thr Glu Gly Glu Pro Leu Ala Leu Arg Cys His Ala Trp Lys
                115                  120                  125

Asp Lys Leu Val Tyr Asn Val Leu Tyr Tyr Arg Asn Gly Lys Ala Phe
130                  135                  140

Lys Phe Phe His Trp Asn Ser Asn Leu Thr Ile Leu Lys Thr Asn Ile
145                  150                  155                  160

Ser His Asn Gly Thr Tyr His Cys Ser Gly Met Gly Lys His Arg Tyr
                165                  170                  175

Thr Ser Ala Gly Ile Ser Val Thr Val Lys Glu Leu Phe Pro Ala Pro
                180                  185                  190

Val Leu Asn Ala Ser Val Thr Ser Pro Leu Leu Glu Gly Asn Leu Val
                195                  200                  205

Thr Leu Ser Cys Glu Thr Lys Leu Leu Leu Gln Arg Pro Gly Leu Gln
210                  215                  220

Leu Tyr Phe Ser Phe Tyr Met Gly Ser Lys Thr Leu Arg Gly Arg Asn
225                  230                  235                  240

Thr Ser Ser Glu Tyr Gln Ile Leu Thr Ala Arg Arg Glu Asp Ser Gly
                245                  250                  255

Leu Tyr Trp Cys Glu Ala Ala Thr Glu Asp Gly Asn Val Leu Lys Arg
                260                  265                  270

Ser Pro Glu Leu Glu Leu Gln Val Leu Gly Leu Gln Leu Pro Thr Pro
                275                  280                  285

Val Trp Phe His Val Leu Phe Tyr Leu Ala Val Gly Ile Met Phe Leu
                290                  295                  300

Val Asn Thr Val Leu Trp Val Thr Ile Arg Lys Glu Leu Lys Arg Lys
305                  310                  315                  320

Lys Lys Trp Asp Leu Glu Ile Ser Leu Asp Ser Gly His Glu Lys Lys
                325                  330                  335

Val Ile Ser Ser Leu Gln Glu Asp Arg His Leu Glu Glu Glu Leu Lys
                340                  345                  350

Cys Gln Glu Gln Lys Glu Gln Leu Gln Glu Gly Val His Arg Lys
                355                  360                  365

Glu Pro Gln Gly Ala Thr
                370

<210> SEQ ID NO 15
<211> LENGTH: 834
<212> TYPE: DNA
<213> ORGANISM: Homo sapiens

<400> SEQUENCE: 15
gatgccctga ctctgcgatg tcagggatgg aagaatacac cactgtctca ggtgaagttc      60
tacagagatg gaaaattcct tcatttctct aaggaaaacc agactctgtc catgggagca     120
gcaacagtgc agagccgtgg ccagtacagc tgctctgggc aggtgatgta tattccacag     180
acattcacac aaacttcaga gactgccatg gttcaagtcc aagagctgtt tccacctcct     240
gtgctgagtg ccatcccctc tcctgagccc cgagagggta gcctggtgac cctgagatgt     300
```

```
cagacaaagc tgcaccccct gaggtcagcc ttgaggctcc ttttctcctt ccacaaggac    360
ggccacacct tgcaggacag gggccctcac ccagaactct gcatcccggg agccaaggag    420
ggagactctg gctttactg tgtgaggtg ccccctgagg tggccaggt ccagaagcag       480 agcccccagc tggaggtcag agtgcaggct cctgtatccc gtcctgtgct cactctgcac    540
cacgggcctg ctgaccctgc tgtggggac atggtgcagc tcctctgtga ggcacagagg     600
ggctcccctc cgatcctgta ttccttctac cttgatgaga agattgtggg gaaccactca    660
gctccctgtg gtggaaccac ctccctcctc ttcccagtga agtcagaaca ggatgctggg    720
aactactcct gcgaggctga aacagtgtc tccagagaga ggagtgagcc caagaagctg     780
tctctgaagg gttctcaagt cttgttcact cccgccagca actggctggt tcct          834

<210> SEQ ID NO 16
<211> LENGTH: 60
<212> TYPE: DNA
<213> ORGANISM: Homo sapiens

<400> SEQUENCE: 16
tggcttcctg cgagcctgct tggcctgatg gttattgctg ctgcacttct ggtttatgtg     60

<210> SEQ ID NO 17
<211> LENGTH: 135
<212> TYPE: DNA
<213> ORGANISM: Homo sapiens

<400> SEQUENCE: 17
agatcctgga gaaaagctgt gcatcaccag aaagggaaag atgaaggtgt tgtctactct     60
gtggtgcata gaacctcaaa gaggagtgaa ggacagttct atcatctgtg cggaggtgag    120
atgcctgcag cccag                                                     135

<210> SEQ ID NO 18
<211> LENGTH: 162
<212> TYPE: DNA
<213> ORGANISM: Homo sapiens

<400> SEQUENCE: 18
ggagatgccc tgactctgcg atgtcaggga tggaagaata caccactgtc tcaggtgaag     60
ttctacagag atggaaaatt ccttcatttc tctaaggaaa accagactct gtccatggga    120
gcagcaacag tgcagagccg tggccagtac agctgctctg gg                       162

<210> SEQ ID NO 19
<211> LENGTH: 174
<212> TYPE: DNA
<213> ORGANISM: Homo sapiens

<400> SEQUENCE: 19
ggtagcctgg tgaccctgag atgtcagaca aagctgcacc ccctgaggtc agccttgagg     60
ctccttttct ccttccacaa ggacggccac accttgcagg acaggggccc tcacccagaa    120
ctctgcatcc cggagccaa ggagggagac tctgggcttt actggtgtga ggtg            174

<210> SEQ ID NO 20
<211> LENGTH: 174
<212> TYPE: DNA
<213> ORGANISM: Homo sapiens

<400> SEQUENCE: 20
```

```
ggggacatgg tgcagctcct ctgtgaggca cagaggggct cccctccgat cctgtattcc      60
ttctaccttg atgagaagat tgtggggaac cactcagctc cctgtggtgg aaccacctcc     120
ctcctcttcc cagtgaagtc agaacaggat gctgggaact actcctgcga ggct           174

<210> SEQ ID NO 21
<211> LENGTH: 81
<212> TYPE: DNA
<213> ORGANISM: Homo sapiens

<400> SEQUENCE: 21
atgttgccat ctttagttcc ctgtgttggg aaaactgtct ggctgtacct ccaagcctgg      60
ccaaaccctg tgtttgaagg a                                               81

<210> SEQ ID NO 22
<211> LENGTH: 1872
<212> TYPE: DNA
<213> ORGANISM: Homo sapiens

<400> SEQUENCE: 22
gtcgacccac gcgtccgcaa ctcaggagat ctgttggaaa gagaacgata gaggaaaata      60
tatgaatgtt gccatcttta gttccctgtg ttgggaaaac tgtctggctg tacctccaag     120
cctggccaaa ccctgtgttt gaaggagatg ccctgactct gcgatgtcag ggatggaaga     180
atacaccact gtctcaggtg aagttctaca gagatggaaa attccttcat ttctctaagg     240
aaaaccagac tctgtccatg ggagcagcaa cagtgcagag ccgtggccag tacagctgct     300
ctgggcaggc gatgtatatt ccacagacat tcacacaaac ttcagagact gccatggttc     360
aagtccaaga gctgttttcca cctcctgtgc tgagtgccat cccctctcct gagccccgag     420
agggtagcct ggtgaccctg agatgtcaga caaagctgca cccctgagg tcagccttga     480 ggctcctttt ctccttccac aaggacggcc acaccttgca ggacaggggc cctcacccag     540
aactctgcat cccgggagcc aaggagggag actctgggct ttactggtgt gaggtggccc     600
ctgagggtgg ccaggtccag aagcagagcc cccagctgga ggtcagagtg caggctcctg     660
tatcccgtcc tgtgctcact ctgcaccacg ggcctgctga ccctgctgtg ggggacatgg     720
tgcagctcct ctgtgaggca cagaggggct cccctccgat cctgtattcc ttctaccttg     780
atgagaagat tgtggggaac cactcagctc cctgtggtgg aaccacctcc ctcctcttcc     840
cagtgaagtc agaacaggat gctgggaact actcctgcga ggctgagaac agtgtctcca     900
gagagaggag tgagcccaag aagctgtctc tgaagggttc tcaagtcttg ttcactcccg     960
ccagcaactg gctggttcct tggcttcctg cgagcctgct tggcctgatg gttattgctg    1020
ctgcacttct ggtttatgtg agatcctgga gaaaagctgt gcatcaccag aaagggaaag    1080
atgaaggtgt tgtctactct gtggtgcata gaacctcaaa gaggagtgaa ggacagttct    1140
atcatctgtg cggaggtgag atgcctgcag cccagtgagg tttcatccac ggaggtgaat    1200
atgagaagca ggactctcca agaaccccctt agcgactgtg aggaggttct ctgctagtga    1260
tggtgttctc ctatcaacac acgcccaccc ccagtctcca gtgctcctca ggaagacagt    1320
ggggtcctca actctttctg tgggtccttc agttcccaag cccagcatca cagagccccc    1380
tgagcccttg tcctggtcag gagcacctga accctgggtt cttttcttag cagaagacca    1440
accaatggaa tgggaaggga gatgctccca ccaacacaca cacttaggtt caatcagtga    1500
cactggacac ataagccaca gatgtcttct ttccatacaa gcatgttagt tcgcccaat    1560 atacatatat atatgaaata gtcatgtgcc gcataacaac atttcagtca gtgatagact    1620
```

```
gcatacacaa cagtggtccc ataagactgt aatggagttt aaaaattcct acgcctagtg    1680
atatcatagt tgccttaaca tcataacaca acacatttct cacgcgtttg tggtgatgct    1740
ggtacaaaca agctacagcg ccgctagtca tatacaaata tagcacatac aattatgtac    1800
agtacactat acttgataat gataataaac aactatgtta ctggtttatg taaaaaaaaa    1860
aaaaaaaaaa aa                                                         1872

<210> SEQ ID NO 23
<211> LENGTH: 1872
<212> TYPE: DNA
<213> ORGANISM: Homo sapiens

<400> SEQUENCE: 23
gtcgacccac gcgtccgcaa ctcaggagat ctgttggaaa gagaacgata gaggaaaata      60
tatgaatgtt gccatcttta gttccctgtg ttgggaaaac tgtctggctg tacctccaag     120
cctggccaaa ccctgtgttt gaaggagatg ccctgactct gcgatgtcag ggatggaaga     180
atacaccact gtctcaggtg aagttctaca gagatggaaa attccttcat ttctctaagg     240
aaaaccagac tctgtccatg ggagcagcaa cagtgcagag ccgtggccag tacagctgct     300
ctgggcaggt gatgtatctt ccacagacat tcacacaaac ttcagagact gccatggttc     360
aagtccaaga gctgtttcca cctcctgtgc tgagtgccat ccctctcct gagccccgag      420 agggtagcct ggtgaccctg agatgtcaga caaagctgca cccctgagg tcagccttga      480 ggctcctttt ctccttccac aaggacggcc acaccttgca ggacagggc cctcacccag      540 aactctgcat cccgggagcc aaggaggag actctgggct ttactggtgt gaggtggccc      600
ctgagggtgg ccaggtccag aagcagagcc cccagctgga ggtcagagtg caggctcctg     660
tatcccgtcc tgtgctcact ctgcaccacg ggcctgctga ccctgctgtg ggggacatgg     720
tgcagctcct ctgtgaggca cagagggct cccctccgat cctgtattcc ttctaccttg      780
atgagaagat tgtggggaac cactcagctc cctgtggtgg aaccacctcc ctcctcttcc     840
cagtgaagtc agaacaggat gctgggaact actcctgcga ggctgagaac agtgtctcca     900
gagagaggag tgagcccaag aagctgtctc tgaagggttc tcaagtcttg ttcactcccg     960
ccagcaactg gctggttcct tggcttcctg cgagcctgct tggcctgatg ttattgctg     1020 ctgcacttct ggtttatgtg agatcctgga gaaaagctgt gcatcaccag aaagggaaag    1080
atgaaggtgt tgtctactct gtggtgcata gaacctcaaa gaggagtgaa ggacagttct    1140
atcatctgtg cggaggtgag atgcctgcag cccagtgagg tttcatccac ggaggtgaat    1200
atgagaagca ggactctcca agaacccctt agcgactgtg aggaggttct ctgctagtga    1260
tggtgttctc ctatcaacac acgcccaccc ccagtctcca gtgctcctca ggaagacagt    1320
ggggtcctca actctttctg tgggtccttc agttcccaag cccagcatca cagagccccc    1380
tgagcccttg tcctggtcag gagcacctga accctgggtt ctttttcttag cagaagacca    1440 accaatggaa tgggaaggga gatgctccca ccaacacaca cacttaggtt caatcagtga    1500
cactggacac ataagccaca gatgtcttct ttccatacaa gcatgttagt tcgccccaat    1560
atacatatat atatgaaata gtcatgtgcc gcataacaac atttcagtca gtgatagact    1620
gcatacacaa cagtggtccc ataagactgt aatggagttt aaaaattcct acgcctagtg    1680
atatcatagt tgccttaaca tcataacaca acacatttct cacgcgtttg tggtgatgct    1740
ggtacaaaca agctacagcg ccgctagtca tatacaaata tagcacatac aattatgtac    1800
```

-continued

| agtacactat acttgataat gataataaac aactatgtta ctggtttatg taaaaaaaaa | 1860 |
| aaaaaaaaaa aa | 1872 |

<210> SEQ ID NO 24
<211> LENGTH: 1872
<212> TYPE: DNA
<213> ORGANISM: Homo sapiens

<400> SEQUENCE: 24

| gtcgacccac gcgtccgcaa ctcaggagat ctgttggaaa gagaacgata gaggaaaata | 60 |
| tatgaatgtt gccatcttta gttccctgtg ttgggaaaac tgtctggctg tacctccaag | 120 |
| cctggccaaa ccctgtgttt gaaggagatg ccctgactct gcgatgtcag ggatggaaga | 180 |
| atacaccact gtctcaggtg aagttctaca gagatgaaa attccttcat ttctctaagg | 240 |
| aaaaccagac tctgtccatg ggagcagcaa cagtgcagag ccgtggccag tacagctgct | 300 |
| ctgggcaggt gatgtatatt ccacagacat tcacacaaac ttcagagact gccatggttc | 360 |
| aagtccaaga gctgtttcca cctcctgtgc tgagtgccat cccctctcct gagccccgag | 420 |
| agggtagcct ggtgaccctg agatgtcaga caaagctgca cccctgagg tcagccttga | 480 |
| ggctcctttt ctccttccac aaggacggcc acaccttgca ggacagggc cctcacccag | 540 |
| aactctgcat cccgggagcc aaggaggag actctgggct ttactggtgt gaggtggccc | 600 |
| ctgagggtgg ccaggtccag aagcagagcc cccagctgga ggtcagagtg caggttcctg | 660 |
| tatcccgtcc tgtgctcact ctgcaccacg ggcctgctga ccctgctgtg ggggacatgg | 720 |
| tgcagctcct ctgtgaggca cagaggggct cccctccgat cctgtattcc ttctaccttg | 780 |
| atgagaagat tgtggggaac cactcagctc cctgtggtgg aaccacctcc ctcctcttcc | 840 |
| cagtgaagtc agaacaggat gctgggaact actcctgcga ggctgagaac agtgtctcca | 900 |
| gagagaggag tgagcccaag aagctgtctc tgaagggttc tcaagtcttg ttcactcccg | 960 |
| ccagcaactg gctggttcct tggcttcctg cgagcctgct tggcctgatg gttattgctg | 1020 |
| ctgcacttct ggtttatgtg agatcctgga gaaaagctgt gcatcaccag aaagggaaag | 1080 |
| atgaaggtgt tgtctactct gtggtgcata gaacctcaaa gaggagtgaa ggacagttct | 1140 |
| atcatctgtg cggaggtgag atgcctgcag cccagtgagg tttcatccac ggaggtgaat | 1200 |
| atgagaagca ggactctcca agaaccccctt agcgactgtg aggaggttct ctgctagtga | 1260 |
| tggtgttctc ctatcaacac acgcccaccc ccagtctcca gtgctcctca ggaagacagt | 1320 |
| ggggtcctca actctttctg tgggtccttc agttcccaag cccagcatca cagagccccc | 1380 |
| tgagcccttg tcctggtcag gagcacctga accctgggtt cttttcttag cagaagacca | 1440 |
| accaatggaa tgggaaggga gatgctccca ccaacacaca cacttaggtt caatcagtga | 1500 |
| cactggacac ataagccaca gatgtcttct ttccatacaa gcatgttagt tcgccccaat | 1560 |
| atacatatat atatgaaata gtcatgtgcc gcataacaac atttcagtca gtgatagact | 1620 |
| gcatacacaa cagtggtccc ataagactgt aatggagttt aaaaattcct acgcctagtg | 1680 |
| atatcatagt tgccttaaca tcataacaca acacatttct cacgcgtttg tggtgatgct | 1740 |
| ggtacaaaca agctacagcg ccgctagtca tatacaaata tagcacatac aattatgtac | 1800 |
| agtacactat acttgataat gataataaac aactatgtta ctggtttatg taaaaaaaaa | 1860 |
| aaaaaaaaaa aa | 1872 |

<210> SEQ ID NO 25
<211> LENGTH: 1872

<212> TYPE: DNA
<213> ORGANISM: Homo sapiens

<400> SEQUENCE: 25

```
gtcgacccac gcgtccgcaa ctcaggagat ctgttggaaa gagaacgata gaggaaaata      60
tatgaatgtt gccatcttta gttccctgtg ttgggaaaac tgtctggctg tacctccaag     120
cctggccaaa ccctgtgttt gaaggagatg ccctgactct gcgatgtcag ggatggaaga     180
atacaccact gtctcaggtg aagttctaca gagatggaaa attccttcat ttctctaagg     240
aaaaccagac tctgtccatg ggagcagcaa cagtgcagag ccgtggccag tacagctgct     300
ctgggcaggt gatgtatatt ccacagacat tcacacaaac ttcagagact gccatggttc     360
aagtccaaga gctgtttcca cctcctgtgc tgagtgccat ccctctcct gagccccgag      420
agggtagcct ggtgaccctg agatgtcaga caaagctgca ccccctgagg tcagccttga     480
ggctcctttt ctccttccac aaggacggcc acaccttgca ggacagggc cctcacccag      540
aactctgcat cccgggagcc aaggagggag actctgggct ttactggtgt gaggtggccc     600
ctgagggtgg ccaggtccag aagcagagcc cccagctgga ggtcagagtg caggctcctg     660
tatcccgtcc tgcgctcact ctgcaccacg ggcctgctga ccctgctgtg ggggacatgg     720
tgcagctcct ctgtgaggca cagagggct ccctccgat cctgtattcc ttctaccttg       780
atgagaagat tgtggggaac cactcagctc cctgtggtgg aaccacctcc ctcctcttcc     840
cagtgaagtc agaacaggat gctgggaact actcctgcga ggctgagaac agtgtctcca     900
gagagaggag tgagcccaag aagctgtctc tgaagggttc tcaagtcttg ttcactcccg     960
ccagcaactg gctggttcct tggcttcctg cgagcctgct tggcctgatg gttattgctg    1020
ctgcacttct ggtttatgtg agatcctgga gaaaagctgt gcatcaccag aaagggaaag    1080
atgaaggtgt tgtctactct gtggtgcata gaacctcaaa gaggagtgaa ggacagttct    1140
atcatctgtg cggaggtgag atgcctgcag cccagtgagg tttcatccac ggaggtgaat    1200
atgagaagca ggactctcca agaaccccctt agcgactgtg aggaggttct ctgctagtga    1260
tggtgttctc ctatcaacac acgcccaccc ccagtctcca gtgctcctca ggaagacagt    1320
ggggtcctca actctttctg tgggtccttc agttcccaag cccagcatca cagagccccc    1380
tgagcccttg tcctggtcag gagcacctga accctgggtt cttttcttag cagaagacca    1440
accaatggaa tgggaaggga gatgctccca ccaacacaca cacttaggtt caatcagtga    1500
cactggacac ataagccaca gatgtcttct ttccatacaa gcatgttagt tcgcccaat    1560
atacatatat atatgaaata gtcatgtgcc gcataacaac atttcagtca gtgatagact    1620
gcatacacaa cagtggtccc ataagactgt aatggagttt aaaaattcct acgcctagtg    1680
atatcatagt tgccttaaca tcataacaca acacatttct cacgcgtttg tggtgatgct    1740
ggtacaaaca agctacagcg ccgctagtca tatacaaata tagcacatac aattatgtac    1800
agtacactat acttgataat gataataaac aactatgtta ctggtttatg taaaaaaaaa    1860
aaaaaaaaa aa                                                          1872
```

<210> SEQ ID NO 26
<211> LENGTH: 1110
<212> TYPE: DNA
<213> ORGANISM: Homo sapiens

<400> SEQUENCE: 26

```
atgttgccat ctttagttcc ctgtgttggg aaaactgtct ggctgtacct ccaagcctgg      60
```

-continued

| | |
|---|---|
| ccaaaccctg tgtttgaagg agatgccctg actctgcgat gtcagggatg gaagaataca | 120 |
| ccactgtctc aggtgaagtt ctacagagat ggaaaattcc ttcatttctc taaggaaaac | 180 |
| cagactctgt ccatgggagc agcaacagtg cagagccgtg gccagtacag ctgctctggg | 240 |
| caggcgatgt atattccaca gacattcaca caaacttcag agactgccat ggttcaagtc | 300 |
| caagagctgt ttccacctcc tgtgctgagt gccatcccct ctcctgagcc ccgagagggt | 360 |
| agcctggtga ccctgagatg tcagacaaag ctgcaccccc tgaggtcagc cttgaggctc | 420 |
| cttttctcct tccacaagga cggccacacc ttgcaggaca ggggccctca cccagaactc | 480 |
| tgcatcccgg gagccaagga gggagactct gggctttact ggtgtgaggt ggcccctgag | 540 |
| ggtggccagg tccagaagca gagcccccag ctggaggtca gagtgcaggc tcctgtatcc | 600 |
| cgtcctgtgc tcactctgca ccacgggcct gctgaccctg ctgtggggga catggtgcag | 660 |
| ctcctctgtg aggcacagag gggctcccct ccgatcctgt attccttcta ccttgatgag | 720 |
| aagattgtgg ggaaccactc agctcccgtg gtggaaccac ctccctcct cttcccagtg | 780 |
| aagtcagaac aggatgctgg gaactactcc tgcgaggctg agaacagtgt ctccagagag | 840 |
| aggagtgagc ccagaagct gtctctgaag ggttctcaag tcttgttcac tcccgccagc | 900 |
| aactggctgg ttccttggct tcctgcgagc ctgcttggcc tgatggttat tgctgctgca | 960 |
| cttctggttt atgtgagatc ctggagaaaa gctgtgcatc accagaaagg gaaagatgaa | 1020 |
| ggtgttgtct actctgtggt gcatagaacc tcaaagagga gtgaaggaca gttctatcat | 1080 |
| ctgtgcggag gtgagatgcc tgcagcccag | 1110 |

<210> SEQ ID NO 27
<211> LENGTH: 1110
<212> TYPE: DNA
<213> ORGANISM: Homo sapiens

<400> SEQUENCE: 27

| | |
|---|---|
| atgttgccat ctttagttcc ctgtgttggg aaaactgtct ggctgtacct ccaagcctgg | 60 |
| ccaaaccctg tgtttgaagg agatgccctg actctgcgat gtcagggatg gaagaataca | 120 |
| ccactgtctc aggtgaagtt ctacagagat ggaaaattcc ttcatttctc taaggaaaac | 180 |
| cagactctgt ccatgggagc agcaacagtg cagagccgtg gccagtacag ctgctctggg | 240 |
| caggtgatgt atcttccaca gacattcaca caaacttcag agactgccat ggttcaagtc | 300 |
| caagagctgt ttccacctcc tgtgctgagt gccatcccct ctcctgagcc ccgagagggt | 360 |
| agcctggtga ccctgagatg tcagacaaag ctgcaccccc tgaggtcagc cttgaggctc | 420 |
| cttttctcct tccacaagga cggccacacc ttgcaggaca ggggccctca cccagaactc | 480 |
| tgcatcccgg gagccaagga gggagactct gggctttact ggtgtgaggt ggcccctgag | 540 |
| ggtggccagg tccagaagca gagcccccag ctggaggtca gagtgcaggc tcctgtatcc | 600 |
| cgtcctgtgc tcactctgca ccacgggcct gctgaccctg ctgtggggga catggtgcag | 660 |
| ctcctctgtg aggcacagag gggctcccct ccgatcctgt attccttcta ccttgatgag | 720 |
| aagattgtgg ggaaccactc agctcccgtg gtggaaccac ctccctcct cttcccagtg | 780 |
| aagtcagaac aggatgctgg gaactactcc tgcgaggctg agaacagtgt ctccagagag | 840 |
| aggagtgagc ccagaagct gtctctgaag ggttctcaag tcttgttcac tcccgccagc | 900 |
| aactggctgg ttccttggct tcctgcgagc ctgcttggcc tgatggttat tgctgctgca | 960 |
| cttctggttt atgtgagatc ctggagaaaa gctgtgcatc accagaaagg gaaagatgaa | 1020 |
| ggtgttgtct actctgtggt gcatagaacc tcaaagagga gtgaaggaca gttctatcat | 1080 |

```
ctgtgcggag gtgagatgcc tgcagcccag                                     1110

<210> SEQ ID NO 28
<211> LENGTH: 1110
<212> TYPE: DNA
<213> ORGANISM: Homo sapiens

<400> SEQUENCE: 28
atgttgccat ctttagttcc ctgtgttggg aaaactgtct ggctgtacct ccaagcctgg      60
ccaaaccctg tgtttgaagg agatgccctg actctgcgat gtcagggatg gaagaataca     120
ccactgtctc aggtgaagtt ctacagagat ggaaaattcc ttcatttctc taaggaaaac     180
cagactctgt ccatgggagc agcaacagtg cagagccgtg gccagtacag ctgctctggg     240
caggtgatgt atattccaca gacattcaca caaacttcag agactgccat ggttcaagtc     300
caagagctgt ttccacctcc tgtgctgagt gccatcccct ctcctgagcc ccgagagggt     360
agcctggtga ccctgagatg tcagacaaag ctgcaccccc tgaggtcagc cttgaggctc     420
cttttctcct tccacaagga cggccacacc ttgcaggaca ggggccctca cccagaactc     480
tgcatcccgg agccaaggag gggagactct gggctttact ggtgtgaggt ggcccctgag     540
ggtggccagg tccagaagca gagccccag ctggaggtca gagtgcaggt tcctgtatcc      600
cgtcctgtgc tcactctgca ccacgggcct gctgaccctg ctgtggggga catggtgcag     660
ctcctctgtg aggcacagag gggctcccct ccgatcctgt attccttcta ccttgatgag     720
aagattgtgg ggaaccactc agctccctgt ggtggaacca cctccctcct cttcccagtg     780
aagtcagaac aggatgctgg gaactactcc tgcgaggctg agaacagtgt ctccagagag     840
aggagtgagc ccaagaagct gtctctgaag ggttctcaag tcttgttcac tcccgccagc     900
aactggctgg ttccttggct tcctgcgagc ctgcttggcc tgatggttat tgctgctgca     960
cttctggttt atgtgagatc ctggagaaaa gctgtgcatc accagaaagg gaaagatgaa    1020
ggtgttgtct actctgtggt gcatagaacc tcaaagagga gtgaaggaca gttctatcat    1080
ctgtgcggag gtgagatgcc tgcagcccag                                    1110

<210> SEQ ID NO 29
<211> LENGTH: 1110
<212> TYPE: DNA
<213> ORGANISM: Homo sapiens

<400> SEQUENCE: 29
atgttgccat ctttagttcc ctgtgttggg aaaactgtct ggctgtacct ccaagcctgg      60
ccaaaccctg tgtttgaagg agatgccctg actctgcgat gtcagggatg gaagaataca     120
ccactgtctc aggtgaagtt ctacagagat ggaaaattcc ttcatttctc taaggaaaac     180
cagactctgt ccatgggagc agcaacagtg cagagccgtg gccagtacag ctgctctggg     240
caggtgatgt atattccaca gacattcaca caaacttcag agactgccat ggttcaagtc     300
caagagctgt ttccacctcc tgtgctgagt gccatcccct ctcctgagcc ccgagagggt     360
agcctggtga ccctgagatg tcagacaaag ctgcaccccc tgaggtcagc cttgaggctc     420
cttttctcct tccacaagga cggccacacc ttgcaggaca ggggccctca cccagaactc     480
tgcatcccgg agccaaggag gggagactct gggctttact ggtgtgaggt ggcccctgag     540
ggtggccagg tccagaagca gagccccag ctggaggtca gagtgcaggc tcctgtatcc      600
cgtcctgcgc tcactctgca ccacgggcct gctgaccctg ctgtggggga catggtgcag     660
```

-continued

```
ctcctctgtg aggcacagag gggctcccct ccgatcctgt attccttcta ccttgatgag      720
aagattgtgg ggaaccactc agctccctgt ggtggaacca cctccctcct cttcccagtg      780
aagtcagaac aggatgctgg gaactactcc tgcgaggctg agaacagtgt ctccagagag      840
aggagtgagc ccaagaagct gtctctgaag ggttctcaag tcttgttcac tcccgccagc      900
aactggctgg ttccttggct tcctgcgagc ctgcttggcc tgatggttat tgctgctgca      960
cttctggttt atgtgagatc ctggagaaaa gctgtgcatc accagaaagg gaaagatgaa     1020
ggtgttgtct actctgtggt gcatagaacc tcaaagagga gtgaaggaca gttctatcat     1080
ctgtgcggag gtgagatgcc tgcagcccag                                      1110
```

<210> SEQ ID NO 30
<211> LENGTH: 370
<212> TYPE: PRT
<213> ORGANISM: Homo sapiens

<400> SEQUENCE: 30

```
Met Leu Pro Ser Leu Val Pro Cys Val Gly Lys Thr Val Trp Leu Tyr
 1               5                  10                  15

Leu Gln Ala Trp Pro Asn Pro Val Phe Glu Gly Asp Ala Leu Thr Leu
            20                  25                  30

Arg Cys Gln Gly Trp Lys Asn Thr Pro Leu Ser Gln Val Lys Phe Tyr
        35                  40                  45

Arg Asp Gly Lys Phe Leu His Phe Ser Lys Glu Asn Gln Thr Leu Ser
    50                  55                  60

Met Gly Ala Ala Thr Val Gln Ser Arg Gly Gln Tyr Ser Cys Ser Gly
65                  70                  75                  80

Gln Ala Met Tyr Ile Pro Gln Thr Phe Thr Gln Thr Ser Glu Thr Ala
                85                  90                  95

Met Val Gln Val Gln Glu Leu Phe Pro Pro Val Leu Ser Ala Ile
            100                 105                 110

Pro Ser Pro Glu Pro Arg Glu Gly Ser Leu Val Thr Leu Arg Cys Gln
        115                 120                 125

Thr Lys Leu His Pro Leu Arg Ser Ala Leu Arg Leu Leu Phe Ser Phe
    130                 135                 140

His Lys Asp Gly His Thr Leu Gln Asp Arg Gly Pro His Pro Glu Leu
145                 150                 155                 160

Cys Ile Pro Gly Ala Lys Glu Gly Asp Ser Gly Leu Tyr Trp Cys Glu
                165                 170                 175

Val Ala Pro Glu Gly Gly Gln Val Gln Lys Gln Ser Pro Gln Leu Glu
            180                 185                 190

Val Arg Val Gln Ala Pro Val Ser Arg Pro Val Leu Thr Leu His His
        195                 200                 205

Gly Pro Ala Asp Pro Ala Val Gly Asp Met Val Gln Leu Leu Cys Glu
    210                 215                 220

Ala Gln Arg Gly Ser Pro Pro Ile Leu Tyr Ser Phe Tyr Leu Asp Glu
225                 230                 235                 240

Lys Ile Val Gly Asn His Ser Ala Pro Cys Gly Thr Thr Ser Leu
                245                 250                 255

Leu Phe Pro Val Lys Ser Glu Gln Asp Ala Gly Asn Tyr Ser Cys Glu
            260                 265                 270

Ala Glu Asn Ser Val Ser Arg Glu Arg Ser Glu Pro Lys Lys Leu Ser
        275                 280                 285

Leu Lys Gly Ser Gln Val Leu Phe Thr Pro Ala Ser Asn Trp Leu Val
```

```
                  290                 295                 300
Pro Trp Leu Pro Ala Ser Leu Leu Gly Leu Met Val Ile Ala Ala Ala
305                 310                 315                 320
Leu Leu Val Tyr Val Arg Ser Trp Arg Lys Ala Val His His Gln Lys
                325                 330                 335
Gly Lys Asp Glu Gly Val Val Tyr Ser Val Val His Arg Thr Ser Lys
                340                 345                 350
Arg Ser Glu Gly Gln Phe Tyr His Leu Cys Gly Glu Met Pro Ala
                355                 360                 365
Ala Gln
    370

<210> SEQ ID NO 31
<211> LENGTH: 370
<212> TYPE: PRT
<213> ORGANISM: Homo sapiens

<400> SEQUENCE: 31

Met Leu Pro Ser Leu Val Pro Cys Val Gly Lys Thr Val Trp Leu Tyr
1               5                   10                  15
Leu Gln Ala Trp Pro Asn Pro Val Phe Glu Gly Asp Ala Leu Thr Leu
                20                  25                  30
Arg Cys Gln Gly Trp Lys Asn Thr Pro Leu Ser Gln Val Lys Phe Tyr
            35                  40                  45
Arg Asp Gly Lys Phe Leu His Phe Ser Lys Glu Asn Gln Thr Leu Ser
    50                  55                  60
Met Gly Ala Ala Thr Val Gln Ser Arg Gly Gln Tyr Ser Cys Ser Gly
65                  70                  75                  80
Gln Val Met Tyr Leu Pro Gln Thr Phe Thr Gln Thr Ser Glu Thr Ala
                85                  90                  95
Met Val Gln Val Gln Glu Leu Phe Pro Pro Val Leu Ser Ala Ile
                100                 105                 110
Pro Ser Pro Glu Pro Arg Glu Gly Ser Leu Val Thr Leu Arg Cys Gln
            115                 120                 125
Thr Lys Leu His Pro Leu Arg Ser Ala Leu Arg Leu Leu Phe Ser Phe
    130                 135                 140
His Lys Asp Gly His Thr Leu Gln Asp Arg Gly Pro His Pro Glu Leu
145                 150                 155                 160
Cys Ile Pro Gly Ala Lys Glu Gly Asp Ser Gly Leu Tyr Trp Cys Glu
                165                 170                 175
Val Ala Pro Glu Gly Gly Gln Val Gln Lys Gln Ser Pro Gln Leu Glu
                180                 185                 190
Val Arg Val Gln Ala Pro Val Ser Arg Pro Val Leu Thr Leu His His
            195                 200                 205
Gly Pro Ala Asp Pro Ala Val Gly Asp Met Val Gln Leu Leu Cys Glu
    210                 215                 220
Ala Gln Arg Gly Ser Pro Pro Ile Leu Tyr Ser Phe Tyr Leu Asp Glu
225                 230                 235                 240
Lys Ile Val Gly Asn His Ser Ala Pro Cys Gly Gly Thr Thr Ser Leu
                245                 250                 255
Leu Phe Pro Val Lys Ser Glu Gln Asp Ala Gly Asn Tyr Ser Cys Glu
            260                 265                 270
Ala Glu Asn Ser Val Ser Arg Glu Arg Ser Glu Pro Lys Lys Leu Ser
    275                 280                 285
```

```
Leu Lys Gly Ser Gln Val Leu Phe Thr Pro Ala Ser Asn Trp Leu Val
    290                 295                 300
Pro Trp Leu Pro Ala Ser Leu Leu Gly Leu Met Val Ile Ala Ala Ala
305                 310                 315                 320
Leu Leu Val Tyr Val Arg Ser Trp Arg Lys Ala Val His His Gln Lys
                325                 330                 335
Gly Lys Asp Glu Gly Val Val Tyr Ser Val Val His Arg Thr Ser Lys
            340                 345                 350
Arg Ser Glu Gly Gln Phe Tyr His Leu Cys Gly Gly Glu Met Pro Ala
        355                 360                 365
Ala Gln
    370

<210> SEQ ID NO 32
<211> LENGTH: 370
<212> TYPE: PRT
<213> ORGANISM: Homo sapiens

<400> SEQUENCE: 32

Met Leu Pro Ser Leu Val Pro Cys Val Gly Lys Thr Val Trp Leu Tyr
1               5                   10                  15
Leu Gln Ala Trp Pro Asn Pro Val Phe Glu Gly Asp Ala Leu Thr Leu
            20                  25                  30
Arg Cys Gln Gly Trp Lys Asn Thr Pro Leu Ser Gln Val Lys Phe Tyr
        35                  40                  45
Arg Asp Gly Lys Phe Leu His Phe Ser Lys Glu Asn Gln Thr Leu Ser
    50                  55                  60
Met Gly Ala Ala Thr Val Gln Ser Arg Gly Gln Tyr Ser Cys Ser Gly
65                  70                  75                  80
Gln Val Met Tyr Ile Pro Gln Thr Phe Thr Gln Thr Ser Glu Thr Ala
                85                  90                  95
Met Val Gln Val Gln Glu Leu Phe Pro Pro Val Leu Ser Ala Ile
            100                 105                 110
Pro Ser Pro Glu Pro Arg Glu Gly Ser Leu Val Thr Leu Arg Cys Gln
        115                 120                 125
Thr Lys Leu His Pro Leu Arg Ser Ala Leu Arg Leu Leu Phe Ser Phe
    130                 135                 140
His Lys Asp Gly His Thr Leu Gln Asp Arg Gly Pro His Pro Glu Leu
145                 150                 155                 160
Cys Ile Pro Gly Ala Lys Glu Gly Asp Ser Gly Leu Tyr Trp Cys Glu
                165                 170                 175
Val Ala Pro Glu Gly Gly Gln Val Gln Lys Gln Ser Pro Gln Leu Glu
            180                 185                 190
Val Arg Val Gln Val Pro Val Ser Arg Pro Val Leu Thr Leu His His
        195                 200                 205
Gly Pro Ala Asp Pro Ala Val Gly Asp Met Val Gln Leu Leu Cys Glu
    210                 215                 220
Ala Gln Arg Gly Ser Pro Pro Ile Leu Tyr Ser Phe Tyr Leu Asp Glu
225                 230                 235                 240
Lys Ile Val Gly Asn His Ser Ala Pro Cys Gly Gly Thr Thr Ser Leu
                245                 250                 255
Leu Phe Pro Val Lys Ser Glu Gln Asp Ala Gly Asn Tyr Ser Cys Glu
            260                 265                 270
Ala Glu Asn Ser Val Ser Arg Glu Arg Ser Glu Pro Lys Lys Leu Ser
        275                 280                 285
```

-continued

Leu Lys Gly Ser Gln Val Leu Phe Thr Pro Ala Ser Asn Trp Leu Val
        290                 295                 300

Pro Trp Leu Pro Ala Ser Leu Gly Leu Met Val Ile Ala Ala Ala
305                 310                 315                 320

Leu Leu Val Tyr Val Arg Ser Trp Arg Lys Ala Val His His Gln Lys
                325                 330                 335

Gly Lys Asp Glu Gly Val Val Tyr Ser Val Val His Arg Thr Ser Lys
            340                 345                 350

Arg Ser Glu Gly Gln Phe Tyr His Leu Cys Gly Gly Glu Met Pro Ala
        355                 360                 365

Ala Gln
    370

<210> SEQ ID NO 33
<211> LENGTH: 370
<212> TYPE: PRT
<213> ORGANISM: Homo sapiens

<400> SEQUENCE: 33

Met Leu Pro Ser Leu Val Pro Cys Val Gly Lys Thr Val Trp Leu Tyr
1               5                   10                  15

Leu Gln Ala Trp Pro Asn Pro Val Phe Glu Gly Asp Ala Leu Thr Leu
            20                  25                  30

Arg Cys Gln Gly Trp Lys Asn Thr Pro Leu Ser Gln Val Lys Phe Tyr
        35                  40                  45

Arg Asp Gly Lys Phe Leu His Phe Ser Lys Glu Asn Gln Thr Leu Ser
    50                  55                  60

Met Gly Ala Ala Thr Val Gln Ser Arg Gly Gln Tyr Ser Cys Ser Gly
65                  70                  75                  80

Gln Val Met Tyr Ile Pro Gln Thr Phe Thr Gln Thr Ser Glu Thr Ala
                85                  90                  95

Met Val Gln Val Gln Glu Leu Phe Pro Pro Val Leu Ser Ala Ile
            100                 105                 110

Pro Ser Pro Glu Pro Arg Glu Gly Ser Leu Val Thr Leu Arg Cys Gln
        115                 120                 125

Thr Lys Leu His Pro Leu Arg Ser Ala Leu Arg Leu Leu Phe Ser Phe
    130                 135                 140

His Lys Asp Gly His Thr Leu Gln Asp Arg Gly Pro His Pro Glu Leu
145                 150                 155                 160

Cys Ile Pro Gly Ala Lys Glu Gly Asp Ser Gly Leu Tyr Trp Cys Glu
                165                 170                 175

Val Ala Pro Glu Gly Gly Gln Val Gln Lys Gln Ser Pro Gln Leu Glu
            180                 185                 190

Val Arg Val Gln Ala Pro Val Ser Arg Pro Ala Leu Thr Leu His His
        195                 200                 205

Gly Pro Ala Asp Pro Ala Val Gly Asp Met Val Gln Leu Leu Cys Glu
    210                 215                 220

Ala Gln Arg Gly Ser Pro Pro Ile Leu Tyr Ser Phe Tyr Leu Asp Glu
225                 230                 235                 240

Lys Ile Val Gly Asn His Ser Ala Pro Cys Gly Gly Thr Thr Ser Leu
                245                 250                 255

Leu Phe Pro Val Lys Ser Glu Gln Asp Ala Gly Asn Tyr Ser Cys Glu
            260                 265                 270

Ala Glu Asn Ser Val Ser Arg Glu Arg Ser Glu Pro Lys Lys Leu Ser

```
                  275                 280                 285
Leu Lys Gly Ser Gln Val Leu Phe Thr Pro Ala Ser Asn Trp Leu Val
    290                 295                 300

Pro Trp Leu Pro Ala Ser Leu Leu Gly Leu Met Val Ile Ala Ala Ala
305                 310                 315                 320

Leu Leu Val Tyr Val Arg Ser Trp Arg Lys Ala Val His Gln Lys
                325                 330                 335

Gly Lys Asp Glu Gly Val Val Tyr Ser Val Val His Arg Thr Ser Lys
                340                 345                 350

Arg Ser Glu Gly Gln Phe Tyr His Leu Cys Gly Glu Met Pro Ala
                355                 360                 365

Ala Gln
    370

<210> SEQ ID NO 34
<211> LENGTH: 305
<212> TYPE: PRT
<213> ORGANISM: Homo sapiens

<400> SEQUENCE: 34

Met Leu Pro Ser Leu Val Pro Cys Val Gly Lys Thr Val Trp Leu Tyr
1               5                   10                  15

Leu Gln Ala Trp Pro Asn Pro Val Phe Glu Gly Asp Ala Leu Thr Leu
                20                  25                  30

Arg Cys Gln Gly Trp Lys Asn Thr Pro Leu Ser Gln Val Lys Phe Tyr
            35                  40                  45

Arg Asp Gly Lys Phe Leu His Phe Ser Lys Glu Asn Gln Thr Leu Ser
    50                  55                  60

Met Gly Ala Ala Thr Val Gln Ser Arg Gly Gln Tyr Ser Cys Ser Gly
65                  70                  75                  80

Gln Val Met Tyr Ile Pro Gln Thr Phe Thr Gln Thr Ser Glu Thr Ala
                85                  90                  95

Met Val Gln Val Gln Glu Leu Phe Pro Pro Val Leu Ser Ala Ile
                100                 105                 110

Pro Ser Pro Glu Pro Arg Glu Gly Ser Leu Val Thr Leu Arg Cys Gln
    115                 120                 125

Thr Lys Leu His Pro Leu Arg Ser Ala Leu Arg Leu Leu Phe Ser Phe
    130                 135                 140

His Lys Asp Gly His Thr Leu Gln Asp Arg Gly Pro His Pro Glu Leu
145                 150                 155                 160

Cys Ile Pro Gly Ala Lys Glu Gly Asp Ser Gly Leu Tyr Trp Cys Glu
                165                 170                 175

Val Ala Pro Glu Gly Gly Gln Val Gln Lys Gln Ser Pro Gln Leu Glu
                180                 185                 190

Val Arg Val Gln Ala Pro Val Ser Arg Pro Val Leu Thr Leu His His
            195                 200                 205

Gly Pro Ala Asp Pro Ala Val Gly Asp Met Val Gln Leu Leu Cys Glu
    210                 215                 220

Ala Gln Arg Gly Ser Pro Pro Ile Leu Tyr Ser Phe Tyr Leu Asp Glu
225                 230                 235                 240

Lys Ile Val Gly Asn His Ser Ala Pro Cys Gly Thr Thr Ser Leu
                245                 250                 255

Leu Phe Pro Val Lys Ser Glu Gln Asp Ala Gly Asn Tyr Ser Cys Glu
                260                 265                 270
```

```
Ala Glu Asn Ser Val Ser Arg Glu Arg Ser Glu Pro Lys Lys Leu Ser
            275                 280                 285

Leu Lys Gly Ser Gln Val Leu Phe Thr Pro Ala Ser Asn Trp Leu Val
        290                 295                 300

Pro
305

<210> SEQ ID NO 35
<211> LENGTH: 20
<212> TYPE: DNA
<213> ORGANISM: Artificial Sequence
<220> FEATURE:
<223> OTHER INFORMATION: forward primer

<400> SEQUENCE: 35
ctccaagaac cccttagcga                                                  20

<210> SEQ ID NO 36
<211> LENGTH: 20
<212> TYPE: DNA
<213> ORGANISM: Artificial Sequence
<220> FEATURE:
<223> OTHER INFORMATION: reverse primer

<400> SEQUENCE: 36
ggtgggcgtg tgttgatagg                                                  20

<210> SEQ ID NO 37
<211> LENGTH: 32
<212> TYPE: DNA
<213> ORGANISM: Artificial Sequence
<220> FEATURE:
<223> OTHER INFORMATION: TaqMan prober

<400> SEQUENCE: 37
ctgtgaggag gttctctgct agtgatggtg tt                                    32

<210> SEQ ID NO 38
<211> LENGTH: 21
<212> TYPE: DNA
<213> ORGANISM: Artificial Sequence
<220> FEATURE:
<223> OTHER INFORMATION: forward primer

<400> SEQUENCE: 38
cacccccact gaaaaagatg a                                                21

<210> SEQ ID NO 39
<211> LENGTH: 26
<212> TYPE: DNA
<213> ORGANISM: Artificial Sequence
<220> FEATURE:
<223> OTHER INFORMATION: reverse primer

<400> SEQUENCE: 39
cttaactatc ttgggctgtg acaaag                                           26

<210> SEQ ID NO 40
<211> LENGTH: 23
<212> TYPE: DNA
<213> ORGANISM: Artificial Sequence
<220> FEATURE:
<223> OTHER INFORMATION: TaqMan probe

<400> SEQUENCE: 40
```

```
atgcctgccg tgtgaaccac gtg                                              23
```

<210> SEQ ID NO 41
<211> LENGTH: 315
<212> TYPE: PRT
<213> ORGANISM: Homo sapiens

<400> SEQUENCE: 41

```
Met Glu Thr Gln Met Ser Gln Asn Val Cys Pro Arg Asn Leu Trp Leu
 1               5                  10                  15

Leu Gln Pro Leu Thr Val Leu Leu Leu Ala Ser Ala Asp Ser Gln
                20                  25                  30

Ala Ala Pro Pro Lys Ala Val Lys Leu Glu Pro Pro Trp Ile
            35                  40                  45

Asn Val Leu Gln Glu Asp Ser Val Thr Leu Thr Cys Gln Gly Ala Arg
 50                  55                  60

Ser Pro Glu Ser Asp Ser Ile Gln Trp Phe His Asn Gly Asn Leu Ile
65                   70                  75                  80

Pro Thr His Thr Gln Pro Ser Tyr Arg Phe Lys Ala Asn Asn Asn Asp
                85                  90                  95

Ser Gly Glu Tyr Thr Cys Gln Thr Gly Gln Thr Ser Leu Ser Asp Pro
            100                 105                 110

Val His Leu Thr Val Leu Ser Glu Trp Leu Val Leu Gln Thr Pro His
        115                 120                 125

Leu Glu Phe Gln Glu Gly Glu Thr Ile Met Leu Arg Cys His Ser Trp
    130                 135                 140

Lys Asp Lys Pro Leu Val Lys Val Thr Phe Phe Gln Asn Gly Lys Ser
145                 150                 155                 160

Gln Lys Phe Ser Arg Leu Asp Pro Thr Phe Ser Ile Pro Gln Ala Asn
                165                 170                 175

His Ser His Ser Gly Asp Tyr His Cys Thr Gly Asn Ile Gly Tyr Thr
            180                 185                 190

Leu Phe Ser Ser Lys Pro Val Thr Ile Thr Val Gln Val Pro Ser Met
        195                 200                 205

Gly Ser Ser Pro Met Gly Ile Ile Val Ala Val Val Ile Ala Thr
    210                 215                 220

Ala Val Ala Ala Ile Val Ala Ala Val Val Ala Leu Ile Tyr Cys Arg
225                 230                 235                 240

Lys Lys Arg Ile Ser Ala Asn Ser Thr Asp Pro Val Lys Ala Ala Gln
                245                 250                 255

Phe Glu Pro Pro Gly Arg Gln Met Ile Ala Ile Arg Lys Arg Gln Leu
            260                 265                 270

Glu Glu Thr Asn Asn Asp Tyr Glu Thr Ala Asp Gly Gly Tyr Met Thr
        275                 280                 285

Leu Asn Pro Arg Ala Pro Thr Asp Asp Lys Asn Ile Tyr Leu Thr
    290                 295                 300

Leu Pro Pro Asn Asp His Val Asn Ser Asn
305                 310                 315
```

<210> SEQ ID NO 42
<211> LENGTH: 310
<212> TYPE: PRT
<213> ORGANISM: Homo sapiens

<400> SEQUENCE: 42

```
Met Gly Ile Leu Ser Phe Leu Pro Val Leu Ala Thr Glu Ser Asp Trp
```

```
                1               5                  10                  15
Ala Asp Cys Lys Ser Pro Gln Pro Trp Gly His Met Leu Leu Trp Thr
                    20                  25                  30

Ala Val Leu Phe Leu Ala Pro Val Ala Gly Thr Pro Ala Ala Pro Pro
                    35                  40                  45

Lys Ala Val Leu Lys Leu Glu Pro Gln Trp Ile Asn Val Leu Gln Glu
                    50                  55                  60

Asp Ser Val Thr Leu Thr Cys Arg Gly Thr His Ser Pro Glu Ser Asp
 65                         70                  75                  80

Ser Ile Gln Trp Phe His Asn Gly Asn Leu Ile Pro Thr His Thr Gln
                                85                  90                  95

Pro Ser Tyr Arg Phe Lys Ala Asn Asn Asn Asp Ser Gly Glu Tyr Thr
                    100                 105                 110

Cys Gln Thr Gly Gln Thr Ser Leu Ser Asp Pro Val His Leu Thr Val
                    115                 120                 125

Leu Ser Glu Trp Leu Val Leu Gln Thr Pro His Leu Glu Phe Gln Glu
                    130                 135                 140

Gly Glu Thr Ile Val Leu Arg Cys His Ser Trp Lys Asp Lys Pro Leu
145                         150                 155                 160

Val Lys Val Thr Phe Phe Gln Asn Gly Lys Ser Lys Lys Phe Ser Arg
                    165                 170                 175

Ser Asp Pro Asn Phe Ser Ile Pro Gln Ala Asn His Ser His Ser Gly
                    180                 185                 190

Asp Tyr His Cys Thr Gly Asn Ile Gly Tyr Thr Leu Tyr Ser Ser Lys
                    195                 200                 205

Pro Val Thr Ile Thr Val Gln Ala Pro Ser Ser Ser Pro Met Gly Ile
                    210                 215                 220

Ile Val Ala Val Val Thr Gly Ile Ala Val Ala Ala Ile Val Ala Ala
225                         230                 235                 240

Val Val Ala Leu Ile Tyr Cys Arg Lys Lys Arg Ile Ser Ala Leu Pro
                    245                 250                 255

Gly Tyr Pro Glu Cys Arg Glu Met Gly Glu Thr Leu Pro Glu Lys Pro
                    260                 265                 270

Ala Asn Pro Thr Asn Pro Asp Glu Ala Asp Lys Val Gly Ala Glu Asn
                    275                 280                 285

Thr Ile Thr Tyr Ser Leu Leu Met His Pro Asp Ala Leu Glu Glu Pro
                    290                 295                 300

Asp Asp Gln Asn Arg Ile
305                 310

<210> SEQ ID NO 43
<211> LENGTH: 323
<212> TYPE: PRT
<213> ORGANISM: Homo sapiens

<400> SEQUENCE: 43

Met Gly Ile Leu Ser Phe Leu Pro Val Leu Ala Thr Glu Ser Asp Trp
 1               5                  10                  15

Ala Asp Cys Lys Ser Pro Gln Pro Trp Gly His Met Leu Leu Trp Thr
                    20                  25                  30

Ala Val Leu Phe Leu Ala Pro Val Ala Gly Thr Pro Ala Ala Pro Pro
                    35                  40                  45

Lys Ala Val Leu Lys Leu Glu Pro Gln Trp Ile Asn Val Leu Gln Glu
                    50                  55                  60
```

-continued

```
Asp Ser Val Thr Leu Thr Cys Arg Gly Thr His Ser Pro Glu Ser Asp
 65                  70                  75                  80

Ser Ile Gln Trp Phe His Asn Gly Asn Leu Ile Pro Thr His Thr Gln
                 85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Ser
                245                 250                 255

Thr Asp Pro Val Lys Ala Ala Gln Phe Glu Pro Pro Gly Arg Gln Met
            260                 265                 270

Ile Ala Ile Arg Lys Arg Gln Pro Glu Glu Thr Asn Asn Asp Tyr Glu
        275                 280                 285

Thr Ala Asp Gly Gly Tyr Met Thr Leu Asn Pro Arg Ala Pro Thr Asp
290                 295                 300

Asp Asp Lys Asn Ile Tyr Leu Thr Leu Pro Pro Asn Asp His Val Asn
305                 310                 315                 320

Ser Asn Asn

<210> SEQ ID NO 44
<211> LENGTH: 254
<212> TYPE: PRT
<213> ORGANISM: Homo sapiens

<400> SEQUENCE: 44

Met Trp Gln Leu Leu Leu Pro Thr Ala Leu Leu Leu Leu Val Ser Ala
 1               5                  10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
 65                  70                  75                  80

Val Asp Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
            100                 105                 110
```

```
Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 45
<211> LENGTH: 257
<212> TYPE: PRT
<213> ORGANISM: Homo sapiens

<400> SEQUENCE: 45

Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Lys Val
            20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
            115                 120                 125

Phe Leu Arg Cys His Gly Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Gln Phe Phe Ile
            195                 200                 205

Pro Leu Leu Val Val Ile Leu Phe Ala Val Asp Thr Gly Leu Phe Ile
    210                 215                 220

Ser Thr Gln Gln Gln Val Thr Phe Leu Leu Lys Ile Lys Arg Thr Arg
225                 230                 235                 240
```

```
Lys Gly Phe Arg Leu Leu Asn Pro His Pro Lys Pro Asn Pro Lys Asn
            245                 250                 255
Asn
```

FAIL MOLECULES AND USES THEREOF

RELATED APPLICATIONS

This application is a continuation of U.S. application Ser. No. 09/702,021, filed Oct. 30, 2000 now abandoned.

BACKGROUND OF THE INVENTION

Many secreted proteins, for example, cytokines and cytokine receptors, play a vital role in the regulation of cell growth, cell differentiation, and a variety of specific cellular responses. A number of medically useful proteins, including erythropoietin, granulocyte-macrophage colony stimulating factor, human growth hormone, and various interleukins, are secreted proteins. Thus, an important goal in the design and development of new therapies is the identification and characterization of secreted and transmembrane proteins and the genes which encode them.

Many secreted proteins are receptors which bind a ligand and transduce an intracellular signal, leading to a variety of cellular responses. Other secreted proteins are extracellular proteins that act as ligands by binding a receptor which leads to transduction of intracellular signals and ultimately results in downstream cellular responses. The identification and characterization of receptors and/or ligands permits identification of other molecules and of the signal transduction pathways associated with the receptors and/or ligands, permitting one to identify or design modulators of activity, e.g., receptor agonists or antagonists, modulators of signal transduction, and modulators of downstream cellular responses.

Virtually all cell types respond to extracellular and intercellular cues and induce one or more signal transduction pathways. Among such cell types are cells involved in the development, differentiation, activation, function, and maintenance of hematopoietic cells. These cell types include ones (e.g., B cells and T cells, and subpopulations thereof, such as T helper (TH) cells, including TH1 and TH2 cells) involved in a variety of immune and autoimmune responses, such as inflammatory responses. These responses can contribute to such diverse disorders as pulmonary disorders such as asthma and emphysema, arthritis, inflammatory bowel diseases such as Crohn's disease and ulcerative colitis, multiple sclerosis, graft-versus-host disease and tissue rejection. As such, identification of secreted proteins involved in some aspect of these cell types is particularly desirable.

SUMMARY OF THE INVENTION

The present invention is based, at least in part, on the discovery of cDNA molecules which encode the FAIL proteins, which are transmembrane proteins.

In particular, FAIL represents an Fc receptor (FcR) molecule.

The FAIL proteins, and fragments, derivatives, and variants, including allelic variants, thereof are collectively referred to herein as "polypeptides of the invention" or "proteins of the invention."

The term "nucleic acids of the invention," as used herein, refers to: 1) nucleic acid molecules encoding the polypeptides of the invention; 2) nucleic acid molecules present as part of FAIL transcripts or cDNA molecules encoding the polypeptides of the invention (e.g., upstream and/or downstream untranslated sequences); 3) nucleic acid molecules that hybridize to 1) and or 2) under the particular conditions discussed herein; and 4) nucleic acid molecules complementary to 1), 2) and/or 3).

The polypeptides of the invention are useful for a variety of purposes. The polypeptides of the invention are involved in immune disorders such as inflammatory bowel disease (e.g., Crohn's disease and ulcerative colitis), autoimmune disorders (e.g., multiple sclerosis), inflammatory disorders (e.g., rheumatoid arthritis and asthma), and chronic obstructive pulmonary disorders. As such, polypeptides of the invention are useful, for example, as modulators of immune disorders such as inflammatory bowel disease (e.g., Crohn's disease and ulcerative colitis), autoimmune disorders (e.g., multiple sclerosis), inflammatory disorders (e.g., rheumatoid arthritis and asthma), and chronic obstructive pulmonary disorders and for identification of additional modulators of immune disorders such as inflammatory bowel disease (e.g., Crohn's disease and ulcerative colitis), autoimmune disorders (e.g., multiple sclerosis) inflammatory disorders (e.g., rheumatoid arthritis and asthma), and chronic obstructive pulmonary disorders. The polypeptides of the invention are expressed in immune cells (e.g., T cells). As such, the polypeptides of the invention can be used as markers for identification, isolation, depletion, or tracking of immune cells, in particular T cells, in a sample. Further, the polypeptides of the invention can be used as antigens to make antibodies that can, in turn, be used for identification, isolation, depletion, or tracking of immune cells, in particular T cells, or FAIL in a sample, or to track immune disorders such as inflammatory bowel disease (e.g., Crohn's disease and ulcerative colitis), autoimmune disorders (e.g., multiple sclerosis), inflammatory disorders (e.g., rheumatoid arthritis and asthma), and chronic obstructive pulmonary disorders.

The nucleic acids of the invention are also useful for variety of purposes. First, among the nucleic acids of the invention are ones that encode a polypeptide of the invention. As such, these nucleic acids of the invention can be used to encode a polypeptide of the invention that is a modulator of immune disorders such as inflammatory bowel disease (e.g., Crohn's disease and ulcerative colitis), multiple sclerosis, rheumatoid arthritis, and respiratory inflammatory diseases (e.g., asthma and chronic obstructive pulmonary disorder), and as part of methods for identifying additional modulators of immune disorders such as inflammatory bowel disease (e.g., Crohn's disease and ulcerative colitis), multiple sclerosis, rheumatoid arthritis, and respiratory inflammatory diseases (e.g., asthma and chronic obstructive pulmonary disorder). The nucleic acids of the invention also include nucleic acid molecules present as part of FAIL transcripts or cDNA molecules, nucleic acid molecules that hybridize to such sequences under particular hybridization conditions discussed herein, and nucleic acid molecules complementary to such sequences. As such, nucleic acid molecules of the invention can be used for the identification and tracking of immune cells, in particular T cells, based on expression of FAIL. Still further, the nucleic acids of the invention can be used to track immune disorders such as inflammatory bowel disease (e.g., Crohn's disease and ulcerative colitis), autoimmune disorders (e.g., multiple sclerosis), inflammatory disorders (e.g., rheumatoid arthritis and asthma), and chronic obstructive pulmonary disorders.

The invention features nucleic acid molecules comprising a contiguous nucleotide sequence identical to the nucleotide sequence of SEQ ID NO:1, the nucleotide sequence of the cDNA insert of a EpFAIL clone deposited with the American Type Culture Collection ("ATCC®") as patent deposit Number PTA-2266, or a complement thereof.

The invention features nucleic acid molecules comprising a contiguous nucleotide sequence identical to the nucleotide sequence of SEQ ID NO:1, 2, 15, 16, 17, 18, 19, 20, 21, 22, 23, 24, 25, 26, 27, 28, or 29, or a complement thereof.

The invention features nucleic acid molecules that are at least 30%, preferably at least 35%, at least 40%, at 45%, at least 50%, at least 55%, at least 60%, at least 65%, at least 70%, at least 75%, at least 80%, at least 85%, at least 90%, at least 95%, or at least 98% identical to the nucleotide sequence of SEQ ID NO:1, 2, 15, 16, 17, 18, 19, 20, 21, 22, 23, 24, 25, 26, 27, 28, or 29, the nucleotide sequence of the cDNA insert of a EpFAIL clone deposited with the American Type Culture Collection ("ATCC®") as patent deposit Number PTA-2266, or a complement thereof. The invention features nucleic acid molecules that are at least 55%, preferably at least 60%, at least 65%, at least 70%, at least 75%, at least 80%, at least 85%, at least 90%, at least 95%, or at least 98% identical to the nucleotide sequence of SEQ ID NO:18, 19, or 20.

The invention features nucleic acid molecules which are at least 25%, preferably at least 30%, at least 35%, at least 40%, at 45%, at least 50%, at least 55%, at least 60%, at least 65%, at least 70%, at least 75%, at least 80%, at least 85%, at least 90%, at least 95%, or at least 98% identical to the nucleotide sequence of SEQ ID NO:1, 2, 15, 16, 17, 18, 19, 20, 21, 22, 23, 24, 25, 26, 27, 28, or 29, or the nucleotide sequence of the cDNA insert of a EpFAIL clone deposited with the American Type Culture Collection ("ATCC®") as patent deposit Number PTA-2266, wherein said nucleic acid molecules encode polypeptides that exhibit at least one structural and/or functional feature of a polypeptide of the invention.

The invention features nucleic acid molecules which comprise at least 15, preferably at least 25, at least 35, at least 40, at least 50, at least 75, at least 100, at least 125, at least 150, at least 175, at least 200, at least 225, at least 250, at least 275, at least 300, at least 325, at least 350, at least 375, at least 400, at least 425, at least 450, at least 475, at least 500, at least 525, at least 550, at least 575, at least 600, at least 625, at least 650, at least 675, at least 700, at least 725, at least 750, at least 775, at least 800, at least 825, at least 850, at least 875, at least 900, at least 925, at least 950, at least 975, at least 1000, at least 1050, at least 1100, at least 1150, at least 1200, at least 1250, at least 1300, at least 1350, at least 1400, at least 1450, at least 1500, at least 1550, at least 1600, at least 1650, at least 1700, at least 1750, at least 1800 or at least 1850 contiguous nucleotides of the nucleotide sequence of SEQ ID NO:1 or 2, the nucleotide sequence of a EpFAIL cDNA of ATCC® patent deposit Number PTA-2266, or a complement thereof.

The invention features isolated nucleic acid molecules comprising a nucleotide sequence that is at least about 15, preferably at least 25, at least 35, at least 40, at least 50, at least 75, at least 100, at least 125, at least 150, at least 200, at least 250, at least 300, at least 350, at least 400 or more contiguous nucleotides identical to the nucleic acid sequence of SEQ ID NO:1, 2, 15, 16, 17, 18, 19, 20, 21, 22, 23, 24, 25, 26, 27, 28, or 29, or the nucleotide sequence of the cDNA insert of EpFAIL of ATCC® patent deposit Number PTA-2266, wherein said nucleic acid molecules encode polypeptides that exhibit at least one structural and/or functional feature of a polypeptide of the invention.

The invention also features nucleic acid molecules comprising a contiguous nucleotide sequence that encodes a polypeptide of the amino acid sequence of SEQ ID NO: 3, 5, 6, 7, 8, 9, 10, 11, 30, 31, 32, 33, or 34, the amino acid sequence encoded by the cDNA insert of a EpFAIL of ATCC® patent deposit Number PTA-2266, or a complement thereof.

The invention also features nucleic acid molecules comprising a contiguous nucleotide sequence that encodes a polypeptide of an amino acid sequence that is at least 25%, preferably at least 30%, at least 35%, at least 40%, at least 45%, at least 50%, at least 55%, at least 60%, at least 65%, at least 70%, at least 75%, at least 80%, at least 85%, at least 90%, at least 95% or at least 98% identical to the amino acid sequence of SEQ ID NO:3, 4, 5, 6, 7, 8, 30, 31, 32, 33, 33, or 34, the amino acid sequence encoded by a EpFAIL cDNA of ATCC® patent deposit Number PTA-2266, or a complement thereof.

The invention also features nucleic acid molecules comprising a contiguous nucleotide sequence that encodes a polypeptide of an amino acid sequence that is at least 45%, preferably at least 50%, at least 55%, at least 60%, at least 65%, at least 70%, at least 75%, at least 80%, at least 85%, at least 90%, at least 95% or at least 98% identical to the amino acid sequence of SEQ ID NO:9 or 11. The invention also features nucleic acid molecules comprising a contiguous nucleotide sequence that encodes a polypeptide of an amino acid sequence that is at least 55%, preferably at least 60%, at least 65%, at least 70%, at least 75%, at least 80%, at least 85%, at least 90%, at least 95% or at least 98% identical to the amino acid sequence of SEQ ID NO:10.

The invention also features nucleic acid molecules comprising a nucleotide sequence encoding a polypeptide of an amino acid sequence that is at least 25%, preferably at least 30%, at least 35%, at least 40%, at least 45%, at least 50%, at least 55%, at least 60%, at least 65%, at least 70%, at least 75%, at least 80%, at least 85%, at least 90%, at least 95% or at least 98% identical to the amino acid sequence of SEQ ID NO:3, 5, 6, 7, 8, 9, 10, 11, 30, 31, 32, 33, or 34, or the amino acid sequence encoded by a EpFAIL cDNA of ATCC® patent deposit Number PTA-2266, wherein the polypeptide encoded by the nucleotide sequence also exhibits at least one structural and/or functional feature of a polypeptide of the invention.

The invention also includes nucleic acid molecules comprising a nucleotide sequence that encodes, a polypeptide comprising at least 15, preferably at least 25, at least 30, at least 25, at least 30, at least 35, at least 40, at least 45, at least 50, at least 55, at least 60, at least 65, at least 75, at least 80, at least 85, at least 90, at least 95, at least 100, at least 125, at least 150, at least 175, at least 200, at least 225, at least 250, at least 275, at least 300, at least 325, at least 350 or more contiguous amino acids of SEQ ID NO:3, or the amino acid sequence encoded by a EpFAIL cDNA of ATCC® patent deposit Number PTA-2266.

The invention also includes nucleic acid molecules which encode a naturally occurring variant, e.g., a naturally occurring allelic variant, of a polypeptide comprising the amino acid sequence of SEQ ID NO:3, 5, 6, 7, 8, 9, 10, or 11, or encoding the amino acid sequence encoded by a EpFAIL cDNA of ATCC® patent deposit Number PTA-2266, wherein the nucleic acid molecule hybridizes to a nucleic acid molecule consisting of a nucleic acid sequence encoding SEQ ID NO:1, 2, 15, 16, 17, 18, 19, 20 or 21, or encoding the amino acid sequence encoded by a EpFAIL cDNA of ATCC® patent deposit Number PTA-2266, or a complement thereof, under stringent conditions.

The invention also features nucleic acid molecules that hybridize under stringent conditions to a nucleic acid molecule having the nucleotide sequence of SEQ ID NO:1 or 2, a EpFAIL cDNA of ATCC® patent deposit Number PTA-2266, or a complement thereof. In other embodiments, the nucleic acid molecules are at least 15, preferably at least 25, at least 30, at least 35, at least 40, at least 45, at least 50, at least 55, at least 60, at least 65, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500, at least 525, at least 550, at least 575, at least 600, at least 625, at least 650, at least 700, at least 725, at least 750, at least 775, at least 800, at least 825, at least 850, at least 875, at least 900, at least 925, at least 950, at least 975, at least 1000, at least 1050, at least 1200, at least 1250, at least 1300, at least 1350, at least 1400, at least 1450, at least 1500, at least 1550, at least 1600, at least 1650, at least 1700, at least 1750, at least 1800, at least 1850 or more contiguous nucleotides in length and hybridize under stringent conditions to a nucleic acid molecule comprising the nucleotide sequence of SEQ ID NO:1, a EpFAIL cDNA of ATCC® patent deposit Number PTA-2266, or a complement thereof.

The invention also features nucleic acid molecules that hybridize under stringent conditions to a nucleic acid molecule having the nucleotide sequence of SEQ ID NO:1, 2, 15, 16, 17, 18, 19, 20, 21, 22, 23, 24, 25, 26, 27, 28, or 29, or a nucleotide sequence of EpFAIL cDNA of ATCC® patent deposit Number PTA-2266, or complement thereof, wherein such nucleic acid molecules encode polypeptides that exhibit at least one structural and/or functional feature of a polypeptide of the invention.

The invention also features nucleic acid molecules at least 15, preferably at least 25, at least 30, at least 35, at least 40, at least 45, at least 50, at least 55, at least 60, at least 65, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500, at least 525, at least 550, at least 575, at least 600, at least 625, at least 650, at least 700, at least 725, at least 750, at least 775, at least 800, at least 825, at least 850, at least 875, at least 900, at least 925, at least 950, at least 975, at least 1000, at least 1050, at least 1200, at least 1250, at least 1300, at least 1350, at least 1400, at least 1450, at least 1500, at least 1550, at least 1600, at least 1650, at least 1700, at least 1750, at least 1800, at least 1850 or more contiguous nucleotides in length which hybridize under stringent conditions to a nucleic acid molecule comprising the nucleotide sequence of SEQ ID NO:3, 5, 6, 7, 8, 9, 10, 11, 30, 31, 32, 33, or 34, or a nucleotide sequence of a EpFAIL cDNA of ATCC® patent deposit Number PTA-2266, or a complement thereof, wherein said nucleic acid molecules encode polypeptides or proteins that exhibit at least one structural and/or functional feature of a polypeptide of the invention.

In one embodiment, the invention provides an isolated nucleic acid molecule which is antisense to the coding strand of a nucleic acid of the invention.

Preferred nucleic acid molecules of the invention are ones that encode a protein or polypeptide of the invention that possesses at least one biological activity possessed by the corresponding naturally-occurring human polypeptide.

Another aspect of the invention provides vectors, e.g., recombinant expression vectors, comprising a nucleic acid molecule of the invention, and methods for producing such vectors. In another embodiment, the invention provides host cells containing such a vector or engineered to contain and/or express a nucleic acid molecule of the invention, and methods for producing such host cells. The invention also provides methods for producing a polypeptide of the invention by culturing, in a suitable medium, a host cell of the invention such that a polypeptide of the invention is produced.

The invention also features isolated FAIL polypeptides of the invention. In one embodiment, a FAIL protein includes at least one or more of the following domains: a signal sequence, an immunoglobulin domain, an immunoglobulin-like domain, or an amino acid sequence sufficiently identical to an identified domain of a polypeptide of the invention.

As used herein, the term "sufficiently identical" refers to a first amino acid which contains a sufficient or minimum number of identical or equivalent (e.g., with a similar side chain) amino acid residues to a second amino acid, such that the first and second amino acid have a common structural domain and/or common functional activity. For example, amino acid sequences which contain or encode a common structural domain having about 60% identity, preferably 65% identity, more preferably 75%, 85%, 95%, 98% or more identity are defined herein as sufficiently identical. Likewise, as used herein, the term "sufficiently identical" refers to a first nucleotide sequence which contains a sufficient or minimum number of identical or equivalent (e.g., degenerate nucleotides for amino acid coding purposes) nucleotides to a nucleotide sequence such that the first and second nucleotide sequences encode polypeptides with a common structural domain and/or common functional activity.

The invention features isolated polypeptides comprising the amino acid sequence or SEQ ID NO:3, 4, 5, 6, 7, 8, 9, 10, 11, 30, 31, 32, 33, or 34, or the amino acid sequence encoded by a EpFAIL cDNA of ATCC® patent deposit Number PTA-2266.

The invention also includes isolated polypeptides comprising an amino acid sequence that is at least about 25%, preferably at least 30%, at least 35%, at least 40%, at least 45%, at least 50%, at least 55%, at least 60%, at least 65%, at least 70%, at least 75%, at least 80%, at least 85%, at least 90%, at least 95% or at least 98% identical to the amino acid sequence of SEQ ID NO:3, 4, 5, 6, 7, 8, 30, 31, 32, 33, or 34 or the amino acid sequence encoded by a EpFAIL cDNA of ATCC® patent deposit Number PTA-2266. The invention also includes isolated polypeptides comprising an amino acid sequence that is at least 40%, preferably at least 45%, at least 50%, at least 55%, at least 60%, at least 65%, at least 70%, at least 75%, at least 80%, at least 85%, at least 90%, at least 95% or at least 98% identical to the amino acid sequence of SEQ ID NO:9 or 11. The invention also includes isolated polypeptides comprising an amino acid sequence that is at least 55%, preferably at least 60%, at least 65%, at least 70%, at least 75%, at least 80%, at least 85%, at least 90%, at least 95% or at least 98% identical to the amino acid sequence of SEQ ID NO:10.

The invention also features isolated polypeptides comprising an amino acid sequence that is at least about 25%, preferably at least 30%, at least 35%, at least 40%, at least 45%, at least 50%, at least 55%, at least 60%, at least 65%, at least 70%, at least 75%, at least 80%, at least 85%, at least 90%, at least 95% or at least 98% identical to the amino acid sequence of SEQ ID NOS:3, 4, 5, 6, 7, 8, 9, 10 ,11 30, 31, 32, 33, or 34, or the amino acid sequence encoded by a EpFAIL cDNA of ATCC® patent deposit Number PTA-2266, wherein the polypeptides also exhibit at least one structural and/or functional feature of a polypeptide of the invention.

The invention also includes isolated polypeptides which are encoded by a nucleic acid molecule having a nucleotide sequence that is at least about 25%, preferably at least 30%, at least 35%, at least 40%, at least 45%, at least 50%, at least 55%, at least 60%, at least 65%, at least 70%, at least 75%, at least 80%, at least 85%, at least 90%, at least 95% or at least 98% identical to the nucleic acid sequence encoding SEQ ID NO:1, and isolated polypeptides which are encoded by a nucleic acid molecule having a nucleotide sequence which hybridizes under stringent hybridization conditions to a nucleic acid molecule having the nucleotide sequence of SEQ ID NO:1 or 2, a complement thereof, or the non-coding strand of a EpFAIL cDNA of ATCC® patent deposit Number PTA-2266.

The invention also features isolated polypeptides which are encoded by a nucleic acid molecule having a nucleotide sequence that is at least about 25%, preferably at least 30%, at least 35%, at least 40%, at least 45%, at least 50%, at least 55%, at least 60%, at least 65%, at least 70%, at least 75%, at least 80%, at least 85%, at least 90%, at least 95% or 98% identical to a nucleic acid sequence encoding SEQ ID NO:3, 4, 5 ,6, 7, 8, 9, 10, 11, 30, 31, 32, 33, or 34, isolated polypeptides which are encoded by a nucleic acid molecule having a nucleotide sequence which hybridizes under stringent hybridization conditions to a nucleic acid molecule having the nucleotide sequence of SEQ ID NO:1, 2, 15, 16, 17, 18, 19, 20, 21, 22, 23, 24, 25, 26, 27, 28 or 29, a complement thereof, or the non-coding strand of a EpFAIL cDNA of ATCC® patent deposit Number PTA-2266, wherein the polypeptides also exhibit at least one structural and/or functional feature of a polypeptide of the invention.

The invention features polypeptides which comprise at least 15, preferably at least 25, at least 30, at least 35, at least 40, at least 45, at least 50, at least 55, at least 60, at least 65, at least 75, at least 80, at least 85, at least 90, at least 95, at least 100, at least 125, at least 150, at least 175, at least 200, at least 225, at least 250, at least 275, at least 300, at least 325, or at least 350 contiguous amino acid residues of the amino acid sequence of SEQ ID NO:3, or the amino acid sequence encoded by the cDNA insert of a EpFAIL cDNA of ATCC® patent deposit Number PTA-2266. In preferred embodiments, the polypeptides represent N-terminal and/or C-terminal truncations of the amino acid sequence of SEQ ID NO:3, the amino acid sequence of the mature FAIL polypeptide, or the amino acid sequence encoded by the cDNA insert of a EpFAIL cDNA of ATCC® patent deposit Number PTA-2266. In one embodiment, such a polypeptide of the invention represents an antigenic polypeptide comprising at least 15 contiguous amino acids of the amino acid sequence of SEQ ID NO:3, 4, 5, 6, 7, 8, 9, 10, 11, 30, 31, 32, 33 or 34, or the amino acid sequence encoded by a EpFAIL cDNA insert deposited with the ATCC® as patent deposit Number PTA-2266, wherein antibodies generated against the polypeptide bind to a native FAIL.

The invention also includes polypeptides which are naturally occurring variants, e.g., naturally occupying allelic variants, of a polypeptide that includes the amino acid sequence of SEQ ID NO:3, 4, 5, 6, 7, 8, 9, 10, 11, 30, 31, 32, 33 or 34, or the amino acid sequence encoded by a EpFAIL cDNA of ATCC® patent deposit Number PTA-2266, wherein the polypeptide is encoded by a nucleic acid molecule which hybridizes to a nucleic acid molecule having the sequence of SEQ ID NO:1, 2, 15, 16, 17, 18, 19, 20, 21, 22, 23, 24, 25, 26, 27, 28, or 29, or a complement thereof, under stringent conditions.

The polypeptides of the present invention can be operably linked to a heterologous amino acid sequence to form fusion proteins. In one embodiment, the heterologous amino acid sequence is fused to the N-terminus of the polypeptide of the invention. In another embodiment, the heterologous amino acid sequence is fused to the C-terminus of the polypeptide of the invention.

In addition, the polypeptides of the invention can be incorporated into pharmaceutical compositions, which optionally include pharmaceutically acceptable carriers.

Preferred proteins and polypeptides of the invention possess at least one biological activity possessed by the corresponding naturally-occurring human polypeptide. A biological activity of a polypeptide of the invention refers, first, to an activity exerted by a protein or polypeptide of the invention on a responsive cell, protein, or nucleic acid as determined in vivo or in vitro, according to standard techniques. Such activities can be a direct activity, such as an association with, or an enzymatic activity on, a protein or modulation of gene expression via association with a nucleic acid regulatory sequence, or an indirect activity, such as a cellular signaling activity, mediated by interaction of the protein with a second protein. Such biological activities can also be considered to be functional features of the polypeptides of the invention. A biological activity of a polypeptide of the invention also refers to an antigenic or immunogenic activity of a polypeptide of the invention, e.g., the ability of the polypeptide to act as an antigen for production of antibodies, and the ability of the polypeptide to act as an immunogen for mounting an immune response directed against the polypeptide. Such a biological activity is one, non-limiting example of a structural feature of the polypeptides of the invention.

For FAIL, biological activities include, e.g., (1) the ability to modulate (e.g., stabilize, increase or promote, suppress, decrease, inhibit, or disrupt) and/or track (e.g., identify, follow, monitor, or measure) protein-protein interactions (e.g., homophilic and/or heterophilic), and protein-ligand interactions, e.g., in receptor-ligand recognition; (2) the ability to modulate and/or track intracellular signaling cascades (e.g., Syk phosphorylation, Lyn phosphorylation, Lck phosphorylation, intracellular $Ca^{2+}$, and ZAP-70 phosphorylation) or intercellular signaling cascades (e.g., immune system signaling); (3) the ability to modulate and/or track hematopoietic processes, e.g., the ability to modulate endocytosis and/or phagocytosis; (4) the ability to modulate and/or track the immunoregulatory functions, such as host immune response, e.g., by modulating one or more elements in the inflammatory response such as IgE expression or histamine production; (5) the ability to modulate and/or track the development, differentiation, maturation, morphology, migration or chemotaxis, proliferation and/or activity of immune cells (e.g., leukocytes such as B-lymphocytes, T-lymphocytes, monocytes, natural killer cells, eosinophils, and macrophages); (6) the ability to modulate and/or track ligand-receptor interactions in proteins with immunoglobulin domains; (7) the ability to modulate and/or track lymphocyte selection (such as modulation of B-cell receptor or T-cell receptor stimulation in developing lymphocytes, e.g., through modulation of ligand (e.g., antigen) interaction with immunoglobulin domains of the receptors); (8) the ability to modulate and/or track autoimmunity (e.g., as associated with multiple sclerosis, psoriasis, arthritis, lupus); (9) the ability to modulate and/or track inflammatory functions e.g., by modulating leukocyte adhesion to extracellular matrix; (10) the ability to associate with and/or co-express with FcR subunits (e.g., the β and γ FcR subunits); (11) the ability to modulate and/or track homeostasis; (12) the ability to modulate (e.g., inhibit or stimulate) and/or track the expression of molecules, e.g., antibody expression (e.g., IgM, IgG, IgE and/or IgA expression), histamine expression, the expression of T cell activation markers such as ICOS and CD28, and the expression of cytokines such as IFN-α, IFN-β, IFN-γ, IL-2, IL-4, IL-5, IL-6, IL-10, IL-12, IL-15, and IL-18; (13) the ability to alter, e.g., increase, expression in response to stimuli and pathophysiological stimuli relevant to inflammatory processes and disorders; and (14) the ability to modulate and/or track the proliferation, differentiation function and/or activity of immune cells, e.g., T-cells and natural killer cells.

The invention further features antibodies, such as monoclonal or polyclonal antibodies, that specifically bind a polypeptide of the invention. Thus, in one aspect, the invention provides antibodies or fragments thereof, preferably substantially purified antibodies or fragments thereof, including human, humanized, chimeric and non-human antibodies or fragments thereof, which antibodies or fragments specifically bind to a polypeptide comprising an amino acid sequence of SEQ ID NO:3, 4, 5, 6, 7, 8, 9, 10, 11, 30, 31, 32, 33 or 34, or the amino acid sequence encoded by a EpFAIL cDNA insert deposited with the ATCC® as patent deposit Number PTA-2266.

In another aspect, the invention provides antibodies or fragments thereof, preferably substantially purified antibodies or fragments thereof, including, e.g., human, non-human, chimeric and humanized antibodies, which antibodies or fragments thereof specifically bind to a polypeptide comprising at least 95% identical to the amino acid sequence of SEQ ID NO:3, 4, 5, 6, 7, 8, 9, 10, 11, 30, 31, 32, 33 or 34, or the amino acid sequence encoded by a EpFAIL cDNA insert deposited with the ATCC® as patent deposit Number PTA-2266, wherein the percent identity is determined using the ALIGN program of the GCG software package with a PAM120 weight residue table, a gap length penalty of 12, and a gap penalty of 4.

In another aspect, the invention provides antibodies or fragments thereof, preferably substantially purified antibodies or fragments thereof, including, e.g., human, non-human, chimeric and humanized antibodies, which antibodies or fragments thereof specifically bind to a polypeptide encoded by a nucleic acid molecule which hybridizes to the nucleic acid molecule of SEQ ID NO:1, 2, 15, 16, 17, 18, 19, 20, 21, 22, 23, 24, 25, 26, 27, 28 or 29, or the nucleotide sequence of a EpFAIL cDNA insert deposited with the ATCC® as patent deposit Number PTA-2266 under conditions of hybridization of 6×SSC at 45° C. and washing in 0.2×SSC, 0.1% SDS at 50° C., 55° C., 60° C. or 65° C., or 6×SSC at 45° C. and washing in 0.1×SSC, 0.2% SDS at 68° C.

Any of the antibodies of the invention or fragments thereof can be conjugated to a therapeutic moiety or to a detectable substance. Non-limiting examples of detectable substances that can be conjugated to the antibodies of the invention are an enzyme, a prosthetic group, a fluorescent material, a luminescent material, a bioluminescent material, and a radioactive material.

The invention also provides a kit containing an antibody of the invention or fragment thereof conjugated to a detectable substance, and instructions for use. Still another aspect of the invention is a pharmaceutical composition comprising an antibody of the invention or a fragment thereof and a pharmaceutically acceptable carrier. In preferred embodiments, the pharmaceutical composition contains an antibody of the invention or fragment thereof, a therapeutic moiety, and a pharmaceutically acceptable carrier.

Still another aspect of the invention is a method of making an antibody that specifically recognizes FAIL, the method comprising immunizing a mammal with a polypeptide. The polypeptide used as an immunogen comprises an amino acid sequence selected from the group consisting of: the amino acid sequence of SEQ ID NO:3, 4, 5, 6, 7, 8, 9, 10, 11, 30, 31, 32, 33 or 34, or the amino acid sequence encoded by a EpFAIL cDNA insert deposited with the ATCC® as patent deposit Number PTA-2266; a fragment of at least 15 amino acid residues of the amino acid sequence of SEQ ID NO:3, 4, 5, 6, 7, 8, 9, 10, 11, 30, 31, 32, 33 or 34; an amino acid sequence which is at least 50%, at least 55%, at least 60%, at least 65%, at least 70%, at least 75%, at least 80%, at least 85%, at least 90%, at least 95% or at least 98% identical to the amino acid sequence of SEQ ID NO:3, 4, 5, 6, 7, 8, 9, 10, 11, 30, 31, 32, 33 or 34, wherein the percent identity is determined using the ALIGN program of the GCG software package with a PAM120 weight residue table, a gap length penalty of 12, and a gap penalty of 4; and an amino acid sequence which is encoded by a nucleic acid molecule which hybridizes to the nucleic acid molecule consisting of SEQ ID NO:1, 2, 15, 16, 17, 18, 19, 20, 21, 22, 23, 24, 25, 26, 27, 28, or 29 under conditions of hybridization of 6×SSC at 45° C. and washing in 0.2×SSC, 0.1% SDS at 50° C., 55° C., 60°C. or 65° C., or 6×SSC at 45° C. and washing in 0.1×SSC, 0.2% SDS at 68° C. After immunization, a sample is collected from the mammal that contains an antibody that specifically recognizes FAIL. Preferably, the polypeptide is recombinantly produced using a non-human host cell. Optionally, the antibodies can be further purified from the sample using techniques well known to those of skill in the art. The method can further comprise producing a monoclonal antibody-producing cell from the cells of the mammal. Optionally, antibodies are collected from the antibody-producing cell.

In another aspect, the present invention provides methods for detecting the presence, activity or expression of a polypeptide of the invention in a biological sample by contacting the biological sample with an agent capable of being detected as an indicator of the presence, activity or expression of a polypeptide of the invention in the biological sample.

In another aspect, the invention provides methods for modulating activity of a polypeptide of the invention comprising contacting a cell or a polypeptide of the invention with an agent that modulates (e.g., inhibits or stimulates) the activity or expression of a polypeptide of the invention such that activity or expression in the cell is modulated. In one embodiment, the agent is an antibody that specifically binds to a polypeptide of the invention. In another embodiment, the agent modulates expression of a polypeptide of the invention by modulating transcription, splicing, or translation of an mRNA encoding a polypeptide of the invention. In yet another embodiment, the agent is a nucleic acid molecule having a nucleotide sequence that is antisense to the coding strand of an mRNA encoding a polypeptide of the invention.

The present invention also provides methods to treat a subject having a disorder characterized by aberrant activity of a polypeptide of the invention or aberrant expression of a nucleic acid of the invention by administering an agent which is a modulator of the activity of a polypeptide of the invention or a modulator of the expression of a nucleic acid of the invention to the subject. In one embodiment, the modulator is a protein of the invention. In another embodiment, the modulator is a nucleic acid of the invention. In other embodiments, the modulator is a peptide, peptidomimetic, or other small molecule.

The present invention also provides diagnostic assays for identifying the presence or absence of a genetic lesion or mutation characterized by at least one of: (i) aberrant modification or mutation of a gene encoding a polypeptide of the invention; (ii) mis-regulation of a gene encoding a polypeptide of the invention; and (iii) aberrant post-translational modification of the invention wherein a wild-type form of the gene encodes a protein having the activity of the polypeptide of the invention.

In another aspect, the invention provides a method for identifying a compound that binds to a polypeptide of the invention. In general, such methods comprise contacting a test compound with a polypeptide of the invention for a time sufficient for the test compound to bind the polypeptide, removing unbound test compound, and assaying for the presence of bound test compound. Preferentially, the test compound is one that selectively binds a polypeptide of the invention.

As used herein, the term "selectively binds" refers to a compound (e.g., an antibody or small organic molecule) that binds to a FAIL polypeptide of the invention preferentially relative to other unrelated polypeptides. A compound selectively binds to a FAIL polypeptide preferentially relative to an unrelated polypeptide if it has at least a 10%, preferably at least a 25%, at least a 50%, at least a 75%, at least a 90%, at least a 95%, or at least a 100% higher affinity and/or avidity for a FAIL polypeptide of the invention than an unrelated polypeptide.

In yet another aspect, the invention provides a method for identifying a compound that modulates the activity of a polypeptide of the invention. In general, such methods comprise measuring a biological activity of a polypeptide of the invention in the presence of a test compound, comparing the activity of the polypeptide to the biological activity of the polypeptide in the absence of the test compound, and identifying a test compound that alters the biological activity or the polypeptide.

The invention also features methods for identifying a compound which modulates the expression of a polypeptide or nucleic acid of the invention by measuring the expression of the polypeptide or nucleic acid in the presence of the compound and comparing the expression to that measured in the absence of the compound.

Other features and advantages of the invention will be apparent from the following detailed description and claims.

BRIEF DESCRIPTION OF THE DRAWINGS

FIG. 1A–1B depict the cDNA sequence of human FAIL (SEQ ID NO:1) and the predicted amino acid sequence of human FAIL (SEQ ID NO:3). The open reading frame of SEQ ID NO:1 extends from nucleotide 66 to nucleotide 1175 of SEQ ID NO:1 (SEQ ID NO:2).

FIG. 3A depicts an alignment of the amino acid sequence of a typical immunoglobulin domain (SEQ ID NO:12; GenBank Accession Number PF00047) and amino acid residues 27 to 80 of human FAIL (otherwise referred to as D1; SEQ ID NO:9). This alignment was performed using the ALIGN alignment program with a PAM120 scoring matrix, a gap length penalty of 12, and a gap penalty of 4.

FIG. 3B depicts an alignment of the amino acid sequence of a typical immunoglobulin domain (SEQ ID NO:12; GenBank Accession Number PF00047) and amino acid residues 120 to 177 of human FAIL (otherwise referred to as D2; SEQ ID NO:10). This alignment was performed using the ALIGN alignment program with a PAM120 scoring matrix, a gap length penalty of 12, and a gap penalty of 4.

FIG. 3C depicts an alignment of the amino acid sequence of a typical immunoglobulin domain (SEQ ID NO:12; GenBank Accession Number PF00047) and amino acid residues 216 to 273 of human FAIL (otherwise referred to as D3; SEQ ID NO:11). This alignment was performed using the ALIGN alignment program with a PAM120 scoring matrix, a gap length penalty of 12, and a gap penalty of 4.

FIGS. 4A–4C depict alignments of the amino acid sequence for human FAIL and the amino acid sequences for human FcγRI (SEQ ID NO:14; GenBank Accession No. AAA35678), human FcγRIIA (SEQ ID NO:41; GenBank Accession No. CAA01563), human FcγRIIB (SEQ ID NO:42; GenBank Accession No. P31994), human FcγRIIC (SEQ ID NO:43; GenBank Accession No. P31995), human FcγRIIIa (SEQ ID NO:44; GenBank Accession No. P08637), and human FcεRI (SEQ ID NO:45; GenBank Accession No. P12319). The amino acid residues shaded with solid black comprise the consensus sequence.

FIGS. 5A–5B depict an alignment of the nucleotide sequence of the open reading frame for the alpha subunit of human FcγR1 (SEQ ID NO:13; GenBank Accession No. X14355) and the nucleotide sequence of the open reading frame for human FAIL (SEQ ID NO:2). The nucleotide sequences of coding regions of the alpha subunit of human FcγRI and human FAIL are 28.7% identical. This alignment was performed using the ALIGN alignment program with a PAM120 scoring matrix, a gap length penalty of 12, and a gap penalty of 4.

FIG. 6 depicts an alignment of the amino acid sequence of the alpha subunit of human FcγR1 (SEQ ID NO:14; GenBank Accession No. AAA35678) and the amino acid sequence of human FAIL (SEQ ID NO:3). The amino acid sequences of the alpha subunit of human FcγRI and human FAIL are 22.7% identical. This alignment was performed using the ALIGN alignment program with a PAM120 scoring matrix, a gap length penalty of 12, and a gap penalty of 4.

DETAILED DESCRIPTION OF THE INVENTION

Figure 2:
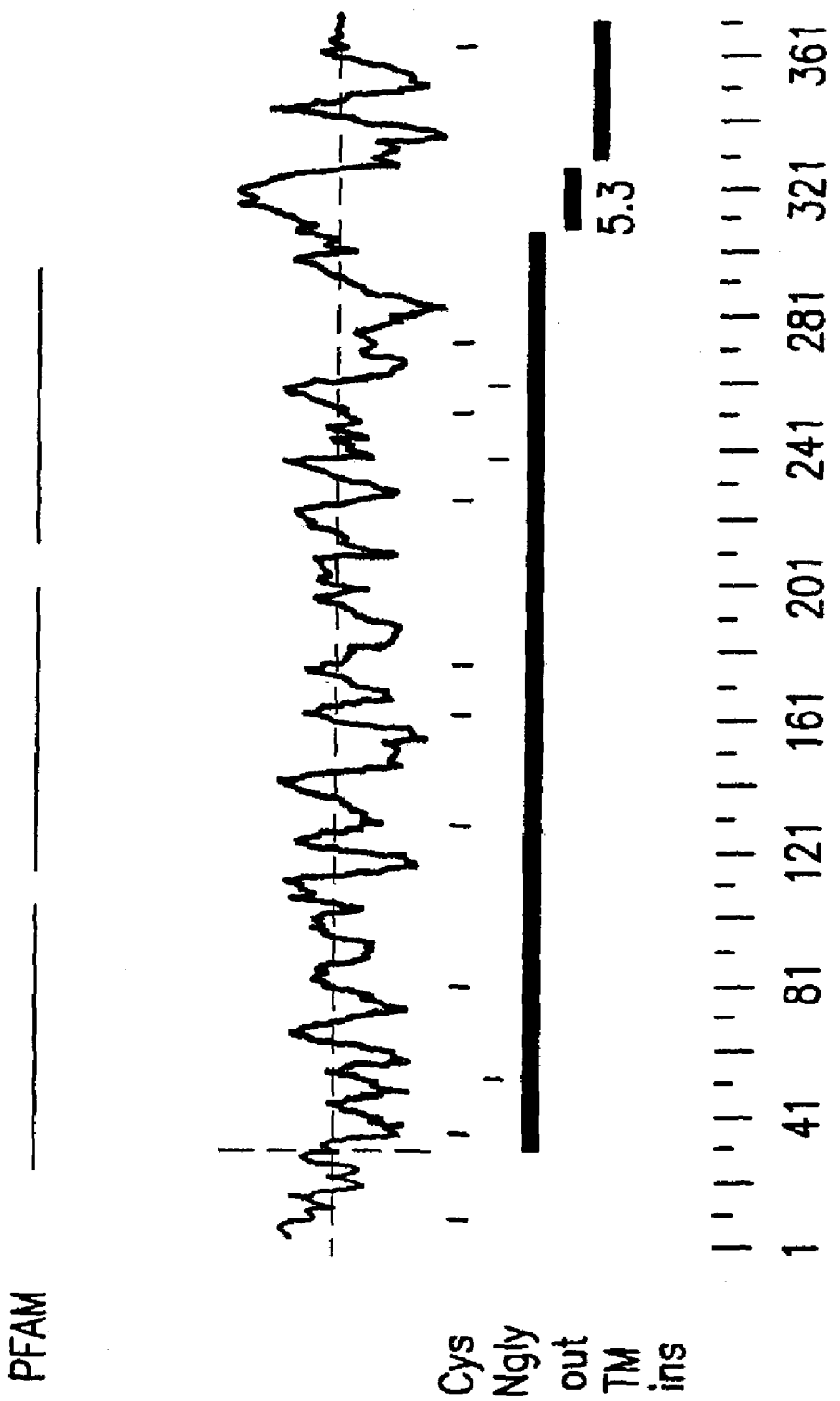
FIG. 2 depicts a hydropathy plot of human FAIL. Relatively hydrophobic regions of the protein are above the dashed horizontal line, and relatively hydrophilic regions of the protein are below the dashed horizontal line. The cysteine residues (cys) are indicated by short vertical lines just below the hydropathy trace. The dashed vertical line separates the signal sequence (amino acids 1 to 27 of SEQ ID NO:3; SEQ ID NO:4) on the left from the mature protein (amino acids 28 to 370 of SEQ ID NO:3; SEQ ID NO:5) on the right.

The FAIL proteins and nucleic acid molecules comprise a family of molecules having certain conserved structural and functional features. As used herein, the term "family" is intended to mean two or more proteins or nucleic acid molecules having a common structural domain and having sufficient amino acid or nucleotide sequence identity as defined herein. Family members can be from either the same or different species. For example, a family can comprise two or more proteins of human origin, or can comprise one or more proteins of human origin and one or more of non-human origin. Members of the same family may also have common structural domains.

For example, FAIL proteins of the invention have signal sequences. As used herein, a "signal sequence" includes a peptide of at least about 15 or 20 amino acid residues in length which occurs at the N-terminus of secretory and membrane-bound proteins and which contains at least about 70% hydrophobic amino acid residues such as alanine, leucine, isoleucine, phenylalanine, proline, tyrosine, tryptophan, or valine. In a preferred embodiment, a signal sequence contains at least about 10 to 40 amino acid residues, preferably about 19–34 amino acid residues, and has at least about 60–80%, more preferably 65–75%, and more preferably at least about 70% hydrophobic residues. A signal sequence serves to direct a protein containing such a sequence to a lipid bilayer. Thus, in one embodiment, a FAIL protein contains a signal sequence at about amino acids 1 to 27 of SEQ ID NO:3 (SEQ ID NO:4). The signal sequence is cleaved during processing of the mature protein.

A FAIL family member comprises one or more of the following domains: (1) an extracellular domain; (2) a transmembrane domain; and (3) a cytoplasmic domain. In one embodiment, a FAIL protein contains an extracellular domain at about amino acid residues 28 to 305 of SEQ ID NO:3 (SEQ ID NO:6), a transmembrane domain at amino acid residues 306 to 325 of SEQ ID NO:3 (SEQ ID NO:7), and a cytoplasmic domain at amino acid residues 326 to 370 of SEQ ID NO:3 (SEQ ID NO:8). In this embodiment, the mature FAIL protein (that is the FAIL protein without a signal sequence) corresponds to amino acids 28 to 370 of SEQ ID NO:3 (SEQ ID NO:5). In another embodiment, a FAIL protein contains an extracellular domain at about amino acid residues 1 to 305 of SEQ ID NO:3 (SEQ ID NO:34), a transmembrane domain at amino acid residues 306 to 325 of SEQ ID NO:3 (SEQ ID NO:7), and a cytoplasmic domain at amino acid residues 326 to 370 of SEQ ID NO:3 (SEQ ID NO:8). In this embodiment, the mature FAIL protein corresponds to amino acids 1 to 370 of SEQ ID NO:3.

A FAIL family member can include a signal sequence. Thus, in one embodiment, a FAIL family member comprises a signal sequence, an extracellular domain, a transmembrane domain, and a cytoplasmic domain. In certain embodiments, a FAIL family member has the amino acid sequence of SEQ ID NO:3, and the signal sequence is located at amino acids 1 to 25, 2 to 25, 1 to 26, 2 to 26, 1 to 27, 2 to 27, 1 to 28, 2 to 29, or 2 to 29. In such embodiments of the invention, the extracellular domain and the mature protein resulting from cleavage of such signal peptides are also included herein. For example, the cleavage of a signal sequence consisting of amino acids 1 to 26 results in an extracellular domain consisting of amino acids 27 to 305 of SEQ ID NO:3 and the mature FAIL protein corresponding to amino 27 to 370.

A FAIL family member can include one or more immunoglobulin (Ig) domains and/or Ig-like domains. In one embodiment, a FAIL family member comprises a signal sequence, an extracellular domain, an Ig domain, two Ig-like domains, a transmembrane domain, and a cytoplasmic domain. An Ig domain typically has the following consensus sequence, beginning at about 1 to 15 amino acid residues, more preferably at about 3 to 10 amino acid residues, and most preferably at about 5 amino acid residues from the C-teiminal end of a protein: (FY)-Xaa-C-Xaa-(VA)—COO—, wherein (FY) is either a phenylalanine or a tyrosine residue (preferably tyrosine), where "Xaa" is any amino acid, C is a cysteine residue, (VA) is either valine or an alanine residue (preferably alanine), and COO— is the protein C-terminus. In one embodiment, a FAIL family member includes one or more Ig domains having an amino acid sequence that is at least about 55%, preferably at least about 65%, more preferably at least 75%, yet more preferably at least about 85%, and most preferably at least about 95% identical to amino acids 27 to 80 of SEQ ID NO:3, which is the Ig domain of human FAIL (this Ig domain is also represented as SEQ ID NO:9).

In another embodiment, a FAIL family member includes one or more Ig domains having an amino acid sequence that is at least about 55%, preferably at least about 65%, more preferably at least about 75%, yet more preferably at least about 85%, and most preferably at least about 95% identical to amino acids 27 to 80 of SEQ ID NO:3, which is the Ig domain of human FAIL (this Ig domain are also represented as SEQ ID NO:9), includes a conserved cysteine residue about 8 residues downstream from the N-terminus of the Ig domain, and has one or more Ig domain consensus sequences as described herein.

In another embodiment, a FAIL family member includes one or more Ig domains having an amino acid sequence that is at least 55%, preferably at least about 65%, more preferably at least about 75%, yet more preferably at least about 85%, and most preferably at least about 95% identical to amino acids 27 to 80 of SEQ ID NO:3, which is the Ig domain of human FAIL (this Ig domain are also represented as SEQ ID NO:9), includes a conserved cysteine residue 8 residues downstream from the N-terminus of the Ig domain, has one or more Ig domain consensus sequences as described herein, and has a conserved cysteine within the consensus sequence that forms a disulfide with said first conserved cysteine.

In yet another embodiment, a FAIL family member includes one or more Ig domains having an amino acid sequence that is at least 55%, preferably at least about 65%, more preferably at least about 75%, yet more preferably at least about 85%, and most preferably at least about 95% identical to amino acids 27 to 80 of SEQ ID NO:3, which is the Ig domain of human FAIL (this Ig domain are also represented as SEQ ID NO:9), includes a conserved cysteine residue 8 residues downstream from the N-terminus of the Ig domain, has one or more Ig domain consensus sequences described herein, has a conserved cysteine within the consensus sequence that forms a disulfide with said first conserved cysteine, and has at least one FAIL biological activity as described herein.

In a preferred embodiment, a FAIL family member has the amino acid sequence of SEQ ID NO:3, wherein the aforementioned Ig domain conserved residues are located as follows: the N-terminal conserved cysteine residue is located at amino acid residue position 34 (within the Ig domain of SEQ ID NO:3) and the C-terminal conserved cysteine residue is located at amino acid position 78 (within the Ig domain of SEQ ID NO:3).

An Ig-like domain as described herein has the following consensus sequence, beginning at about 1 to 15 amino acid residues, more preferably at about 3 to 10 amino acid residues, and most preferably at about 5 amino acid residues from the domain C-terminus: (FY)-Xaa-C, wherein 5(FY) is either a phenylalanine or a tyrosine residue (preferably tyrosine), where "Xaa" is any amino acid, and C is a cysteine residue. In one embodiment, a FAIL family member includes one or more Ig-like domains having an amino acid sequence that is at least about 55%, preferably at least about 65%, more preferably at least 75%, yet more preferably at least about 85%, and most preferably at least about 95% identical to amino acids 120 to 177 and/or amino acids 216 to 273 of SEQ ID NO:3, which are the Ig-like domains of human FAIL (these Ig-like domains are also represented as SEQ ID NO:10 and 11, respectively).

In another embodiment, a FAIL family member includes one or more Ig-like domains having an amino acid sequence that is at least about 55%, preferably at least about 65%, more preferably at least about 75%, yet more preferably at least about 85%, and most preferably at least about 95% identical to amino acids 120 to 177 and/or amino acids 216 to 273 of SEQ ID NO:3, which are the Ig-like domains of human FAIL (these Ig-like domains are also represented as SEQ ID NO:10 and 11, respectively), includes a conserved cysteine residue about 8 residues downstream from the N-terminus of the Ig-like domain, and has one or more Ig-like domain consensus sequences as described herein.

In another embodiment, a FAIL family member includes one or more Ig-like domains having an amino acid sequence that is at least 55%, preferably at least about 65%, more preferably at least about 75%, yet more preferably at least about 85%, and most preferably at least about 95% identical to amino acids 120 to 177 and/or amino acids 216 to 273 of SEQ ID NO:3, which are the Ig-like domains of human FAIL (these Ig-like domains are also represented as SEQ ID NO:10 and 11, respectively), includes a conserved cysteine residue 8 residues downstream from the N-terminus of the Ig-like domain, has one or more Ig-like domain consensus sequences as described herein, and has a conserved cysteine within the consensus sequence that forms a disulfide with said first conserved cysteine.

In yet another embodiment, a FAIL family member includes one or more Ig-like domains having an amino acid sequence that is at least 55%, preferably at least about 65%, more preferably at least about 75%, yet more preferably at least about 85%, and most preferably at least about 95% identical to amino acids 120 to 177 and/or amino acids 216 to 273 of SEQ ID NO:3, which are the Ig-like domains of human FAIL (these Ig-like domains are also represented as SEQ ID NO:10 and 11, respectively), includes a conserved cysteine residue 8 residues downstream from the N-terminus of the Ig-like domain, has one or more Ig-like domain consensus sequences described herein, has a conserved cysteine within the consensus sequence that forms a disulfide with said first conserved cysteine, and has at least one FAIL biological activity as described herein.

In another embodiment, the Ig-like domains of FAIL are Ig domains, which have the following consensus sequence at the C-terminus of the domain: (FY)-Xaa-C-Xaa-(VA)—COO—, wherein (FY) is either a phenylalanine or a tyrosine residue (preferably tyrosine), where "Xaa" is any amino acid, C is a cysteine residue, (VA) is a valine or alanine residue, and COO— is the C-terminus of the domain.

In a preferred embodiment, a FAIL family member has the amino acid sequence of SEQ ID NO:3, wherein the aforementioned Ig-like domain conserved residues are located as follows: the N-terminal conserved cysteine residue is located at amino acid residue position 127 (within the Ig-like domain of SEQ ID NO:3) and the C-terminal conserved cysteine residue is located at amino acid position 175 (within the Ig-like domain of SEQ ID NO:3). In another preferred embodiment, a FAIL family member has the amino acid sequence of SEQ ID NO:3, wherein the aforementioned Ig-like domain conserved residues are located as follows: the N-terminal conserved cysteine residue is located at amino acid residue position 223 (within the Ig-like domain of SEQ ID NO:3) and the C-terminal conserved cysteine residue is located at amino acid position 271 (within the Ig-like domain of SEQ ID NO:3).

Various features of human FAIL are summarized below.

Human Fail

A cDNA encoding human FAIL was identified by analyzing sequences of clones present in a human T cell cDNA library for sequences that encode immunoglobulin (Ig) domains. This analysis led to the identification of a clone, jthtd001g09, encoding full-length FAIL. The human FAIL cDNA of this clone is 1872 nucleotides long (FIGS. 1A–1B; SEQ ID NO:1). The open reading frame of this cDNA, nucleotides 66 to 1175 of SEQ ID NO:1 (SEQ ID NO:2), encodes a 370 amino acid transmembrane protein (FIGS. 1A–B; SEQ ID NO:3) that, as discussed below, is closely related to Fc receptors.

The signal peptide prediction program SIGNALP (Nielsen, et al., 1997, *Protein Engineering* 10: 1–6) predicted that human FAIL includes an 27 amino acid signal peptide (amino acid 1 to about amino acid 27 of SEQ ID NO:3; SEQ ID NO:4) preceding the mature human FAIL protein (corresponding to about amino acid 28 to amino acid 370 of SEQ ID NO:3; SEQ ID NO:5). The molecular weight of human FAIL without post-translational modifications is approximately 40.76 kDa prior to the cleavage of the signal peptide, and approximately 37.73 kDa after cleavage of the signal peptide.

Human FAIL is a transmembrane protein which consists of one or more of the following domains: (1) an extracellular domain; (2) a transmembrane domain; and (3) a cytoplasmic domain. The mature human FAIL protein contains an extracellular domain at amino acid residues 28 to 305 of SEQ ID NO:3 (SEQ ID NO:6), a transmembrane domain at amino acid residues 306 to 325 of SEQ ID NO:3 (SEQ ID) NO:7), and a cytoplasmic domain at amino acid residues 326 to 370 of SEQ ID NO:3 (SEQ ID NO:8).

FIG. 2 depicts a hydropathy plot of human FAIL. Relatively hydrophobic regions of the protein are shown above the horizontal line, and relatively hydrophilic regions of the protein are below the horizontal line. The cysteine residues (cys) and potential N-glycosylation sites (Ngly) are indicated by short vertical lines just below the hydropathy trace. The dashed vertical line separates the signal sequence (amino acids 1 to 27 of SEQ ID NO:3; SEQ ID NO:4) on the left from the mature protein (amino acids 28 to 370 of SEQ ID NO:3; SEQ ID NO:5) on the right.

Human FAIL comprises an immunoglobulin domain sequence at amino acid residues 27 to 80 of SEQ ID NO:3 (SEQ ID NO:9) and two immunoglobulin-like domain sequences at amino acid residues 120 to 177 and 216 to 273 of SEQ ID NO:3 (SEQ ID NO:10 and SEQ ID NO:11, respectively). Three N-glycosylation sites are present in human FAIL. The first N-glycosylation site has the amino acid sequence NQTL (at amino acid residues 60 to 63 of SEQ ID NO:3), the second N-glycosylation site has the amino acid sequence NHSA (at amino acid residues 245 to 248 of SEQ ID NO:3), and the third N-glycosylation site has the amino acid sequence NYSC (at amino acid residues 268 to 271 of SEQ ID NO:3). Human FAIL has a single cAMP phosphorylation site having the amino acid sequence KKLS at amino residues 285 to 288 of SEQ ID NO:3.

Five protein kinase C phosphorylation sites are present in human FAIL. The first protein kinase C phosphorylation site has the amino acid sequence TLR (at amino acid residues 31 to 33 of SEQ ID NO:3), the second protein kinase C phosphorylation site has the amino acid sequence TLR (at amino acid residues 124 to 126 of SEQ ID NO:3), the third protein kinase C phosphorylation site has the amino acid sequence SLK (at amino acid residues 288 to 290 of SEQ ID NO:3), the fourth protein kinase C phosphorylation site has the amino acid sequence SWR (at amino acid residues 327 to 329 of SEQ ID NO:3), and the fifth protein kinase C phosphorylation site has the amino acid sequence TSK (at amino acid residues 350 to 352 of SEQ ID NO:3). Human FAIL has two casein kinase II phosphorylation sites having the amino acid sequences TLQD (at amino acid residues 150 to 153 of SEQ ID NO:3) and SEQD (at amino acid residues 262 to 265 of SEQ ID NO:3).

Four tyrosine kinase phosphorylation sites are present in human FAIL. The first tyrosine kinase phosphorylation site has the amino acid sequence KEGDSGLY (at amino acid residues 166 to 173 of SEQ ID NO:3), the second tyrosine kinase phosphorylation site has the amino acid sequence KSEQDAGNY (at amino acid residues 261 to 269 of SEQ ID NO:3), the third tyrosine kinase phosphorylation site has the amino acid sequence KGKDEGVVY (at amino acid residues 336 to 344 of SEQ ID NO:3), and the fourth tyrosine kinase phosphorylation site has the amino acid sequence KRSEGQFY (at amino acid residues 352 to 359 of SEQ ID NO:3). Human FAIL has seven N-myristylation sites. The first N-myristylation site has the amino acid sequence GQYSCS (at amino acid residues 74 to 79 of SEQ ID NO:3), the second N-myristylation site has the amino acid sequence GSTLVTL (at amino acid residues 120 to 125 of SEQ ID NO:3), the third N-myristylation site has the amino acid sequence GAKEGD (at amino acid residues 164 to 169 of SEQ ID NO:3), the fourth N-myristylation site has the amino acid sequence GLYWCE (at amino acid residues 171 to 176), the fifth N-myristylation site has the amino acid sequence GGTTSL (at amino acid residues 251 to 256 of SEQ ID NO:3), the sixth N-myristylation site has the amino acid sequence GNYSCE (at amino acid residues 267 to 272 of SEQ ID NO:3), and the seventh N-myristylation site has the amino acid sequence GVVYSV (at amino acid residues 341 to 346 of SEQ ID NO:3).

FIG. 3A depicts the alignment between an immunoglobulin domain of human FAIL (otherwise referred to as D1; SEQ ID NO:9) and a typical immunoglobulin domain (SEQ ID NO:12; Accession Number PF00047). FIGS. 3B and 3C depict alignments of two immunoglobulin-like domains of human FAIL (otherwise referred to as D2 and D3; SEQ ID NOS:10 and 11) and a typical immunoglobulin domain (SEQ ID NO:12; Accession Number PF00047).

Figure 4B:
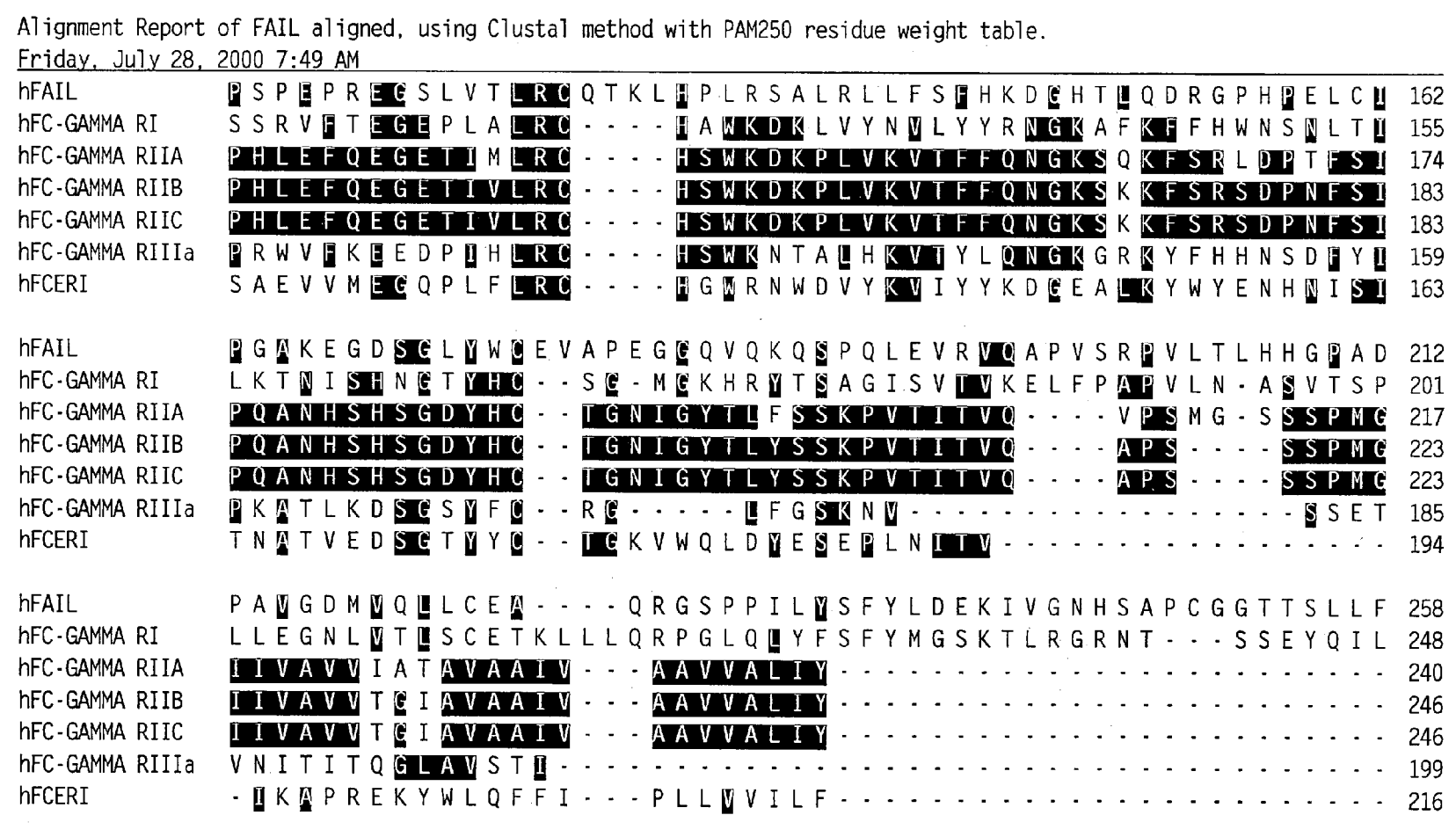

Human FAIL has homology to various Fc receptors (FcRs; FIGS. 4A–4C). (See, e.g., Daeron, 1997, Annu. Rev. Immunol. 15:203–234 for a review of Fc receptors.) However, human FAIL has the highest homology to the alpha subunit of human FcγRI. FIGS. 5A–5B show an alignment of the human FAIL coding region (SEQ ID NO:2) and the alpha subunit of human FcγRI coding region (SEQ ID NO:13; GenBank Accession No. X14355). The human FcγRI has been shown to bind to IgG antibodies and play an important role in the regulation of the immune response. The nucleotide sequences of coding regions of human FcγRI and human FAIL are 28.7% identical. FIG. 6 shows that there is an overall 22.7% identity between the amino acid sequence of the human FAIL protein (SEQ ID NO:3) and the amino acid sequence of the alpha subunit of human FcγRI (SEQ ID NO:14).

The alpha subunit of Fc receptors are characterized by the presence of Ig and Ig-like domains. The Ig domain D1 of human FAIL is 17.3% identical to FcγRI D1, 37% identical to FcγRI D2, and 16.7% identical to FcγRI D3, 21.1% identical to FcεRI D1, and 42.6% identical to FcεRI D2. The Ig-like domain D2 of human FAIL is 23.1% identical to FcγRI D1, 16.7% identical to FcγRI D2, and 50% identical to FcγRI D3, 25% identical to FcεRI D1, and 25.9% identical to FcεRI D2.

Fc receptors recognize and bind to the Fc portion of antibodies. FcR aggregation resulting from the antibody-FcR interaction triggers intracellular signal transduction pathways and ultimately results in downstream cellular responses. Depending upon the FcR expressed by the cells, the antibody-FcR interaction will elicit cell activation, endocytosis and/or phagocytosis, or negatively regulate cell activation. FcRs are generally multichain receptors composed of various subunits including, e.g., a ligand-binding subunit and one or more signal transduction subunits. The aggregation of the particular subunits of the multichain receptor in response to antibody determines what type of downstream cellular response is induced. Each class of antibody has an FcR, e.g., FcγR binds IgG, FcβR binds IgA, FcεR binds IgE, FcμR binds IgM and FcγR binds IgD. To date, the FcR, FcμR, for IgM, has not been cloned. For review of FcRs see, e.g., Daëron, M., 1997, Annu. Rev. Immunol. 15:203–234, Ravetech et al., 1998, Annu. Rev. Immunol. 16:421–432, Buck, C. A., 1992, Seminars in Cell Biology 3:179–188, and Heyman, B., 2000, Annu. Rev. Immunol. 18:709–737.

Figure 7:
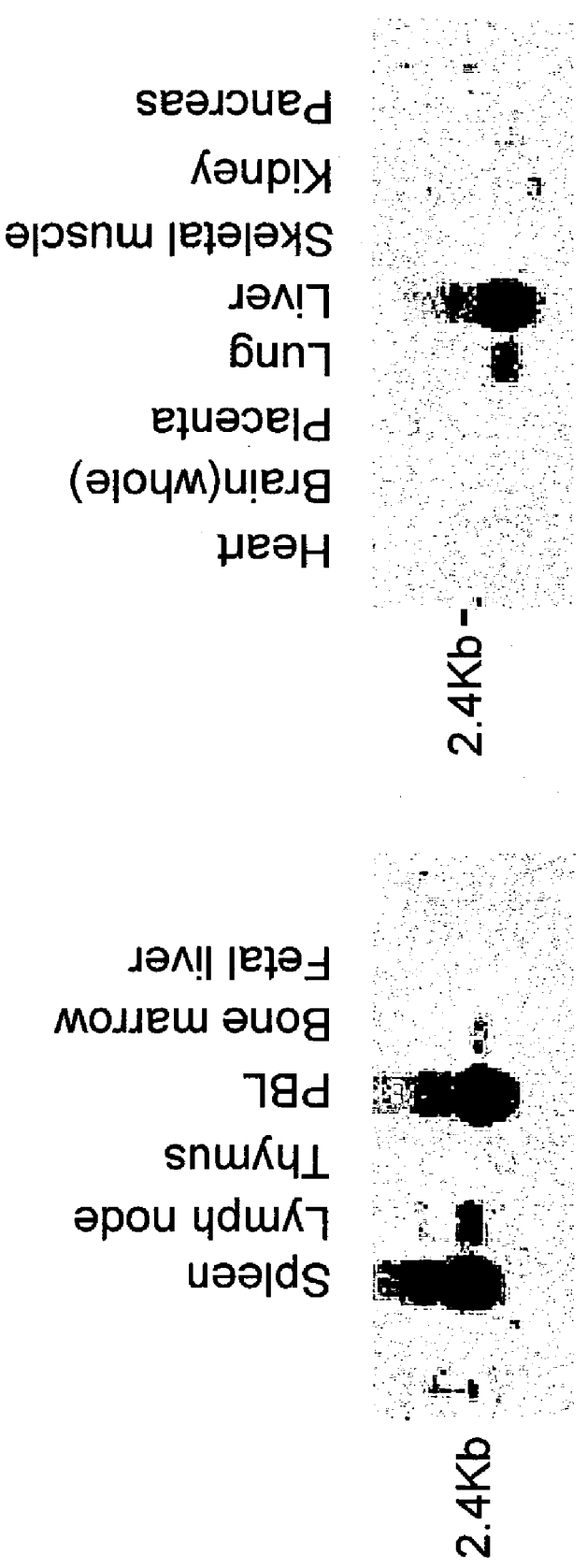
FIG. 7: Northern blot analysis of human tissues. A 2.4 and 3.0 kb transcript was observed in liver, lung, spleen, and peripheral blood leucocytes (PBL). No signal was observed in heart, brain (whole), skeletal muscle, kidney, pancreas, thymus, or fetal liver.

Human FAIL expression was detected in the liver and to a lesser extent the lung by Northern blot analysis (FIG. 7). However, human FAIL expression was not detected by Northern blot analysis in the heart, brain (whole), skeletal muscle, kidney or pancreas. Human FAIL expression was detected in the spleen, peripheral blood leukocytes (PBLs), lymph node and bone marrow using the Clonetech Multiple Tissue Northern Blot (Palo Alto, Calif.; FIG. 7). An intense 2.4 kb band and a less intense 3.0 kb band was detected in spleen and PBLs. Lower levels of the 2.4 kb and 3.0 kb band were detected in the lymph node and bone marrow. Human FAIL expression was not detected in the thymus and fetal liver using the Clonetech Multiple Tissue Northern Blot. The results from the Clonetech Multiple Tissue Northern blot indicate that FAIL is expressed primarily in the lymphoid tissues.

Clone EpFAIL, which encodes human FAIL, was deposited with the American Type Culture Collection (10801 University Boulevard, Manassas, Va. 20110-2209) on Jul. 21, 2000 and assigned patent deposit Number PTA-2266. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

FAIL Gene Expression Analysis

Total RNA was prepared from various human tissues by a single step extraction method using RNeasy Mini Kit according to the manufacturer's instructions (Qiagen, Inc.). Each RNA preparation was treated with DNase I (Qiagen) at room temperature for 15 minutes. DNAse I treatment was determined to be complete if the sample required at least 38 PCR amplification cycles to reach a threshold level of fluorescence using ÿ-2 microglobulin as an internal amplicon reference. The integrity of the RNA samples following DNase I treatment was confirmed by agarose gel electrophoresis and ethidium bromide staining. Next, the cDNA was prepared from the sample using the SUPERSCRIPT™ Choice System following the manufacturer's instructions (Qiagen, Inc.). A negative control of RNA without reverse transcriptase was mock reverse transcribed for each RNA sample.

FAIL expression was measured by TaqMan® quantitative PCR (Perkin Elmer Applied Biosystems) in cDNA prepared from the following human tissues and cells: kidney, lymph node, spleen, brain, lung, liver, tonsil, colon, and heart; resting CD4+ cells or CD4+ cells stimulated 4 or 24 hours with anti-CD3 antibody or anti-CD3 in combination with anti-CD28 antibody; CD8+ cells stimulated 4 or 24 hours with anti-CD3 antibody or anti-CD3 in combination with anti-CD28 antibody; resting CD14+ cells or CD14+ cells stimulated 4 or 24 hours with TNF-α or lipopolysaccharide (LPS); resting macrophages (MACs) or MACs stimulated 4 or 24 hours with TNF-α or LPS; immature dendritic cells (DC) treated for 6 or 24 hours with LPS; mature dendritic cells treated for 6 or 24 hours with a combination of LPS, IL-1β and TNF-α; mature dendritic cells (DC) treated for 6 or 24 hours with a combination of LPS, IL-1β, TNF-α, and IFN-γ; mature dendritic cells (DC) treated for 6 or 24 hours with a combination of LPS, IL-1β, TNF-α, and PGE2; mature dendritic cells (DC) treated for 6 or 24 hours with poly I:C; mature dendritic cells (DC) treated for 6 or 24 hours with CD40 ligand; resting tonsillar CD19+ cells or CD19+ cells stimulated with LPS or CD40 ligand; resting granulocytes (Grans) or Grans stimulated 4 or 24 hours with TNF-α or IFN-γ; resting eosinophils (Eos) or Eos stimulated 4 or 24 hours with IL-4; Th0, Th1, and Th2 cells; resting fibroblastic synoviocytes from rheumatoid arthritis (RA synovio type B) or RA synovio type B stimulated 4 or 24 hours with TNF-α, IFN-γ, or IL-1; resting normal human bronchial epithelium (NHBE) or NHBE stimulated 4 or 24 hours with IL-4, IL-13, or the combination of IL-4 and IL-13; resting bronchial smooth muscle cells (BSMC) or stimulated 4 or 24 hours with TNF-α, IFN-γ, or IL-1; resting human microvascular endothelial cells (HMVEC) or stimulated 4 or 24 hours with TNF-α, IFN-γ, or IL-1; resting normal human lung fibroblasts (NHLF) or stimulated 4 or 24 hours with TNF-α or TGF-β; resting normal human dermal fibroblasts (NHDF) or stimulated 4 or 24 hours with TNF-α or TGFβ; resting normal human dermal fibroblasts (HDF) or stimulated 4 or 24 hours with TNF-α or IL-1; normal synovium or synovium from rheumatoid arthritis patients; lung tissue pooled from patients with chronic obstructive pulmonary disease (COPD-1 and COPD-2); and lung tissue pooled from patients with idiopathic pulmonary fibrosis (IPF). PCR probes were designed by PrimerExpress software (PE Biosystems) based on the disclosed sequence of FAIL. The primers and probes used were as follows:

```
FAIL Forward Primer:
CTCCAAGAACCCCTTAGCGA            (SEQ ID NO:35)

FAIL Reverse Primer:
GGTGGGCGTGTGTTGATAGG            (SEQ ID NO:36)

FAIL TaqMan Probe:
TGTGAGGAGGTTCTCTGCTAGTGATGGTGTT (SEQ ID NO:37)

β2-microglobulin Forward Primer:
CACCCCCACTGAAAAAGATGA           (SEQ ID NO:38)

β2-microglobulin Reverse Primer:
CTTAACTATCTTGGGCTGTGACAAAG      (SEQ ID NO:39)

β2-microglobulin TaqMan Probe:
ATGCCTGCCGTGTGAACCACGTG         (SEQ ID NO:40)
```

The FAIL gene probe was labeled using FAM (6-carboxyfluorescein), and the β2-microglobulin reference probe was labeled with a different fluorescent dye, VIC. The differential labeling of the target gene and internal reference gene thus enabled measurement in same well. Forward and reverse primers and the probes for both β2-microglobulin and the FAIL gene were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β2-microglobulin and 600 nM forward and reverse primers plus 200 nM probe for the target gene. TaqMan® matrix experiments were carried out using an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate FAIL gene expression in the various tissues relative to β2-microglobulin expression in the same tissue. The threshold cycle (Ct) value is defined as the cycle at which a statistically significant increase in flourescence is detected. A lower Ct value is indicative of a higher mRNA concentration. The Ct value of the kinase gene is normalized by subtracting the Ct value of the β2-microglobulin gene to obtain a Ct value using the following formula: $Ct=Ct_{kinase} - Ct_{\beta-2\ microglobulin}$. Expression is then calibrated against a well containing a nontemplate control, e.g., water. The Ct value for the calibrator sample is then subtracted from Ct for each tissue sample according to the following formula: $Ct=Ct\text{-}sample - Ct_{calibrator}$. Relative expression is then calculated using the arithmetic formula given by 2-Ct. Expression of the FAIL gene in each of the tissues tested is then graphically represented in FIGS. 8A–8B.

Figure 8A:
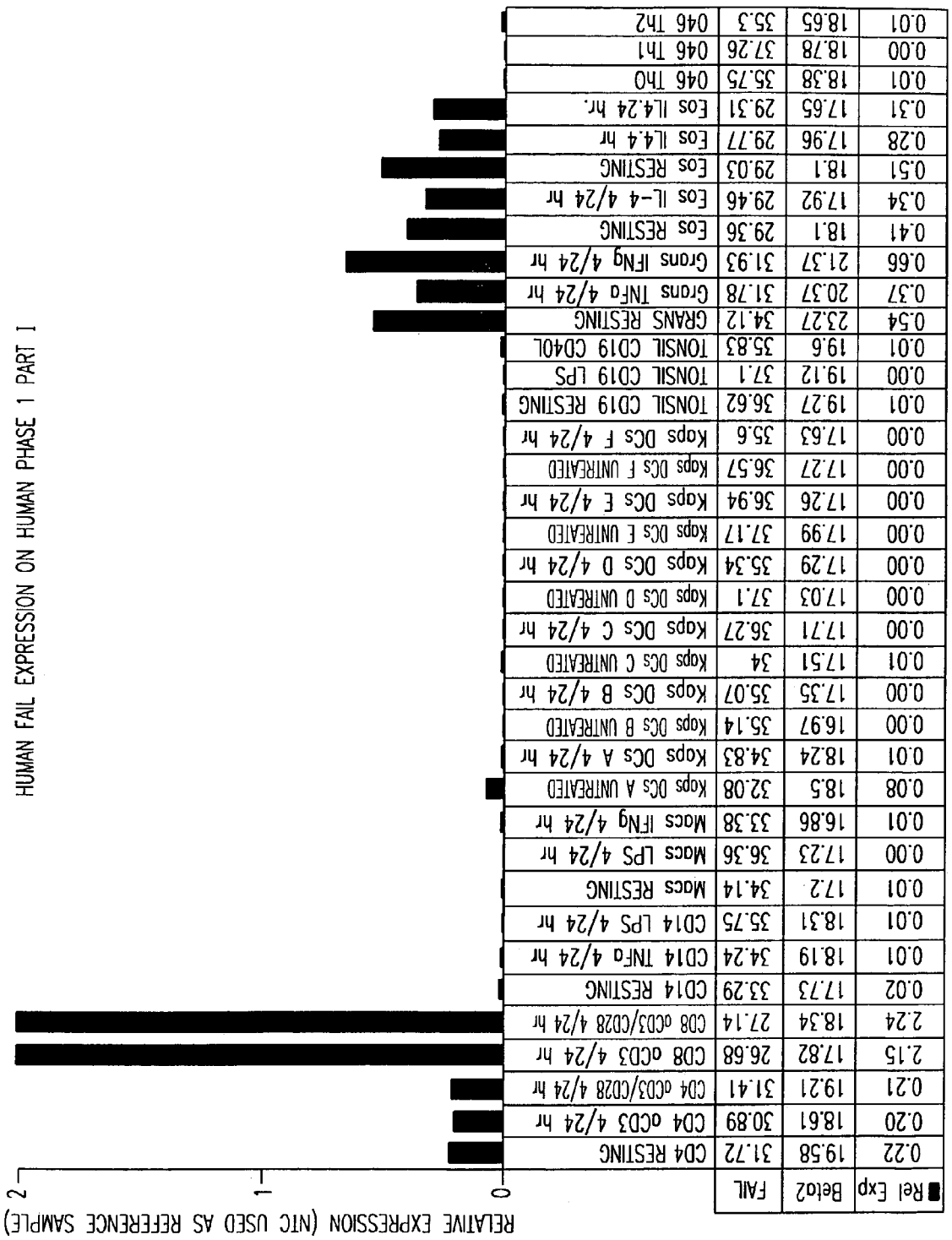
FIGS. 8A–8B: Human FAIL expression in various tissues and cells as measured by TaqMan® quantitative PCR.
Figure 8B:
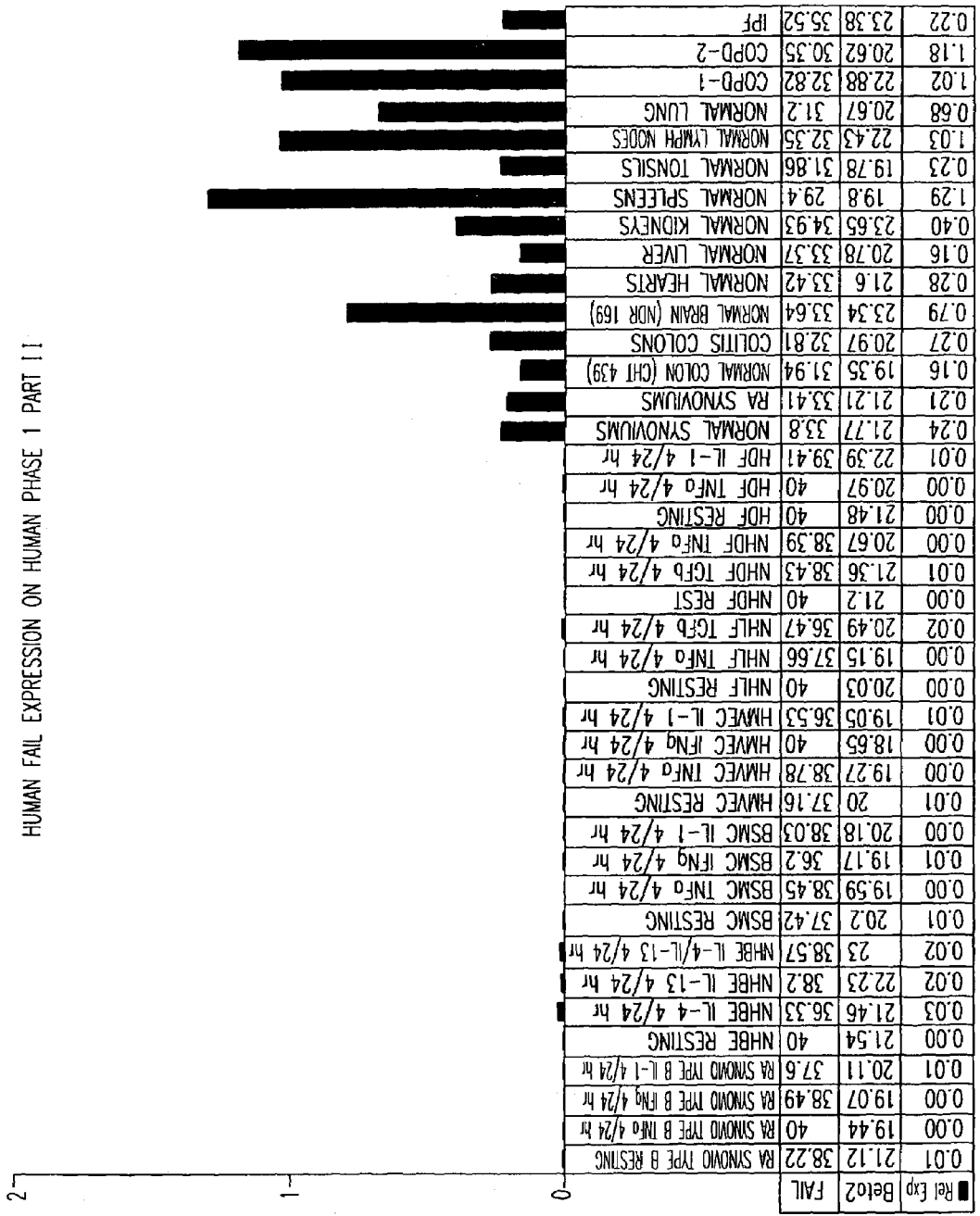

FAIL expression was detected on the following cell types: CD4+ resting T cells, anti-CD3 antibody stimulated CD4+ T cells, anti-CD3 antibody and anti-CD28 antibody stimulated CD4+ T cells, anti-CD3 antibody stimulated CD8+ T cells, anti-CD3 antibody and anti-CD28 antibody stimulated CD8+ T cells, resting granulocytes, TNF-α stimulated granulocytes, IFN-γ stimulated granulocytes, resting eosinophils, and IL-4 stimulated eosinophils (FIGS. 8A–8B). The highest levels of FAIL expression were detected in CD8+ T cells stimulated with anti-CD3 antibody or anti-CD3 antibody and anti-CD28 antibody. FAIL expression was also detected in the following tissues: normal brain, normal heart, normal liver, normal spleen, normal lymph node, normal colon, normal tonsils, normal kidneys, and normal lung (FIGS. 8A–8B). Further, FAIL expression was detected in biological samples from patients with rheumatoid arthritis, IPF, COPD-1 and COPD-2 (FIG. 8).

Uses of FAIL Nucleic acids, Polypeptides, and Modulators Thereof

FAIL nucleic acids and proteins can be utilized as a marker (e.g., an in situ marker) for identification, isolation, depletion, and/or tracking of immune cells (e.g., T cells, B cells, natural killer cells, dendritic cells, granulocytes, eosinophils, and mast cells) in a sample. FAIL proteins and nucleic acids encoding FAIL proteins can be utilized as antigens to make antibodies that can, in turn, be used for identification, isolation, depletion, and/or tracking of the immune cells (e.g., T cells, B cells, natural killer cells, dendritic cells, and mast cells) or FAIL in a sample, or to track immune disorders such as immune proliferative disorders (e.g., carcinoma, lymphoma, e.g., follicular lymphoma), disorders associated with fighting pathogenic infections (e.g., bacterial (e.g., chlamydia) infection, parasitic infection, and viral infection (e.g., HSV or HIV infection)), pathogenic disorders (e.g., immunodeficiency disorders, such as HIV), autoimmune disorders (e.g., arthritis, graft rejection, multiple sclerosis, Grave's disease, and Hashimoto's disease), T cell disorders (e.g., AIDS), septicemia, cerebral malaria, inflammatory bowel disease (e.g., Crohn's disease and ulcerative colitis), inflammatory disorders (e.g., rheumatoid arthritis and osteoarthritis), allergic inflammatory disorders (e.g., IgE mediated disorders, asthma and psoriasis), apoptotic disorders (e.g., rheumatoid arthritis, systemic lupus erythematosus, and insulin-dependent diabetes mellitus), cytotoxic disorders, septic shock, chronic obstructive pulmonary disease (COPD; e.g., emphysema and chronic bronchitis, bronchial asthma, and bronchiectasis), and cachexia. Further, FAIL nucleic acids can also be utilized for chromosomal mapping, or as chromosomal markers, e.g., in radiation hybrid mapping.

As FAIL was originally found in a T cell library, FAIL nucleic acids, proteins, and modulators thereof can be used to modulate the proliferation, development, differentiation, and/or function of immune cells (e.g., T cells, B cells, dendritic cells, natural killer cells and monocytes), and/or immune function. FAIL nucleic acids, proteins and modulators thereof can be utilized to modulate immune-related processes, e.g., the host immune response by, for example, modulating the formation of and/or binding to immune complexes and immune surveillance for rapid removal or pathogens.

FAIL nucleic acids, proteins and modulators thereof can be utilized to modulate or treat immune disorders that include, but are not limited to, immune proliferative disorders (e.g., carcinoma, lymphoma, e.g., follicular lymphoma), disorders associated with fighting pathogenic infections (e.g., bacterial (e.g., chiamydia) infection, parasitic infection, and viral infection (e.g., HSV or HIV infection)), pathogenic disorders (e.g., immunodeficiency disorders, such as HIV), autoimmune disorders (e.g., arthritis, graft rejection, multiple sclerosis, Grave's disease, and Hashimoto's disease), T cell disorders (e.g., AIDS), septicemia, cerebral malaria, inflammatory bowel disease (e.g., Crohn's disease and ulcerative colitis), inflammatory disorders (e.g., rheumatoid arthritis and osteoarthritis), allergic inflammatory disorders (e.g., IgE mediated disorders, asthma and psoriasis), apoptotic disorders (e.g., rheumatoid arthritis, systemic lupus erythematosus, and insulin-dependent diabetes mellitus), cytotoxic disorders, septic shock, chronic obstructive pulmonary disease (COPD; e.g., emphysema and chronic bronchitis, bronchial asthma, and bronchiectasis), and cachexia.

As FAIL has homology to the human FcγRI, FAIL nucleic acids and polypeptides can be utilized to bind to the Fc portion of antibodies (e.g., the Fc portion of IgG, IgM, IgE and/or IgA) and to modulate immune responses such as immune cell activation (e.g., activation of T-cells or natural killer cells). Preferably, FAIL nucleic acids and polypeptides are utilized bind to the Fc portion of an IgM antibody and to modulate immune responses. FAIL nucleic acids, proteins and modulators thereof can be utilized to modulate the interaction between an Fc receptor (e.g., FcµR, FcγRI or FcεRI) and an antibody (e.g., IgM or IgG). Preferably, FAIL nucleic acids, protein and modulators thereof are utilized to modulate the interaction between FcµR and IgM antibody, and thus modulate the immune response.

FAIL nucleic acids, proteins and modulators thereof can be utilized to modulate immune activation. For example, antagonists of FAIL action, such as peptides, antibodies or small molecules that decrease or block FAIL activity, e.g., by binding to immunoglobulin domains, or that prevent FAIL signaling, can be used as immune system activation blockers. In another example, agonists that mimic or partially mimic FAIL activity, such as peptides, antibodies or small molecules, can be used to induce immune system activation. Antibodies may activate or inhibit cell adhesion, proliferation and activation, and may help in treating infection, autoimmunity, inflammation, and cancer by affecting these cellular processes. FAIL nucleic acids, proteins and modulators thereof can also be utilized to modulate intercellular signaling in the immune system, e.g., by modulating intercellular signal transduction in immune stimulation or suppression, or by modulating immune cell membrane adhesion to extracellular matrix (ECM) components during development, e.g., late stages of development.

As FAIL is a transmembrane protein, FAIL nucleic acids, proteins and modulators thereof can be utilized to modulate intracellular signaling cascades (e.g., the activation of Syk, Lyn, Zap-70, phosphatidylinositol 3-kinase, protein kinase C., and PLC(2).

FAIL polypeptides, nucleic acids, and modulators thereof, can be used to modulate the function, morphology, proliferation and/or differentiation of cells in the tissues in which it is expressed (e.g., the spleen, liver, lung, lymph nodes, peripheral blood lymphocytes and bone marrow). Thus, FAIL polypeptides, nucleic acids, and modulators thereof can be used to treat disorders such as asthma, bronchitis, bronchiolitis, cystic fibrosis, sacrcoidosis, idiopathic pulmonary fibrosis, hypersensitivity pneumontis, pneumonia, emphysema, lung cancer, jaundice, hepatic failure, hereditary hyperbiliruinemias (e.g., Gilbert's syndrome, Crigler-Naijar syndromes and Dubin-Johnson and Rotor's syndromes), hepatic circulatory disorders (e.g., hepatic vein thrombosis and portal vein obstruction and thrombosis), hepatitis (e.g., chronic active hepatitis, acute viral hepatitis, and toxic and drug-induced hepatitis), cirrhosis (e.g., alcoholic cirrhosis, biliary cirrhosis, and hemochromatosis), malignant tumors (e.g., primary carcinoma, hepatoma, hepatoblastoma, liver cysts, and angiosarcoma), hepatic vein thrombosis, lymphoma, leukemia, colon cancer, amyloidosis, scleroderma, mastocytosis, ulcerative colitis, Crohn's disease, splenic lymphoma, splenomegaly, phagocytotic disorders, acute myeloid leukemia, hemophilia, leukemia, anemia (e.g., sickle cell anemia), and thalassemia.

Further, as FAIL includes immunoglobulin domains and has homology to human FcγRI, FAIL polypeptides, nucleic acids, and modulators thereof can be used to treat disorders involving an immune, allergic or autoimmune response (e.g., arthritis, multiple sclerosis, meningitis, encephalitis, atherosclerosis, or infection).

Assays for the Detection of FAIL Expression or Activity

The expression of FAIL can be readily detected, e.g., by quantifying FAIL protein and/or RNA. Many methods standard in the art can be thus employed, including, but not limited to, immunoassays to detect and/or visualize gene expression (e.g., Western blot, immunoprecipitation followed by sodium dodecyl sulfate polyacrylamide gel electrophoresis (SDS-PAGE), immunocytochemistry, etc.) and/or hybridization assays to detect gene expression by detecting and/or visualizing, respectively, mRNA encoding a gene (e.g., Northern assays, dot blots, in situ hybridization, etc.), etc. The ability of FAIL to bind to antibodies or fragments thereof (e.g., the Fc portion of antibodies) can readily be detected using techniques known to those of skill in the art.

The activity of a FAIL protein can be measured by employing methods known to those of skill in the art. For example, the activity of a FAIL protein can be analyzed by treating T cells or FAIL-transfected cells with antibody or a fragment thereof (e.g., the Fc portion of an antibody) and measuring the effect of such treatment on the level of tyrosine phosphorylation of signaling molecules, such as FcR β and γ subunits, Syk, Lck, Fyn, Zap-70, PLC-γ1 phosphatidylinositol 3-kinase, and Lyn (e.g., tyrosine phosphorylation can be detected by immunoprecipitation followed by SDS-PAGE, kinase assays, etc.). The activity of a FAIL protein can also be analyzed by measuring changes in the concentration of free intracellular $Ca^{2+}$ induced by the treatment of T cells or FAIL-transfected cells with antibody or a fragment thereof (e.g., the Fc portion of an antibody). Briefly, T cells or FAIL-transfected cells are incubated with fura-2 fluorescence at 37° C. and, then incubated with 2 mM $CaCl_2$ prior to incubation with antibody or a fragment thereof (e.g., the Fc portion of an antibody). The cells are lysed in lysis buffer, and the concentration of free intracellular $Ca^{2+}$ is measured by fluorescence at 37° C. using a spectrophotometer (see, e.g., Jandrot-Perrus et al., 1997, J. of Biol. Chem. 272:27035–27041).

The activity of a FAIL protein can also be analyzed by measuring T cell activation, proliferation, endocytosis, and phagocytosis using techniques known to those of skill in the art. For example, T cell activation can be measured by assessing the expression of T cell activation markers such as CD28 and ICOS, and T cell proliferation can be measured using 3H-thymidine uptake assays. Further, the activity of a FAIL protein can be analyzed by measuring the expression of such molecules as histamine, antibodies (e.g., IgG, IgM, IgA, and IgE), and cytokines (e.g., IFN-α, IFN-β, IFN-γ, IL-2, IL-4, IL-5, IL-6, IL-10, IL-12, IL-15, and IL-18) using techniques known to those of skill in the art. For example, cytokine expression can be measured by RT-PCR and immunoassays such as ELISAs.

Such assays may be utilized as part of FAIL diagnostic assays. In addition, such assays may be utilized as part of screening methods for identifying compounds that modulate the activity and/or expression of FAIL.

Assays for Analysis of FAIL Modulators

A variety of assays can be utilized to analyze a FAIL protein, nucleic acid or modulator thereof. Such assays include, e.g., in vivo, ex vivo and in vitro assays, as described herein.

For example, in view of the fact that FAIL is a cell surface receptor, in particular, an FcR, standard quantitative binding studies can be utilized to measure modulator binding to T cells. (See, e.g., Horton (ed), 1995, Adhesion Receptors as Therapeutic Targets, Chapter 15, CRC Press, Inc.: London, United Kingdom.) Such binding assays can also be utilized to perform receptor blockade studies to measure the number of cellular sites available for binding modulator by comparing the number of molecules of labeled modulator molecules (e.g., labeled anti-FAIL antibodies) bound per immune cell (e.g., T cell) at a series of concentrations with the number of modulator molecules bound at saturation.

The activation of signal transduction pathways can be analyzed in in vitro and ex vivo assays using assays known to those of skill in the art. For example, the activation of signal transduction pathways in vitro can be analyzed by contacting immune cells such as T cells or FAIL-transfected cells with a FAIL modulator (e.g., IgG, IgE, IgM or a fragment thereof) or a control (e.g., PBS) and measuring the effect of such treatment on the level of tyrosine phosphorylation of signaling molecules, such as FcR β and γ subunits, Syk, Lck, Fyn, Zap-70, PLC-γ1, phosphatidylinositol 3-kinase, and PKC (e.g., tyrosine phosphorylation can be detected by immunoprecipitation followed by SDS-PAGE, kinase assays, etc.). In an ex vivo assay, the activation of signal transduction pathways can be analyzed by contacting immune cells (e.g., T cells) obtained from individuals treated with a FAIL modulator or a placebo and measuring the effect of such treatment on the level of tyrosine phosphorylation of signaling molecules, such as FcR β and γ subunits, Syk, Lck, Fyn, Zap-70, PLC-γ1, phosphatidylinositol 3-kinase, and PKC (e.g., tyrosine phosphorylation can be detected by immunoprecipitation followed by SDS-PAGE, kinase assays, etc.). The effect of FAIL modulators on calcium mobilization can also be analyzed by measuring changes in the concentration of free intracellular $Ca^{2+}$ induced in in vitro and ex vivo assays using assays known to those of skill in the art.

The efficacy of FAIL modulators can be assessed in a variety of animal models including, but not limited to, mice overexpressing a particular type of antibody (e.g., IgG, IgM, IgA or IgE), mice expressing low levels or undetectable levels (e.g., by western blot or RT-PCR) of a particular antibody (e.g., IgG, IgM, IgA or IgE), mice deficient in a particular type of immune cell (e.g., T cells, natural killer cells, B cells, granulocytes, eosinophils, monocytes, or macrophages), and mice overexpressing of a complement component, and mice expressing undetectable levels (e.g., by western blot analysis or RT-PCR) of a complement component. The efficacy of FAIL modulators can also be tested in such autoimmune disorder models as an experimental allergic encephalomyelitis (EAE) model. EAE is an experimental autoimmune disease of the central nervous system (CNS) (Zamvil et al, 1990, Ann. Rev, Immunol. 8:579) and is a disease model for the human autoimmune condition, multiple sclerosis (MS). EAE is an example of a cell-mediated autoimmune disorder that is mediated via T cells. EAE is readily induced in mammalian species by immunizations of myelin basic protein (MBP) purified from the CNS or an encephalitogenic proteolipid (PLP). SJL/J mice are a susceptible strain of mice ($H-2^u$) and, upon induction of EAE, these mice develop an acute paralytic disease and an acute cellular infiltrate is identifiable within the CNS. EAE spontaneously develops in $MBP_{1-17}$ peptide-specific T cell receptor (TCR) transgenic mice ($TgMBP^+$) of a RAG-1-deficient background (Lafaille et al., 1994, Cell 78:399).

A collagen-induced arthritis (CIA) model can also be utilized to determine the efficacy of FAIL modulators. CIA is an animal model for the human autoimmune disease rheumatoid arthritis (RA) (Trenthorn et al., 1977, J. Exp. Med. 146:857). This disease can be induced in many species by the administration of heterologous type II collagen (Courtenay et al., 1980, Nature 283:665; and Cathcart et at, 1986, Lab. Invest. 54:26). With respect to animal models of arthritis see, in addition, e.g., Holmdahl, R., 1999, Curr. Biol. 15:R528–530.

Animal models for chronic obstructive pulmonary disease (COPD) can also be used to determine the efficacy of FAIL modulators (for review of COPD animal models see, e.g., Shapiro, 2000, Am. J. Respir. Cell Mol. Biol. 22:4–7; and Shapiro, 2000, Chest 117:2223S–227S). COPD is a generic term for several clinical syndromes including, but not limit to, emphysema and chronic bronchitis. Emphysema can be induced in animals such as mice by the administration or overexpression of elasolytic enzymes including, but not limited to pancreatic elastase, neutrophil elastase, and proteinase 3. Emphysema can also be induced by the administration of a variety of chemicals and irritants including, but not limited to, lipopolysaccharides (LPS), cadmium chloride, nitrogen dioxide, inorganic dust, and ozone. Further, emphysema can be induced by overexpression of interferon-((IFN-( ). Cigarette smoke-related COPD in mice can be induced by chronic exposure to cigarette smoke. Pulmonary fibrosis can be induced by the administration of bleomycin to mice. Further, mutant mouse strains such as tight skin (Tsk$^{+/-}$), pallid (pa/pa), blotchy (Blo), mice transgenic for collagenase, and PDGF-A$^{-/-}$ that spontaneously develop enlarged airspaces can also be used to determine the therapeutic efficacy of FAIL modulators.

Animal models for inflammatory bowel disease (IBD) can also be used to determine the efficacy of FAIL modulators (for review see, e.g., Kim et al., 1992, Scand. J. Gastroentrol. 27:529–537; and Strober, 1985, Dig. Dis. Sci. 30 (12 Suppl.):3S–10S. Crohn's disease and ulcerative colitis are two types of human IBDs. IBD can be induced in animals by oral administration of sulfated polysaccharides including, but not limited to, carrageenan, amylopectin sulfate, and dextran sulfate. IBD can also be induced by the administration of chemical irritants such as trinitrobenzenesulphonic acid (TNBS) and acetic acid.

Further, animal models such as the adoptive transfer model described, e.g., in L. Cohn et al., 1997, J. Exp. Med. 186:1737–1747 can be used to determine the efficacy of FAIL modulators. In such an animal system, aeroallergen provocation of TH1 or TH2 recipient mice results in TH effector cell migration to the airways and is associated with an intense neutrophilic (TH1) and eosinophilic (TH2) lung mucosal inflammatory response. The animal model represents an accepted model for asthma.

Still further, animal models for type 1 diabetes, thyroid autoimmunity or systemic lupus erythematosus, including glomerulonephritis can be utilized to determine the efficacy of FAIL modulators (see, e.g., Flanders et al., 1999, Autoimmunity 29:235–246; Krogh et al., 1999, Biochimie 81:511–515; and Foster, N.H., 1999, Semin. Nephrol. 19:12–24, respectively).

Tables 1 and 2 below provide a summary of the sequence information for FAIL.

TABLE 1

Summary of FAIL Sequence Information

| Gene | CDNA | ORF | Figure | Patent Deposit No. |
|---|---|---|---|---|
| Human FAIL | SEQ ID NO:1 | SEQ ID NO:2 | FIG. 1 | 2266 |

Various aspects of the invention are described in further detail in the following subsections:

Isolated Nucleic Acid Molecules

One aspect of the invention pertains to isolated nucleic acid molecules that encode a polypeptide of the invention, as well as nucleic acid molecules sufficient for use as hybridization probes to identify the presence or level of nucleic acid molecules encoding a polypeptide of the invention, including nucleic acid molecules suitable for use as PCR primers for the amplification or mutation of nucleic acid molecules.

As used herein, the term "nucleic acid molecule" is intended to include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acid molecule can be single-stranded, double-stranded, may contain both single-stranded and double-stranded portions, and may contain triple-stranded portions, but preferably is double-stranded DNA. In one embodiment, the nucleic acid molecules of the invention comprise a contiguous open reading frame encoding a polypeptide of the invention, e.g., a cDNA molecule, or the open reading frame of a polypeptide of the invention as present on a cDNA molecule.

An "isolated" nucleic acid molecule is one which is separated from other nucleic acid molecules which are present in the natural source of the nucleic acid molecule. Preferably, an "isolated" nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. The term "isolated" nucleic acid molecule can refer to a nucleic acid molecule of the invention that lacks intron sequences, such as a cDNA molecule. Moreover, an "isolated" nucleic acid

TABLE 2

Summary of Domains of FAIL Proteins

| Protein | Signal Sequence | Mature Protein | Extracellular Domain | Ig Domain | Ig-like Domain | Transmembrane Domain | Cytoplasmic Domain |
|---|---|---|---|---|---|---|---|
| HUMAN FAIL | aa 1–27 of SEQ ID NO:3 (SEQ ID NO:4) | aa 28–370 of SEQ ID NO:3 (SEQ ID NO:5) | aa 28–305 of SEQ ID NO:3 (SEQ ID NO:6) | aa 27–80 of SEQ ID NO:3 (SEQ ID NO:9) | Aa 120–177; 216–273 of SEQ ID NO:3 (SEQ ID NO:10; SEQ ID NO:11) | aa 306–325 of SEQ ID NO:3 (SEQ ID NO:7) | aa 326–370 of SEQ ID NO:3 (SEQ ID NO:8) | molecule can be substantially free of other cellular material, or culture medium when produced by recombinant techniques, or substantially free of chemical precursors or other chemicals when chemically synthesized. As used herein, the term "isolated" when referring to a nucleic acid molecule does not include an isolated chromosome.

A nucleic acid molecule of the present invention, e.g., a nucleic acid molecule comprising the nucleotide sequence of SEQ ID NO:1, 2, 15, 16, 17, 18, 19, 20, 21, 22, 23, 24, 25, 26, 27, 28, or 29, or a complement thereof, can be isolated using standard molecular biology techniques and the sequence information provided herein. Using all or a portion of the nucleic acid sequences of SEQ ID NO:1, 2, 15, 16, 17, 18, 19, 20, 21, 22, 23, 24, 25, 26, 27, 28, or 29 as a hybridization probe, nucleic acid molecules of the invention can be isolated using standard hybridization and cloning techniques (e.g., as described in Sambrook et al., eds., *Molecular Cloning: A Laboratory Manual, 2nd ed., Cold Spring Harbor Laboratory*, Cold Spring Harbor Laboratory Press, Cold Spring Harbor, N.Y., 1989).

A nucleic acid molecule of the invention can be amplified using, for example, cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which is a complement of the nucleotide sequence of SEQ ID NO:1, 2, 15, 16, 17, 18, 19, 20, 21, 22, 23, 24, 25, 26, 27, 28, or 29, or the nucleotide sequence of the cDNA insert of a EpFAIL clone deposited with the ATCC® as patent deposit Number PTA-2266, or a portion thereof. A nucleic acid molecule which is complementary to a given nucleotide sequence is one which is sufficiently complementary to the given nucleotide sequence that it can hybridize to the given nucleotide sequence, thereby forming a stable duplex, under one of the hybridization conditions discussed herein. In one embodiment, the complementary nucleic acid molecule is 100% complementary to the nucleotide sequence with which it forms the stable duplex. In another embodiment, the complementary nucleic acid molecule is complementary over its entire length to the nucleotide sequence with which it forms the stable duplex. In yet another embodiment, the nucleotide sequence forms a stable duplex over its entire length with the complementary nucleic acid molecule of the invention.

Moreover, a nucleic acid molecule of the invention can comprise only a portion of a nucleic acid sequence encoding a full length polypeptide of the invention, for example, a fragment which can be used as a probe or primer or a fragment encoding a biologically active portion of a polypeptide of the invention. The nucleotide sequence determined from the cloning of one gene allows for the generation of probes and primers designed for use in identifying and/or cloning homologs in other cell types, e.g., from other tissues, as well as homologs from other mammals. The probe/primer typically comprises substantially purified oligonucleotide. In one embodiment, the oligonucleotide comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, 2, 15, 16, 17, 18, 19, 20, 21, 22, 23, 24, 25, 26, 27, 28, or 29, or the nucleotide sequence of the cDNA insert of a EpFAIL clone deposited with the ATCC® as patent deposit Number PTA-2266, or of a naturally occurring mutant of SEQ ID NO:1, 2, 15, 16 ,17, 18, 19, 20 or 21. In another embodiment, the oligonucleotide comprises a region of nucleotide sequence that hybridizes under stringent conditions to at least 25, preferably at least 50, 75, 100, 125, 150, 175, 200, 225, 250, 275, 300, 325, 350, 375, 450, 500, 530, 550, 600, 700, 800, 900, 1000 or 1150 consecutive oligonucleotides of the sense or antisense sequence of SEQ ID NO:1, 2, 15, 16, 17, 18, 19, 20, 21, 22, 23, 24, 25, 26, 27, 28, or 29, or the nucleotide sequence of the cDNA insert of a EpFAIL clone deposited with the ATCC® as patent deposit Number PTA-2266, or a naturally occurring mutant of SEQ ID NO:1, 2, 15, 16, 17, 18, 19, 20, or 21.

Probes based on the sequence of a nucleic acid molecule of the invention can be used to detect transcripts or genomic sequences encoding the same protein molecule encoded by a selected nucleic acid molecule. The probe comprises a label group attached thereto either directly or indirectly, e.g., a radioisotope, a fluorescent compound, an enzyme, or an enzyme co-factor. Such probes can be used as part of a diagnostic test kit for identifying cells or tissues which express or mis-express the protein, such as by measuring levels of a nucleic acid molecule encoding the protein in a sample of cells from a subject, e.g., detecting mRNA levels or determining whether a gene encoding the protein has been mutated or deleted.

A nucleic acid fragment encoding a biologically active portion of a polypeptide of the invention can be prepared by isolating a portion of any of SEQ ID NO:1, 2, 15, 16, 17, 18, 19, 20, 21, 22, 23, 24, 25, 26, 27, 28, or 29 expressing the encoded portion of the polypeptide protein (e.g., by recombinant expression in vitro) and assessing the activity of the encoded portion of the polypeptide.

The invention further encompasses nucleic acid molecules that differ from the nucleotide sequence of SEQ ID NO:1, 2, 15, 16, 17, 18, 19, 20, 21, 22, 23, 24, 25, 26, 27, 28, or 29 due to degeneracy of the genetic code and thus encode the same protein as that encoded by the nucleotide sequence of SEQ ID NO:1, 2, 15, 16, 17, 18, 19, 20, 21, 22, 23, 24, 25, 26, 27, 28, or 29.

In addition to the nucleotide sequences of SEQ ID NO:1, 2, 15, 16, 17, 18, 19, 20, 21, 22, 23, 24, 25, 26, 27, 28, or 29 it will be appreciated by those skilled in the art that DNA sequence polymorphisms that lead to changes in the amino acid sequence may exist within a population (e.g., the human population). Such genetic polymorphisms may exist among individuals within a population due to natural allelic variation. An allele is one of a group of genes which occur alternatively at a given genetic locus. As used herein, the terms "gene" and "recombinant gene" refer to nucleic acid molecules comprising an open reading frame, e.g., a contiguous open reading frame, encoding a polypeptide of the invention.

As used herein, the phrase "allele" or "allelic variant" refer to a nucleotide sequence which occurs at a given chromosomal locus, to a nucleic acid molecule that encodes a polypeptide encoded by the nucleotide sequence which occurs at the given chromosomal locus (e.g., a cDNA molecule), or to a polypeptide encoded by the nucleotide sequence. Allelic variations can typically result in about 1–5% variance in the nucleotide sequence of a given gene. Alternative alleles can be identified by sequencing the gene of interest in a number of different individuals. This can be readily carried out by using hybridization probes to identify the same genetic locus in a variety of individuals, and to characterize the polymorphisms present at the genetic locus across the individuals. In one embodiment, polymorphisms that are associated with a particular disease and/or disorder are used as markers to diagnose said disease or disorder. In a preferred embodiment, polymorphisms are used as a marker to diagnose abnormal immune function (e.g., immune diseases such as inflammatory bowel disease (e.g., Crohn's disease and ulcerative colitis), chronic obstructive pulmonary disease, autoimmune diseases (e.g., multiple sclerosis), and inflammatory disorders (e.g., rheumatoid arthritis and asthma)).

Moreover, nucleic acid molecules encoding proteins of the invention from other species (homologs), which have a nucleotide sequence which differs from that of the human protein described herein are intended to be within the scope of the invention. Nucleic acid molecules corresponding to natural allelic variants and homologs of a cDNA of the invention can be isolated based on their identity to the human nucleic acid molecule disclosed herein using the human cDNAs, or a portion thereof, as a hybridization probe according to standard hybridization techniques under stringent hybridization conditions.

Accordingly, in another embodiment, an isolated nucleic acid molecule of the invention is at least 25, preferably at least 50, at least 75, at least 100, at least 125, at least 150, at least 175, at least 200, at least 225, at least 250, at least 275, at least 300, at least 325, at least 350, at least 375, at least 400, at least 425, at least 450, at least 500, at least 600, at least 700, at least 800, at least 900, at least 1000, at least 1100, at least 1200, at least 1300, at least 1400, at least 1500, at least 1600, at least 1700, at least 1800 contiguous nucleotides in length and hybridizes under stringent conditions to the nucleic acid molecule comprising the nucleotide sequence, preferably the coding sequence, of SEQ ID NO:1, or a complement thereof.

Accordingly, in another embodiment, an isolated nucleic acid molecule of the invention is at least 25, preferably at least 50, at least 75, at least 100, at least 125, at least 150, at least 175, at least 200, at least 225, at least 250, at least 275, at least 300, at least 325, at least 350 or more contiguous nucleotides in length and hybridizes under stringent conditions to the nucleic acid molecule comprising the nucleotide sequence of SEQ ID NO:2, or a complement thereof.

Accordingly, in another embodiment, an isolated nucleic acid molecule of the invention is at least 25, preferably at least 50, at least 75, at least 100, at least 125, at least 150, at least 175, at least 200, at least 225, or at least 250 contiguous nucleotides in length and hybridizes under stringent conditions to the nucleic acid molecule comprising the nucleotide sequence of SEQ ID NO:6, or a complement thereof.

Accordingly, in another embodiment, an isolated nucleic acid molecule of the invention is at least 15 contiguous nucleotides in length and hybridizes under stringent conditions to the nucleic acid molecule comprising the nucleotide sequence of SEQ ID NO:7, or a complement thereof.

Accordingly, in another embodiment, an isolated nucleic acid molecule of the invention is at least 15, preferably at least 25, or at least 35 contiguous nucleotides in length and hybridizes under stringent conditions to the nucleic acid molecule comprising the nucleotide sequence of SEQ ID NO:6, or a complement thereof.

Accordingly, in another embodiment, an isolated nucleic acid molecule of the invention is at least 25, preferably at least 50 contiguous nucleotides in length and hybridizes under stringent conditions to the nucleic acid molecule comprising the nucleotide sequence of SEQ ID NO:9, 10 or 11, or a complement thereof.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. In one, non-limiting example stringent hybridization conditions are hybridization at 6×Sodium chloride/sodium citrate (SSC) at about 45° C., followed by one or more washes in 0.1×SSC, 0.2% SDS at about 68° C. A preferred, non-limiting example stringent hybridization conditions are hybridization in 6×SSC at about 45° C., followed by one or more washes in 0.2 ×SSC, 0.1% SDS at 50–65° C. (i.e., one or more washes at 50° C., 55° C., 60° C. or 65° C.). It is understood that the nucleic acids of the invention do not include nucleic acid molecules that hybridize under these conditions solely to a nucleotide sequence consisting of only A or T nucleotides.

Preferably, an isolated nucleic acid molecule of the invention that hybridizes under stringent conditions to the sequence of SEQ ID NO:1, 2, 15, 16, 17, 18, 19, 20, 21, 22, 23, 24, 25, 26, 27, 28 or 29, or a complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein), or to a cDNA molecule corresponding to (e.g., amplified or reverse-transcribed from) such an RNA or DNA molecule.

In addition to naturally-occurring variants of a nucleic acid molecule of the invention sequence that may exist in the population, the skilled artisan will further appreciate that changes can be introduced by mutation thereby leading to changes in the amino acid sequence of the encoded protein and production of a variant protein, without altering the biological activity of the protein. Said variants can function as either agonists (mimetics) or antagonists, as described below in the discussion of the polypeptides of the invention.

An isolated nucleic acid molecule encoding a variant protein can be created by introducing one or more nucleotide substitutions, additions or deletions into the nucleotide sequence of SEQ ID NO:1, 2, 15, 16, 17, 18, 19, 20, 21, 22, 23, 24, 25, 26, 27, 28 or 29 such that one or more amino acid substitutions, additions or deletions are introduced into the encoded protein. Mutations can be introduced by standard techniques, such as site-directed mutagenesis and PCR-mediated mutagenesis. SEQ ID NOS:22, 23, 24, 25, 26, 27, 28, and 29 are examples of nucleotide sequences encoding variant proteins of SEQ ID NO:3.

Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain or antagonize activity. Following mutagenesis, the encoded protein can be expressed recombinantly and the activity of the protein can be determined.

Specific examples of conservative amino acid alterations from the original amino acid sequence of SEQ ID NO:3 are shown in SEQ ID NO:30, 31, 32, and 33. Alternatively, amino acid residues that are conserved among the homologs of various species (e.g., mouse and human) may be essential for activity and thus would not be likely targets for alteration.

Nucleotide substitutions leading to amino acid substitutions at "non-essential" amino acid residues can be introduced. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species can be non-essential for activity and thus would be likely targets for alteration. Discussed below are additional methods by which to routinely identify non-essential amino acid residues.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:3, yet retain biological activity. In one embodiment, the isolated nucleic acid molecule includes a nucleotide sequence encoding a protein that includes an amino acid sequence that is at least about 30%, 35%, 40%, 45%, 50%, 55%, 60%, 65%, 75%, 85%, 95%, or 98% identical to the amino acid sequence of SEQ ID NO:3.

In a preferred embodiment, a polypeptide whose amino acid sequence has been modified can be assayed to determine whether it represents a variant of a polypeptide of the invention that retains a biological activity of a FAIL polypeptide by, for example, assaying for one or more of the following: (1) the ability to form or modulate protein-protein interactions and/or protein-ligand interactions with proteins in a signaling pathway of a polypeptide of the invention; (2) the ability to bind to and/or activate an intracellular target of a polypeptide of the invention (e.g., the ability to phosphorylate Syk, Lyn, Lck, phosphatidylinostiol 3-kinase, PLC-γ1, Zap-70 and/or PKC); (3) the ability to bind to an antibody or fragment thereof (e.g., the Fc portion of the antibody); (4) the ability to modulate endocyctosis and/or phagocytosis; and (5) the ability to modulate intercellular signaling.

In addition to the above functional assays, a polypeptide whose amino acid sequence has been modified can be assayed to determine whether it represents a variant of a polypeptide of the invention that retains a biological activity of a FAIL polypeptide by, for example, assaying whether it exhibits an antigenicity or immunogenicity of a polypeptide of the invention. For example, antibodies raised against the modified polypeptide can be tested for an ability to compete with antibodies directed against a polypeptide of the invention for binding to the polypeptide of the invention. Variant polypeptides are ones that can be used to generate antibodies that can compete for such binding.

In a specific embodiment, a nucleic acid sequence of the invention, e.g., the nucleotide sequence of SEQ ID NO:1, 2, 21, 22, 23, 24, 25, 26, 27, 28 or 29, or the nucleotide sequence of the cDNA insert of an EpFAIL clone deposited with the ATCC® as patent deposit number PTA-2266, encodes an Fc receptor (FcR) or FcR subunit which is capable of binding to an antibody (e.g., an IgG, IgM, IgE or IgA antibody) or fragment thereof (e.g., the Fc portion of an antibody). In a preferred embodiment, a nucleic acid sequence of the invention, e.g., the nucleotide sequence of SEQ ID NO:1, 2, 21, 22, 23, 24, 25, 26, 27 or 28, or the nucleotide sequence of the cDNA insert of an EpFAIL clone deposited with the ATCC® as patent deposit number PTA-2266, encodes an FcR or FcR subunit which is capable of binding to IgM antibody or a fragment thereof (e.g., the Fc portion of an IgM antibody). In another preferred embodiment, a nucleic acid sequence of the invention, e.g., the nucleotide sequence of SEQ ID NO:1, 2, 21, 22, 23, 24, 25, 26, 27 or 28, or the nucleotide sequence of the cDNA insert of an EpFAIL clone deposited with the ATCC® as patent deposit number PTA-2266, encodes FcµR which expressed on T cells and is capable of binding to IgM or a fragment thereof (e.g., the Fc portion of an IgM antibody). In accordance with these embodiments, techniques known to those of ordinary skill in the art for assaying the activity of FcRs can be utilized to assay the functional activity of the FAIL polypeptides encoded by the nucleic acid sequences of the invention, e.g., for assaying activity for a part of a procedure for identifying modulators of such FAIL polypeptides.

The invention also provides nucleic acid molecules that encode chimeric or fusion proteins. As used herein, a "chimeric protein" or "fusion protein" comprises all or part (preferably biologically active) of a polypeptide of the invention operably linked (e.g., joined via a peptide bond) to a heterologous polypeptide (i.e., a polypeptide other than the same polypeptide of the invention). The term "operably linked" is intended to indicate that the nucleic acid molecule encoding the polypeptide portion of the invention and the nucleic acid molecule encoding the heterologous polypeptide portion are fused in-frame to each other. The heterologous polypeptide can be fused to the N-terminus or C-terminus of the polypeptide of the invention.

The present invention encompasses nucleic acid molecules of the invention that are antisense molecules, i.e., molecules which are complementary to a sense nucleic acid encoding a polypeptide of the invention, e.g., complementary to the coding strand of a double-stranded cDNA molecule or complementary to an mRNA sequence. Accordingly, an antisense nucleic acid is one that can form a stable duplex with a sense nucleic acid, or, in the case of an antisense nucleic acid molecule that binds to DNA duplexes, through specific interactions in the major groove of the double helix. The antisense nucleic acid can be complementary to or bind to an entire coding strand, or to only a portion thereof, e.g., all or part of the protein coding open reading frame region. An antisense nucleic acid molecule can also be antisense to or bind to all or part of a non-coding region of the coding strand of a nucleotide sequence encoding a polypeptide of the invention, e.g., the non-coding region of a cDNA molecule. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-lodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention can be administered to a subject or generated in situ such that they hybridize with or bind to cellular mRNA and/or genomic DNA encoding a selected polypeptide of the invention to thereby inhibit expression, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al., 1987, *Nucleic Acids Res.* 15:6625–6641). The antisense nucleic acid molecule can also comprise a 2'-o-methylribonucleotide (Inoue et al., 1987, *Nucleic Acids Res.* 15:6131–6148) or a chimeric RNA-DNA analogue (Inoue et al., 1987, *FEBS Lett.* 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach, 1988, *Nature* 334:585–591)) can be used to catalytically cleave mRNA transcripts to thereby inhibit translation of the protein encoded by the mRNA. A ribozyme having specificity for a nucleic acid molecule encoding a polypeptide of the invention can be designed based upon the nucleotide sequence of a cDNA disclosed herein. For example, a derivative of a *Tetrahymena* L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of the invention can be used to select a catalytic RNA having a specific ribonuclease activity from a pool of RNA molecules. See, e.g., Bartel and Szostak, 1993, *Science* 261: 1411–1418.

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene, 1991, *Anticancer Drug Des.* 6(6):569–84; Helene, 1992, *Ann. N.Y. Acad. Sci.* 660:27–36; and Maher, 1992, *Bioassays* 14(12):807–15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, *Bioorganic & Medicinal Chemistry* 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., 1996, supra; and Perry-O'Keefe et al., 1996, *Proc. Natl. Acad. Sci. USA* 93: 14670–675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping, or as artificial restriction enzymes when used in combination with other enzymes, e.g., S I nucleases (Hyrup, 1996, supra; or as probes or primers for DNA sequence and hybridization (Hyrup, 1996, supra; and Perry-O'Keefe et al., 1996, *Proc. Natl. Acad. Sci.* USA 93: 14670–675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn et al., 1996, *Nucleic Acids Res.* 24(17):3357–63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973–88). PNA monomers are then coupled in a stepwise manner to produce a chimeric molecule with a 5' PNA segment and a 3' DNA segment (Finn et al., 1996, *Nucleic Acids Res.* 24(17):3357–63). Alternatively, chimeric molecules can be synthesized with a 5' DNA segment and a 3' PNA segment (Peterser et al., 1975, *Bioorganic Med. Chem. Lett.* 5:1119–11124).

In other embodiments, the oligonucleotide may include other appended groups such as peptides (e.g., for targeting host cell receptors in vivo ), or agents facilitating transport across the cell membrane (see, e.g., Letsinger et al., 1989, *Proc. Natl. Acad. Sci. USA* 86:6553–6556; Lemaitre et al., 1987, *Proc. Natl. Acad. Sci. USA* 84:648–652; PCT Publication No. WO 88/09810) or the blood-brain barrier,(see, e.g., PCT Publication No. WO 89/10134). In addition, oligonucleotides can be modified with hybridization-triggered cleavage agents (see, e.g., Krol et al., 1988, *Bio/Techniques* 6:958–976) or intercalating agents (see, e.g., Zon, 1988, *Pharm. Res.* 5:539–549). To this end, the oligonucleotide may be conjugated to another molecule, e.g., a peptide, hybridization triggered cross-linking agent, transport agent, hybridization-triggered cleavage agent, etc.

Isolated Proteins and Antibodies

One aspect of the invention pertains to isolated polypeptides of the invention. Such polypeptides can be produced by a variety of means. For example, the polypeptides of the invention can be isolated from natural sources, chemically synthesized, or recombinantly produced. In one embodiment, therefore, a native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques.

An "isolated" or "purified" polypeptide is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Preferred polypeptides have the amino acid sequence of SEQ ID NO:3, 4, 5, 6, 7, 8, 9, 10 ,11, 30, 31, 32, 33, or 34. Other useful, preferred polypeptides of the invention are ones that are substantially identical (e.g., at least about 45%, preferably 55%, 65%, 75%, 85%, 95%, 98%, or 99%) to any of such polypeptides of the invention and retain a functional and/or structural activity of a polypeptide of a corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (% identity=# of identical positions/total # of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389–3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used (accessible at the website maintained by National Center for Biotechnology Information, Bethesda, Md., USA (ncbi.nlm.nih.gov)).

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) *Comput. Appl. Biosci.,* 10:3–5; and FASTA described in Pearson and Lipman (1988) *Proc. Natl. Acad. Sci.* 85:2444–8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. For a further description of FASTA parameters, see the "fasta" or "man fasta" website documents on biological software (e.g. accessed in the Index of docs/man/man/ or at the scientific research section) maintained by the Institut Pasteur, Paris, France, the contents of which are incorporated herein by reference.

The percent identity between two sequences can be determined using techniques similar to those described above, with or without allowing gaps. In calculating percent identity, typically exact matches are counted.

The invention also provides chimeric or fusion proteins. As used herein, a "chimeric protein"0 or "fusion protein" comprises all or part (preferably biologically active) of a polypeptide of the invention operably linked (e.g., joined via a peptide bond) to a heterologous polypeptide (i.e., a polypeptide other than the same polypeptide of the invention). The heterologous polypeptide can be fused to the N-terminus or C-terminus of the polypeptide of the invention.

One useful fusion protein is a GST fusion protein in which the polypeptide of the invention is fused to the C-terminus of GST sequences. Such fusion proteins can facilitate the purification of a recombinant polypeptide of the invention.

In another embodiment, the fusion protein contains a heterologous signal sequence at its N-terminus. For example, the native signal sequence of a polypeptide of the invention can be removed and replaced with a signal sequence from another protein. For example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide of the invention is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction may be useful therapeutically, both for treating proliferative and differentiative disorders and for modulating (e.g., promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands.

Chimeric and fusion proteins of the invention can be produced by standard recombinant DNA techniques. For example, a nucleic acid molecule encoding a fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence of a polypeptide of the invention (e.g., SEQ ID NO:4) can be used to facilitate secretion and isolation of the secreted protein or other proteins of interest. Signal sequences are typically characterized by a core of hydrophobic amino acids at the N-terminus of a protein which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to the signal sequence itself and to the polypeptides in the absence of the signal sequence (i.e., the cleavage products). In one embodiment, a nucleic acid sequence encoding a signal sequence of the invention can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

In another embodiment, the signal sequences of the present invention can be used to identify regulatory sequences, e.g., promoters, enhancers, and repressors. Since signal sequences are the most amino-terminal sequences of a peptide, it is expected that the nucleic acids which flank the signal sequence on its amino-terminal side will be regulatory sequences which affect transcription. Thus, a nucleotide sequence which encodes all or a portion of a signal sequence can be used as a probe to identify and isolate signal sequences and their flanking regions, and these flanking regions can be studied to identify regulatory elements therein.

The present invention also pertains to variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a polypeptide of the invention which function as either agonists (mimetics) or as antagonists can be identified, for example, by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; and Ike et al., 1983, *Nucleic Acid Res.* 11:477).

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci.* USA 89:7811–7815; and Delgrave et al., 1993, *Protein Engineering* 6(3):327–33 1).

The polypeptides of the invention can be used in protein arrays to: (1) screen for proteins that interact with a polypeptide of the invention; (2) identify substrates of a polypeptide of the invention; and (3) identify small molecules that interact with a polypeptide of the invention. Methods of constructing protein arrays are known in the art (see, e.g., Fodor et al., 1996, "Photolabile nucleoside and peptide protecting groups", U.S. Pat. No. 5,489,678; Barret et al., 1993, "Spatially-addressable immobilization of anti-ligands on surfaces", U.S. Pat. No. 5,252,743; Blawas and Reichert, 1998, "Protein patterning", Biomaterials 19:595–609; Blawas et al., 1996, "Patterning antibodies for multiple analyte sensor via photodeprotection chemistry", San Jose: SPIE; Delamarche et al., 1996, "Immobilization of antibodies on a photoactive self-assembled monolayer on gold", Langmuir 12: 1997–2006; Firestone et al., 1996, "Film architecture in biomolecular assemblies, Effect of linker on the orientation of genetically engineered surface-bound proteins", J. Amer. Chem. Soc. 18: 9033–9041; Mooney et al., 1996, Patterning of functional antibodies and other proteins by photolithography of silane monolayers, Proc. Natl. Acad. Sci. 93: 12287–12291; Pirrung et al., 1996, "A general method for the spatially defined immobilization of biomolecules on glass surfaces using 'caged' biotin", Bioconjugate Chem. 7: 317–321; Gao et al., 1995, "Immunosensing with photoimmobilized immunoreagents on planar optical wave guides", Biosensors Bioelectron 10: 317–328; Schena et al., 1995, "Quantitative monitoring of gene expression patterns with a complementary DNA microarray", Science 270: 467–470; Lom et al., 1993, "A versatile technique for patterning biomolecules onto glass coverslips", J. Neurosci. Methods 385–397; Pope et al., 1993, "New applications of silane coupling agents for covalently binding antibodies to glass and cellulose solid phase surfaces", Bioconjugate Chem. 4: 116–171; Schramm et al., 1992, "Antibody-antigen complex formation with immobilized immunoglobulins", Anal. Biochem. 205: 47–56; Gombotz et al., 1991, Protein adsorption to poly(ethylene oxide) surfaces, J. Biomed. Mater. Res. 25: 1547–1562; Alarie et al., 1990, "Evaluation of antibody immobilization techniques for fiber optic-based fluoroimmunosensing", Analy. Chim. Acta 229: 169–176; Owaku et al., 1993, Optical immunosensing for IgG, Sensors Actuators B, 13–14: 723–724; Bhatia et al., 1989, "Use of thiol-terminal silanes and heterobifunctional cross linkers for immobilization of antibodies on silica surfaces", Analy. Biochem. 178: 408–413; Lin et al., 1988, "Characterization of immobilized antibodies on silica surfaces", IEEE Trans. Biomed. Engng., 35(6): 466–471; and MacBeath et al., 2000, "Printing Proteins as Microarrays for High-Throughput Function Determination", Science 289: 1760–762).

The polypeptides of the invention can exhibit post-translational modifications, including, but not limited to glycosylations, (e.g., N-linked or O-linked glycosylations), myristylations, palmitylations, acetylations and phosphorylations (e.g., serine/threonine or tyrosine). In one embodiment, the FAIL polypeptides of the invention exhibit reduced levels of O-linked glycosylation and/or N-linked glycosylation relative to endogenously expressed FAIL polypeptides. In another embodiment, the FAIL polypeptides of the invention do not exhibit O-linked glycosylation or N-linked glycosylation. Further, post-translational modifications of FAIL polypeptides such as glycosylation can be prevented by treating cells, e.g., with tunicamycin, or by expressing FAIL nucleic acid molecules in host cells lacking lacking the capacity to post-translational modify FAIL polypeptides.

An isolated polypeptide of the invention can be used as an antigen or immunogen to generate antibodies using standard techniques for polyclonal and monoclonal antibody preparation. The full-length polypeptide or protein, or antigenic peptide fragments can be used for use as immunogens. In one embodiment, an isolated polypeptide or fragment thereof which lacks N- and/or O-linked glycosylation is used as an immunogen to generate antibodies using standard techniques known to those of skill in the art. The antigenic peptide of a protein of the invention comprises at least 8 (preferably at least 10, at least 15, at least 20, or at least 30) contiguous amino acid residues of the amino acid sequence of SEQ ID NO:3, 4, 5, 6, 7, 8, 9, 10, 11, 30, 31, 32, 33 or 34, and encompasses an epitope of the protein such that an antibody raised against the peptide forms a specific immune complex with the protein.

In one embodiment, a polypeptide used as an antigen or immunogen comprises an amino acid sequence of SEQ ID NO:3, 4, 5, 6, 7, 8, 9, 10, 11, 30, 31, 32, 33 or 34, or the amino acid sequence encoded by the cDNA insert of EpFAIL deposited with ATCC® as patent deposit Number PTA-2266. In another embodiment, a polypeptide used as an antigen or immunogen comprises a fragment of at least 8, preferably at least 10, at least 15, at least 25, at least 30, at least 50, at least 75, at least 100 or more contiguous amino acid residues of the amino acid sequence of SEQ ID NO:3, 4, 5, 6, 7, 8, 9, 10, 11, 30, 31, 32, 33 or 34. In another embodiment, a polypeptide used as an antigen or immunogen comprises an amino acid sequence which is at least 50%, preferably at least 65%, at least 75%, at least 85%, at least 95% or at least 99% identical to the amino acid sequence of SEQ ID NO:3, 4, 5, 6, 7, 8, 9, 10, 11, 30, 31, 32, 33 or 34, wherein the percent identity is determined using a sequence alignment program such as the ALIGN program of the GCG software package with a PAM120 weight residue table, a gap length penalty of 12, and a gap penalty of 4. In yet another embodiment, a polypeptide used as an antigen or immunogen comprises an amino acid sequence which is encoded by a nucleic acid molecule which hybridizes to the nucleic acid molecule consisting of SEQ ID NO:1, 2, 14, 15, 16, 17, 18, 19, 20, 21, 22, 23, 24, 25, 26, 27, 28, or 29 under conditions of hybridization of 6×SSC at 45° C. and washing in 0.2×SSC, 0.1% SDS at 50° C., 55° C., 60° C. or 65° C., or 6×SSC at 45° C. and washing in 0.1×SSC, 0.2% SDS at 68° C.

The term "epitopes" as used herein refers to portions of a FAIL polypeptide having an antigenic or immunogenic activity in an animal, preferably a mammal, and most preferably a human. An epitope having immunogenic activity is a fragment of a FAIL polypeptide that elicits an antibody response in an animal. An epitope having antigenic activity is a fragment of a FAIL polypeptide to which an antibody immunospecifically binds in vivo or in vitro as determined by any method well known to those of skill in the art, for example, by the immunoassays described herein. Epitopes encompassed by the antigenic peptide are regions that are located on the surface of the protein, e.g., hydrophilic regions. Alternatively, epitopes encompassed by the antigenic peptides are regions that are located within the proteins, and/or epitopes exposed in denatured or partially denatured forms of the polypeptides of the invention. FIG. 2 is a hydropathy plot of the protein of the invention. This plot or similar analyses can be used to identify hydrophilic regions. In addition, an epitope can encompass, in addition to a polypeptide or polypeptides of the invention, a post-translational modification (e.g., glycosylation, such as, for example, N- and/or O-linked glycosylation of the polypeptide or polypeptides).

An immunogen typically is used to prepare antibodies by immunizing a suitable subject (e.g., rabbit, goat, mouse or other mammal). An appropriate immunogenic preparation can contain, for example, recombinantly expressed or chemically synthesized polypeptide. The preparation can further include an adjuvant, such as Freund's complete or incomplete adjuvant, or similar immunostimulatory agent.

Accordingly, another aspect of the invention pertains to antibodies directed against a polypeptide of the invention. The term "antibody" as used herein refers to immunoglobulin molecules and immunologically active portions of immunoglobulin molecules, i.e., molecules that contain an antigen binding site which specifically binds an antigen, such as a polypeptide of the invention, e.g., an epitope of a polypeptide of the invention. Antibodies of the invention include, but are not limited to, monoclonal antibodies, polyclonal antibodies, multispecific antibodies, human antibodies, humanized antibodies, chimeric antibodies, single chain Fv (scFv), single chain antibodies, anti-idiotypic (anti-Id) antibodies, F(ab) fragments, F(ab')$_2$ fragments, and epitope-binding fragments of any of the above. A molecule which specifically or immunospecifically binds to a given polypeptide of the invention or fragment thereof is a molecule which binds the polypeptide, but does not substantially bind other molecules in a sample, e.g., a biological sample, which naturally contains the polypeptide.

The antibodies of the invention may be from any animal origin including birds and mammals (e.g., human, mouse, donkey, rabbit, sheep, guinea pigs, camel, horse or chicken). In one embodiment, the antibodies of the invention originate from non-human mammals such as mice, rats, sheep, and goat. In another embodiment, the antibodies of the invention are human or humanized antibodies. As used herein, "human" antibodies include antibodies having the amino acid sequence of a human immunoglobulin and include antibodies isolated from human immunoglobulin libraries. In a preferred embodiment, the antibodies of the invention are human or humanized monoclonal antibodies. The term "monoclonal antibodies", "monoclonal antibody" or "monoclonal antibody composition", as used herein, refers to a population of antibody molecules that contain only one species of an antigen binding site capable of immunoreacting with a particular epitope.

The antibodies of the present invention may be monospecific, bispecific, trispecific or of greater multispecificity. Multispecific antibodies may be specific for different epitopes of a FAIL polypeptide or may be specific for both a FAIL polypeptide as well as for a heterologous epitope, such as a heterologous polypeptide or solid support material. See, e.g., PCT publications WO 93/177 15; WO 92/08802; WO 91/00360; WO 92/05793; Tutt, et al., J. Immunol. 147:60–69(1991); U.S. Pat. Nos. 4,474,893; 4,714,681; 4,925,648; 5,573,920; 5,601,819; and Kostelny et al., J. Immunol. 148:1547–1553 (1992).

In a specific embodiment, an antibody of the invention has a dissociation constant or $K_d$ of less than $10^{-2}$ M, less than $5\times10^{-2}$ M, less than $10^{-3}$ M, less than $5\times10^{-3}$, less than $10^{-4}$ M, less than $5\times10^{-4}$ M, less than $10^{-5}$ M, less than $5\times10^{-5}$ M, less than $10^{-6}$ M, less than $5\times10^{-6}$ M, less than $10^{-7}$ M, less than $5\times10^{-7}$ M, less than $10^{-8}$ M, less than $5\times10^{-8}$ M, less than $10^{-9}$ M, less than $5\times10^{-9}$ M, less than $10^{-10}$ M, less than $5\times10^{-10}$ M, less than $10^{-11}$ M, less than $5\times10^{-11}$ M, less than $10^{-12}$ M, less than $5\times10^{-12}$ M, less than $10^{-13}$ M, less than $5\times10^{-13}$ M, less than $10^{-14}$ M, less than $5\times10^{-14}$ M, less than $10^{-15}$ M, or less than $5\times10^{-15}$ M.

Polyclonal antibodies can be prepared as described above by immunizing a suitable subject with a polypeptide of the invention as an immunogen. Preferred polyclonal antibody compositions are ones that have been selected for antibodies directed against a polypeptide or polypeptides of the invention. Particularly preferred polyclonal antibody preparations are ones that contain only antibodies directed against a polypeptide or polypeptides of the invention. Particularly preferred immunogen compositions are those that contain no other human proteins such as, for example, immunogen compositions made using a non-human host cell for recombinant expression of a polypeptide of the invention. In such a manner, the only human epitope or epitopes recognized by the resulting antibody compositions raised against this immunogen will be present as part of a polypeptide or polypeptides of the invention.

The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. Alternatively, antibodies specific for a protein or polypeptide of the invention can be selected for (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those on the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein, 1975, *Nature* 256:495–497, the human B cell hybridoma technique (Kozbor et al., 1983, *Immunol. Today* 4:72), the EBV-hybridoma technique (Cole et al. (1985), *Monoclonal Antibodies and Cancer Therapy*, Alan R. Liss, Inc., pp. 77–96) or trioma techniques. The technology for producing hybridomas is well known (see generally *Current Protocols in Immunology* (1994) Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP™ *Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., 1991, *Bio/Technology* 9:1370–1372; Hay et al., 1992, *Hum. Antibod. Hybridomas* 3:81–85; Huse et al., 1989, *Science* 246:1275–1281; and Griffiths et al., 1993, *EMBO J.* 12:725–734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., 1988, *Science* 240:1041–1043; Liu et al., 1987, *Proc. Natl. Acad. Sci. USA* 84:3439–3443; Liu et al., 1987, *J. Immunol.* 139:3521–3526; Sun et al., 1987, *Proc. Natl. Acad. Sci. USA* 84:214–218; Nishimura et al., 1987, *Canc. Res.* 47:999–1005; Wood et al., 1985, Nature 314:446–449; and Shaw et al., 1988, J. Natl. Cancer Inst. 80:1553–1559); Morrison, 1985, *Science* 229:1202–1207; Oi et al., 1986, *Bio/Techniques* 4:214; U.S. Pat. No. 5,225,539; Jones et al., 1986, *Nature* 321:552–525; Verhoeyan et al., 1988, *Science* 239:1534; and Beidler et al., 1988, *J. Immunol.* 141:4053–4060.

Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgM, IgA and IgE antibodies. For an overview of this technology for producing human antibodies, see Lonberg and Huszar (1995, *Int. Rev. Immunol.* 13:65–93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. In addition, companies such as Abgenix, Inc. (Fremont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) Bio/technology 12:899–903).

Antibody fragments which recognize specific FAIL epitopes may be generated by any technique known to those of skill in the art. For example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain.

Further, the antibodies of the present invention can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., pCANTAB6 or pComb3HSS). The vector is electroporated in E. coli and the E. coli is infected with helper phage. Phage used in these methods are typically filamentous phage including fd and M13 and the VH and VL domains are usually recombinantly fused to either the phage gene III or gene VIII. Phage expressing an antigen binding domain that binds to a FAIL antigen can be selected or identified with antigen, e.g., using labeled antigen or antigen bound or captured to a solid surface or bead. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280(1994); PCT application No. PCT/GB91/O1 134; PCT publications WO 90/02809; WO 91/10737; WO 92/01047; WO 92/18619; WO 93/1 1236; WO 95/15982; WO 95/20401; W097/13844; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')$_2$ fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240: 1041–1043 (1988) (said references incorporated by reference in their entireties).

To generate whole antibodies (i.e., IgG antibodies) or Fab fragments, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. Preferably, the vectors for expressing the VH or VL domains in eukaryotic cells comprise pcDNA3 vectors containing CMV or EF-1a promoters, a secretion signal, a cloning site for the variable domain, constant domains, and a selection marker such as neomycin or DHFR. Vectors for expressing VH or VL domains in E. Coli comprise promoters, the constant domain of human IgG (CH1 and CL), leader sequences (pelB, ompA or gIII), a cloning site for the variable domain, and a selection marker such as kanimycin. The VH and VL domains may also be cloned into one vector expressing the necessary constant regions. The heavy chain conversion vectors and light chain conversion vectors are then co-transfected into E. coli or eukaryotic cell lines to generate stable or transient cell lines that express full-length antibodies, e.g., IgG or Fab fragments using techniques known to those of skill in the art. Active Fab fragments produced by stable or transient transfected cell lines will be recovered by Protein A chromatography. IgG antibody produced by stable or transient transfected cell lines will purified using Protein A chromatography. IgG produced by this method may be subjected to enzymatic digestion (e.g., papain) to release Fab or (Fab')2 fragments. The digested Fc fragment would be captured using Protein G affinity chromatography and the Fab or (Fab)$_2$ will be collected in the flow-through. The specificity and activity of antibodies produced can be analyzed in using assays described herein such as immunoassays.

The present invention also provides for antibodies that have a half-life in an animal, preferably a mammal and most preferably a human, of greater than 10 days, preferably greater than 15 days, greater than 25 days, greater than 30 days, greater than 35 days, greater than 40 days, greater than 45 days, greater than 2 months, greater than 3 months, greater than 4 months, or greater than 5 months. To prolong the serum circulation of antibodies (e.g., monoclonal antibodies, single chain antibodies and Fab fragments) in vivo, for example, inert polymer molecules such as high molecular weight polyethyleneglycol (PEG) can be attached to the antibodies with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. Degree of conjugation will be closely monitored by SDS-PAGE and mass spectrometry to ensure proper conjugation of PEG molecules to the antibodies. Unreacted PEG will be separated from antibody-PEG conjugates by size-exclusion or by ion-exchange chromatography. PEG-derivatized antibodies can be tested for binding activity as well as for in vivo efficacy using methods known to those of skill in the art, for example, by immunoassays described herein. Further, antibodies having an increased half-life in vivo can be generated as described in PCT Publication No. WO 97/34631.

In one aspect, the invention provides substantially purified antibodies or fragments thereof, including human, non-human, chimeric, and humanized antibodies, which antibodies or fragments thereof specifically bind to a polypeptide comprising an amino acid sequence of any one of SEQ ID NO:3, 4, 5, 6, 7, 8, 9, 10, 11, 30, 31, 32, 33 or 34, or an amino acid sequence encoded by the cDNA insert of a EpFAIL clone deposited with the ATCC® as patent deposit Number PTA-2266. In a preferred embodiment, the invention provides substantially purified human or humanized monoclonal antibodies which specifically bind to a polypeptide comprising an amino acid sequence of any one, of SEQ ID NO:3, 4, 5, 6, 7, 8, 9, 10, 11, 30, 31, 32, 33 or 34, or an amino acid sequence encoded by the cDNA insert of a EpFAIL clone deposited with the ATCC® as patent deposit Number PTA-2266.

In another aspect, the invention provides substantially purified antibodies or fragments thereof, including human, non-human, chimeric and humanized antibodies, which antibodies or fragments thereof specifically bind to a polypeptide comprising a fragment of at least 8 contiguous amino acid residues, preferably at least 10 or at least 15 contiguous amino acid residues, of the amino acid sequence of any one of SEQ ID NOS:3, 4, 5, 6, 7, 8, 9, 10, 11, 30, 31, 32, 33 or 34, or an amino acid sequence encoded by the cDNA insert of a EpFAIL clone deposited with the ATCC® as patent deposit Number PTA-2266. In a preferred embodiment, the invention provides substantially purified human or humanized monoclonal antibodies which specifically bind to a polypeptide comprising a fragment of at least 8 contiguous amino acid residues, preferably at least 15 contiguous amino acid residues, of the amino acid sequence of any one of SEQ ID NO:3, 4, 5, 6, 7, 8, 9, 10, 11, 30, 31, 32, 33 or 34, or an amino acid sequence encoded by the cDNA insert of a EpFAIL clone deposited with the ATCC® as patent deposit Number PTA-2266.

In another aspect, the invention provides substantially purified antibodies or fragments thereof, including human, non-human, chimeric and humanized antibodies, which antibodies or fragments thereof specifically bind to a polypeptide comprising an amino acid sequence which is at least 65%, preferably at least 75%, at least 85%, at least 95%, or at least 98% identical to the amino acid sequence of any one of SEQ ID NO:3, 4, 5, 6, 7, 8, 9, 10, 11, 30, 31, 32, 33 or 34, wherein the percent identity is determined using a sequence alignment program such as the ALIGN program of the GCG software package with a PAM120 weight residue table, a gap length penalty of 12, and a gap penalty of 4. In a specific embodiment, the invention provides substantially purified human or humanized monoclonal antibodies which specifically bind to a polypeptide comprising an amino acid sequence which is at least 65%, preferably at least 75%, at least 85%, at least 95%, or at least 98% identical to the amino acid sequence of any one of SEQ ID NO:3, 4, 5, 6, 7, 8, 9, 10, 11, 30, 31, 32, 33 or 34, wherein the percent identity is determined using the ALIGN program of the GCG software package with a PAM120 weight residue table, a gap length penalty of 12, and a gap penalty of 4.

In another aspect, the invention provides substantially purified antibodies or fragments thereof, including human, non-human, chimeric and humanized antibodies, which antibodies or fragments thereof specifically bind to a polypeptide comprising and an amino acid sequence which is encoded by a nucleic acid molecule which hybridizes to the nucleic acid molecule consisting of any one of SEQ ID NO:1, 2, 15, 16, 17, 18, 19, 20, 21, 22, 23, 24, 25, 26, 27, 28, or 29, or the cDNA insert of a clone deposited as ATCC® as patent deposit Number PTA-2266, or a complement thereof, under conditions of hybridization of 6×SSC at 45 C and washing in 0.2×SSC, 0.1% SDS at 50° C., 55° C., 60° C. or 65° C., or 6×SSC 45° C. and washing in 0.1×SSC, 0.2% SDS at 68° C. In a specific embodiment, the invention provides substantially purified human or humanized monoclonal antibodies which specifically bind to a polypeptide comprising an amino acid sequence which is encoded by a nucleic acid molecule which hybridizes to the nucleic acid molecule consisting of any one of SEQ ID NO:1, 2, 15, 16, 17, 18, 19, 20, 21, 22, 23, 24, 25, 26, 27, 28, or 29, or the cDNA insert of a clone deposited as ATCC® as patent deposit Number PTA-2266, under conditions of hybridization of 6×SSC at 45 C and washing in 0.2×SSC, 0.1% SDS at 50° C., 55° C., 60° C. or 65° C., or 6×SSC at 45° C. and washing in 0.1×SSC, 0.2% SDS at 68° C.

In various embodiments, the substantially purified antibodies or fragments thereof of the invention are polyclonal, monoclonal, Fab fragments, single chain antibodies, or F(ab')2 fragments. The non-human antibodies or fragments thereof of the invention can be goat, mouse, sheep, horse, chicken, rabbit or rat antibodies or antibodies fragments. In a preferred embodiment, the antibodies of the invention are monoclonal antibodies that specifically bind to a polypeptide of the invention.

The substantially purified antibodies or fragments thereof specifically bind to a signal peptide, a secreted sequence, an extracellular domain, a transmembrane or a cytoplasmic domain cytoplasmic membrane of a polypeptide of the invention. In a particularly preferred embodiment, the substantially purified antibodies or fragments thereof of the invention specifically bind to a secreted sequence or an extracellular domain of the amino acid sequence of SEQ ID NO:3, 4, 5, 6, 7, 8, 9, 10, 11, 30, 31, 32, 33 or 34, or the amino acid sequence encoded by the cDNA insert of EpFAIL deposited with the ATCC® as patent deposit Number PTA-2266, or a complement thereof. In one embodiment, the extracellular domain to which the antibody or antibody fragment binds comprises at least 8 contiguous amino acid residues, preferably at least 10 or at least 15 contiguous amino acid residues, of amino acid residues 28 to 305 of SEQ ID NO:3 (SEQ ID NO:6).

In one embodiment, antibodies of the invention are ones that immunospecifically bind to a native FAIL polypeptide or fragment thereof (e.g., a glycosylated FAIL polypeptide or fragment thereof). In another embodiment, antibodies of the invention are ones that immunospecifically bind to a FAIL polypeptide comprising the native primary amino acid sequence, or fragment thereof, lacking post-translational modifications such as glycosylation.

The antibodies of the invention may be assayed for immunospecific binding to a FAIL polypeptide or fragments thereof and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

In a preferred embodiment, BIAcore kinetic analysis is used to determine the binding on and off rates of antibodies to a FAIL polypeptide. BIAcore kinetic analysis is a well known technique that comprises, in this instance, analyzing the binding and dissociation of a FAIL polypeptide from chips with immobilized antibodies on their surface.

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Further, an antibody (or fragment thereof) can be conjugated to a therapeutic moiety such as a cytotoxin, a therapeutic agent or a radioactive metal ion. A cytotoxin or cytotoxic agent includes any agent that is detrimental to cell viability or function. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Although the conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, interferon-α, interferon-β, nerve growth factor, platelet derived growth factor, tissue plasminogen activator; or, biological response modifiers such as, for example, lymphokines, interleukin-1 ("IL-1"), interleukin-2 ("IL-2"), interleukin-4 ("IL-4"), interleukin-5 ("IL-5"), interleukin-6 ("IL-6"), interleukin-10 ("IL-10"), interleukin-12 ("IL-12"), granulocyte macrophase colony stimulating factor ("GM-CSF"), granulocyte colony stimulating factor ("G-CSF"), or other growth factors.

Techniques for conjugating a therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982).

Alternatively, an antibody can be conjugated to a second antibody to form an antibody heteroconjugate as described by Segal in U.S. Pat. No. 4,676,980.

The invention also provides a kit containing an antibody of the invention conjugated to a detectable substance, and instructions for use. Still another aspect of the invention is a pharmaceutical composition comprising an antibody of the invention and a pharmaceutically acceptable carrier. In preferred embodiments, the pharmaceutical composition contains an antibody of the invention, a therapeutic moiety, and a pharmaceutically acceptable carrier.

Recombinant Expression Vectors and Host Cells

Another aspect of the invention pertains to vectors, preferably expression vectors, containing a nucleic acid encoding a polypeptide of the invention (or a fragment thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., *E. coli*) or eukaryotic cells (e.g., insect cells (using baculovirus expression vectors), yeast cells, or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, Gene 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS 174(DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., 1992, *Nucleic Acids Res*. 20:2111–2118). Such alteration of nucleic acid sequences of the invention can be carried out by standard DNA synthesis techniques.

In another embodiment, the expression vector is a yeast expression vector. Examples of vectors for expression in yeast *S. cerivisae* include pYepSec1 (Baldari et al., 1987, *EMBO J*. 6:229–234), pMFa (Kurjan and Herskowitz, 1982, *Cell* 30:933–943), pJRY88 (Schultz et al., 1987, *Gene* 54:113–123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf9 cells) include the pAc series (Smith et al., 1983, *Mol. Cell Biol*. 3:2156–2165) and the pVL series (Lucklow and Summers, 1989, *Virology* 170:31–39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J*. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev*. 1:268–277), lymphoid-specific promoters (Calame and Eaton, 1988, *Adv. Immunol*. 43:235–275), in particular, promoters of T cell receptors (Winoto and Baltimore, 1989, *EMBO J*. 8:729–733) and immunoglobulins (Banerji et al., 1983), Cell 33:729–740; Queen and Baltimore, 1983), Cell 33:741–748), neuron-specific promoters (e.g., the neurofilament promoter; Byrne and Ruddle, 1989, *Proc. Natl. Acad. Sci. USA* 86:5473–5477), pancreas-specific promoters (Edlund et al., 1985, *Science* 230:912–916), and mammary gland-specific promoters (e.g., milk whey promoter; U.S. Pat. No. 4,873, 316 and European Application Publication No. 264,166). Developmentally-regulated promoters are also encompassed, for example, the mouse hox promoters (Kessel and Gruss, 1990, *Science* 249:374–379) and the beta-fetoprotein promoter (Campes and Tilghman, 1989, *Genes Dev*. 3:537–546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (*Reviews—Trends in Genetics*, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells). Host cells intended to be part of the invention include ones that comprise a nucleic acid molecule of the invention that has been engineered to be present within the host cell (e.g., as part of a vector), and ones that comprise nucleic acid regulatory sequences that have been engineered to be present in the host cell such that a nucleic acid molecule of the invention is expressed within the host cell.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, whereas cells that have not die).

In another embodiment, the expression characteristics of endogenous FAIL genes within a cell, cell line, or microorganism may be modified by inserting a DNA regulatory element heterologous to the endogenous gene of interest into the genome of a cell, stable cell line, or cloned microorganism such that the inserted regulatory element is operatively linked with the endogenous FAIL genes and controls, modulates or activates. For example, endogenous FAIL genes which are normally "transcriptionally silent", i.e., FAIL genes which is normally not expressed, or are expressed only at very low levels in a cell line or microorganism, may be activated by inserting a regulatory element which is capable of promoting the expression of a normally expressed gene product in that cell line or microorganism. Alternatively, transcriptionally silent, endogenous FAIL genes may be activated by insertion of a promiscuous regulatory element that works across cell types.

A heterologous regulatory element may be inserted into a stable cell line or cloned microorganism, such that it is operatively linked with and activates expression of endogenous FAIL genes, using techniques, such as targeted homologous recombination, which are well known to those of skill in the art, and described, e.g., in Chappel, U.S. Pat. No. 5,272,071; and PCT publication No. WO 91/06667, published May 16, 1991.

A host cell of the invention, such as a prokaryotic or eukaryotic host cell in culture, can be used to produce a polypeptide of the invention. Accordingly, the invention further provides methods for producing a polypeptide of the invention using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a sequence encoding a polypeptide of the invention has been introduced. Such host cells can then be used to create non-human transgenic animals in which exogenous sequences encoding a polypeptide of the invention have been introduced into their genome. Further, such host cells can be used to create or homologous recombinant animals in which endogenous gene sequences encoding a polypeptide of the invention have been altered. Such animals are useful for studying the function and/or activity of the polypeptide and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid molecule encoding a polypeptide of the invention (or a homologue thereof) into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, 4,873,191, in Hogan, *Manipulating the Mouse Embryo*, (Cold Spring Harbor Laboratory Press, Cold Spring Harbor, N.Y., 1986) and in Wakayama et al., 1999, *Proc. Natl. Acad. Sci. USA*, 96:14984–14989. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a polypeptide of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and at the 3' ends) are included in the vector (see, e.g., Thomas and Capecchi, 1987, Cell 51:503 for a description of homologous recombination vectors). The vector is introduced into an embryonic stem cell line (e.g., by electroporation) and cells in which the introduced gene has homologously recombined with the endogenous gene are selected (see, e.g., Li et al., 1992, Cell 69:915). The selected cells are then injected into a blastocyst of an animal (e.g., a mouse) to form aggregation chimeras (see, e.g., Bradley in *Teratocarcinomas and Embryonic Stem Cells: A Practical Approach*, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, 1991, *Current Opinion in Bio/Technology* 2:823–829 and in PCT Publication Nos. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al., 1992, *Proc. Natl. Acad. Sci. USA* 89:6232–6236. Another example of a recombinase system is the FLP recombinase system of *Saccharomyces cerevisiae* (O'Gorman et al., 1991, *Science* 251: 1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al., 1997, *Nature* 385:810–813 and PCT Publication NOS. WO 97/07668 and WO 97/07669.

Pharmaceutical Compositions

The nucleic acid molecules, polypeptides, antibodies, and FAIL modulators (also referred to herein as "active compounds") of the invention can be incorporated into pharmaceutical compositions suitable for administration. Such compositions typically comprise the nucleic acid molecule, polypeptide, antibody, or modulator and a pharmaceutically acceptable carrier. As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

A pharmaceutical composition of the invention is formulated to be compatible with its intended route of administration. Examples of routes of administration include parenteral, e.g., intravenous, intradermal, subcutaneous, oral (e.g., inhalation), intranasal, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation (Mountain View, Calif.) and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

Preferably, administration of the FAIL modulator is at or near the site of the cells or tissue to be treated, e.g., administration is at or near the site of a disorder such as one of those described herein.

In certain embodiments, the FAIL modulator is administered or co-administered with at least one other desirable agent, e.g., at least one agent used to treat an immune disorder described herein.

In certain instances, it is preferred that administration of a FAIL modulator comprises an initial bolus followed by continuous infusion. For example, such instances will generally include those wherein the modulator exhibits appreciable reversibility in platelet binding, as, e.g., assayed via the techniques described herein.

The present invention encompasses agents which modulate expression or activity of FAIL. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. With rspect to small organic molecules, such compounds are generally ones that are orally active (that is, can be administered orally).

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Uses and Methods of the Invention

The nucleic acid molecules, proteins, protein homologs, antibodies and FAIL modulators described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic).

Further, the activity of polypeptides of the invention, as well as the effect of FAIL modulators on FAIL can routinely be ascertained via use of a number of different in vitro or cell-based systems well known to those of skill in the art. For example, the intracellular signaling molecules activated in response to the binding of FAIL to its ligand can be measured in vitro using standard assays known to those of skill in the art such as immunoprecipitation followed by Western blot analysis. The activity of polypeptides of the invention, including the therapeutic, e.g., clinical, efficacy of the polypeptides, as well as the effect, including the therapeutic, e.g., clinical, efficacy, of FAIL modulators can routinely be ascertained via use of a number of different animal models well known to those of skill in the art. Such methods of ascertaining the activity of polypeptides of the invention, as wells as screening assays for ascertaining the modulatory activity of test compounds are described below.

The isolated nucleic acid molecules of the invention can be used to express proteins (e.g., via a recombinant expression vector in a host cell in gene therapy applications), to detect mRNA (e.g., in a biological sample) or a genetic lesion, and to modulate activity of a polypeptide of the invention. In addition, the polypeptides of the invention can be used to screen drugs or compounds which modulate activity or expression of a polypeptide of the invention as well as to treat disorders characterized by insufficient or excessive production of a protein of the invention or production of a form of a protein of the invention which has decreased or aberrant activity compared to the wild type protein. In addition, the antibodies of the invention can be used to detect and isolate a protein of the invention, isolate any protein of interest when such protein is present as a fusion protein with a polypeptide of the invention, or to modulate activity of a protein of the invention.

This invention further pertains to novel agents (modulators) identified by the above-described screening assays and uses thereof for treatments as described herein.

Screening Assays

The invention provides a method (also referred to herein as a "screening assay") for identifying modulators, i.e., candidate or test compounds or agents (e.g., peptides, peptidomimetics, small molecules or other drugs) which bind to polypeptide of the invention or have a modulatory (e.g., stimulatory or inhibitory) effect on, for example, expression or activity of a polypeptide of the invention.

In one embodiment, the invention provides assays for screening candidate or test compounds which bind to or modulate the activity of the membrane-bound form of a polypeptide of the invention or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869) or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

Cell-Free Assays

In one embodiment, an assay of the present invention is a cell-free assay comprising contacting a polypeptide of the invention or biologically active portion thereof with a test compound and determining the ability of the test compound to bind to the polypeptide or biologically active portion thereof. Binding of the test compound to the polypeptide can be determined either directly or indirectly as described above. In a preferred embodiment, the assay includes contacting the polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or biologically active portion thereof as compared to the known compound.

In another embodiment, an assay is a cell-free assay comprising contacting a polypeptide of the invention or biologically active portion thereof with a test compound and determining the ability of the test compound to modulate (e.g., stimulate or inhibit) the activity of the polypeptide or biologically active portion thereof. Determining the ability of the test compound to modulate the activity of the polypeptide can be accomplished, for example, by determining the ability of the polypeptide to bind to a target molecule by one of the methods described above for determining direct binding. In an alternative embodiment, determining the ability of the test compound to modulate the activity of the polypeptide can be accomplished by determining the ability of the polypeptide of the invention to further modulate the target molecule. For example, the catalytic/enzymatic activity of the target molecule on an appropriate substrate can be determined as previously described.

In yet another embodiment, the cell-free assay comprises contacting a polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the polypeptide to preferentially bind to or modulate the activity of a target molecule.

The cell-free assays of the present invention are amenable to use of both a soluble form or the membrane-bound form of a polypeptide of the invention. In the case of cell-free assays comprising the membrane-bound form of the polypeptide, it may be desirable to utilize a solubilizing agent such that the membrane-bound form of the polypeptide is maintained in solution. Examples of such solubilizing agents include non-ionic detergents such as n-octylglucoside, n-dodecylglucoside, n-octylmaltoside, octanoyl-N-methylglucamide, decanoyl-N-methylglucamide, Triton X-100, Triton X-114, Thesit, Isotridecypoly(ethylene glycol ether) n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), and N-dodecyl=N,N-dimethyl-3-ammonio-1-propane sulfonate.

In more than one embodiment of the above assay methods of the present invention, it may be desirable to immobilize either the polypeptide of the invention or its target molecule to facilitate separation of complexed from uncomplexed forms of one or both of the proteins, as well as to accommodate automation of the assay. Binding of a test compound to the polypeptide, or interaction of the polypeptide with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase (GST) fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or A polypeptide of the invention, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the polypeptide of the invention or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the polypeptide of the invention or target molecules but which do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

This invention further pertains to novel agents identified by the above-described screening assays and uses thereof for treatments as described herein.

Cell-based Assays

In one embodiment, an assay is a cell-based assay in which a cell which expresses a membrane-bound form of a polypeptide of the invention, or a biologically active portion thereof, on the cell surface is contacted with a test compound, and the ability of the test compound to bind to the polypeptide determined. The cell, for example, can be a yeast cell or a cell of mammalian origin. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of a polypeptide of the invention, or a biologically active portion thereof, on the cell surface with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or a biologically active portion thereof as compared to the known compound.

In another embodiment, an assay is a cell-based assay comprising contacting a cell expressing a membrane-bound form of a polypeptide of the invention, or a biologically active portion thereof, on the cell surface with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide protein to bind to or interact with a target molecule.

Determining the ability of a polypeptide of the invention to bind to or interact with a target molecule can be accomplished by one of the methods described above for determining direct binding. As used herein, a "target molecule" is a molecule with which a selected polypeptide (e.g., a polypeptide of the invention) binds or interacts with in nature, for example, a molecule on the surface of a cell which expresses the selected protein, a molecule on the surface of a second cell, a molecule in the extracellular milieu, a molecule associated with the internal surface of a cell membrane or a cytoplasmic molecule. A target molecule can be a polypeptide of the invention or some other polypeptide or protein. For example, a target molecule can be a component of a signal transduction pathway which facilitates transduction of an extracellular signal (e.g., a signal generated by binding of a compound to a polypeptide of the invention) through the cell membrane and into the cell or a second intercellular protein which has catalytic activity or a protein which facilitates the association of downstream signaling molecules with a polypeptide of the invention. Determining the ability of a polypeptide of the invention to bind to or interact with a target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g., luciferase), or detecting a cellular response, for example, cellular differentiation, or cell proliferation.

In another embodiment, modulators of expression of a polypeptide of the invention are identified in a method in which a cell is contacted with a candidate compound and the expression of the selected mRNA or protein (i.e., the mRNA or protein corresponding to a polypeptide or nucleic acid of the invention) in the cell is determined. The level of expression of the selected mRNA or protein in the presence of the candidate compound is compared to the level of expression of the selected mRNA or protein in the absence of the candidate compound. The candidate compound can then be identified as a modulator of expression of the polypeptide of the invention based on this comparison. For example, when expression of the selected mRNA or protein is greater (statistically significantly greater) in the presence of the candidate compound than in its absence, the candidate compound is identified as a stimulator of the selected mRNA or protein expression. Alternatively, when expression of the selected mRNA or protein is less (statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a polypeptide of the invention can be used as "bait proteins" in a two-hybrid assay or three hybrid assay (see, e.g., U.S. Pat. No. 5,283, 317; Zervos et al. (1993) Cell 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with the polypeptide of the invention and modulate activity of the polypeptide of the invention. Such binding proteins are also likely to be involved in the propagation of signals by the polypeptide of the inventions as, for example, upstream or downstream elements of a signaling pathway involving the polypeptide of the invention.

This invention further pertains to novel agents identified by the above-described screening assays and uses thereof for treatments as described herein.

In particular, the detection and expression of FAIL can be readily detected, e.g., by quantifying FAIL protein and/or RNA. Many methods standard in the art can be thus employed, including, but not limited to, immunoassays to detect and/or visualize gene expression (e.g., Western blot, immunoprecipitation followed by sodium dodecyl sulfate polyacrylamide gel electrophoresis (SDS-PAGE), immunocytochemistry, etc.) and/or hybridization assays to detect gene expression by detecting and/or visualizing, respectively, mRNA encoding a gene (e.g., Northern assays, dot blots, in situ hybridization, etc.), etc. Both wild-type and mutant, including disease-associated mutant, genes encoding a FAIL can also be detected using standard techniques such as those described herein. Such detection and predictive medicine-related uses and methods are described below.

Animal Models

The activity of polypeptides of the invention, including the therapeutic, e.g., clinical, efficacy of the polypeptides, as well as the effect, including the therapeutic, e.g., clinical, efficacy, of FAIL modulators can routinely be ascertained via use of a number of different accepted animal models well known to those of skill in the art. Such methods of ascertaining the activity of polypeptides of the invention, as well as screening assays for ascertaining the modulatory activity of test compounds are described below.

A number of animal models for autoimmune disorder models can be utilized to assess the activity of FAIL. First, an experimental allergic encephalomyelitis (EAE) model can be utilized. EAE is an experimental autoimmune disease of the central nervous system (CNS) (Zamvil et al, 1990, Ann. Rev, Immunol. 8:579) and is a disease model for the human autoimmune condition, multiple sclerosis (MS). EAE is an example of a cell-mediated autoimmune disorder that is mediated via T cells. EAE is readily induced in mammalian species by immunizations of myelin basic protein (MBP) purified from the CNS or an encephalitogenic proteolipid (PLP). SJL/J mice are a susceptible strain of mice (H-2$^u$) and, upon induction of EAE, these mice develop an acute paralytic disease and an acute cellular infiltrate is identifiable within the CNS. EAE spontaneously develops in MBP$_{1-17}$ peptide-specific T cell receptor (TCR) transgenic mice (TgMBP$^+$) of a RAG-1-deficient background (Lafaille et al., 1994, Cell 78:399).

A collagen-induced arthritis (CIA) model can also be utilized CIA is an animal model for the human autoimmune disease rheumatoid arthritis (RA) (Trenthorn et al., 1977, J. Exp. Med., 146:857). This disease can be induced in many species by the administration of heterologous type II collagen (Courtenay et al., 1980, Nature 283:665; Cathcart et at, 1986, Lab. Invest., 54:26). With respect to animal models of arthritis see, in addition, e.g., Holmdahl, R., 1999, Curr. Biol. 15:R528–530.

Animal models for chronic obstructive pulmonary disease (COPD) can also be used to assess the activity of FAIL (for review of COPD animal models see, e.g., Shapiro, 2000, Am. J. Respir. Cell Mol. Biol. 22:4–7; and Shapiro, 2000, Chest 117:2223S–227S). COPD is a generic term for several clinical syndromes including, but not limit to, emphysema and chronic bronchitis. Emphysema can be induced in animals such as mice by the administration or overexpression of elasolytic enzymes including, but not limited to pancreatic elastase, neutrophil elastase, and proteinase 3. Emphysema can also be induced by the administration of a variety of chemicals and irritants including, but not limited to, lipopolysaccharides (LPS), cadmium chloride, nitrogen dioxide, inorganic dust, and ozone. Further, emphysema can be induced by overexpression of interferon-( (IFN-( ). Cigarette smoke-related COPD in mice can be induced by chronic exposure to cigarette smoke. Pulmonary fibrosis can be induced by the administration of bleomycin to mice. Further, mutant mouse strains, such as tight skin (Tsk$^{+/-}$), pallid (pa/pa), blotchy (Blo), mice transgenic for collagenase, and PDGF-A$^{-/-}$, that spontaneously develop enlarged airspaces can also be used.

Animal models for inflammatory bowel disease (IBD) can also be used to assess the activity of FAIL (for review see, e.g., Kim et al., 1992, Scand. J. Gastroentrol. 27:529–537; and Strober, 1985, Dig. Dis. Sci. 30(12 Suppl.):3S–10S. Crohn's disease and ulcerative colitis are two types of human IBDs. IBD can be induced in animals by oral administration of sulfated polysaccharides including, but not limited to, carrageenan, amylopectin sulfate, and dextran sulfate. IBD can also be induced by the administration of chemical irritants such as trinitrobenzenesulphonic acid (TNBS) and acetic acid.

Further, animal models such as the adoptive transfer model described, e.g., in L. Cohn et al., 1997, J. Exp. Med. 186:1737–1747) can be used to assess the activity of FAIL. In such an animal system, aeroallergen provocation of TH1 or TH2 recipient mice results in TH effector cell migration to the airways and is associated with an intense neutrophilic (TH1) and eosinophilic (TH2) lung mucosal inflammatory response. The animal model represents an accepted model for asthma.

Still further, animal models for type 1 diabetes, thyroid autoimmunity or systemic lupus erythematosus, including glomerulonephritis can be utilized to assess the activity of FAIL (see, e.g., Flanders et al., 1999, Autoimmunity 29:235–246; Krogh et al., 1999, Biochimie 81:511–515; and Foster, N.H., 1999, Semin. Nephrol. 19:12–24, respectively).

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome and, thus, locate gene regions associated with genetic disease; (ii) identify an individual from a minute biological sample (tissue typing); and (iii) aid in forensic identification of a biological sample. These applications are described in the subsections below.

Chromosome Mapping

Once the sequence (or a portion of the sequence) of a gene has been isolated, this sequence can be used to map the location of the gene on a chromosome. Accordingly, nucleic acid molecules described herein or fragments thereof, can be used to map the location of the corresponding genes on a chromosome. The mapping of the sequences to chromosomes is an important first step in correlating these sequences with genes associated with disease.

Briefly, genes can be mapped to chromosomes by preparing PCR primers (preferably 15–25 bp in length) from the sequence of a gene of the invention. Computer analysis of the sequence of a gene of the invention can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the gene sequences will yield an amplified fragment. For a review of this technique, see D'Eustachio et al., 1983, *Science* 220:919–924.

PCR mapping of somatic cell hybrids is a rapid procedure for assigning a particular sequence to a particular chromosome. Three or more sequences can be assigned per day using a single thermal cycler. Using the nucleic acid sequences of the invention to design oligonucleotide primers, sublocalization can be achieved with panels of fragments from specific chromosomes. Other mapping strategies which can similarly be used to map a gene to its chromosome include in situ hybridization (described in Fan et al. (1990) *Proc. Natl. Acad. Sci. USA* 87:6223–27), pre-screening with labeled flow-sorted chromosomes (CITE), and pre-selection by hybridization to chromosome specific cDNA libraries. Fluorescence in situ hybridization (FISH) of a DNA sequence to a metaphase chromosomal spread can further be used to provide a precise chromosomal location in one step. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al., 1987, *Nature* 325:783–787.

Moreover, differences in the DNA sequences between individuals affected and unaffected with a disease associated with a gene of the invention can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

A polypeptide and fragments and sequences thereof and antibodies specific thereto can be used to map the location of the gene encoding the polypeptide on a chromosome. This mapping can be carried out by specifically detecting the presence of the polypeptide in members of a panel of somatic cell hybrids between cells of a first species of animal from which the protein originates and cells from a second species of animal and then determining which somatic cell hybrid(s) expresses the polypeptide and noting the chromosome(s) from the first species of animal that it contains. For examples of this technique, see Pajunen et al. (1988) *Cytogenet. Cell Genet.* 47:37–41 and Van Keuren et al. (1986) *Hum. Genet.* 74:34–40. Alternatively, the presence of the polypeptide in the somatic cell hybrids can be determined by assaying an activity or property of the polypeptide, for example, enzymatic activity, as described in Bordelon-Riser et al., 1979, *Somatic Cell Genetics* 5:597–613 and Owerbach et al., 1978, *Proc. Natl. Acad. Sci. USA* 75:5640–5644.

Tissue Typing

The nucleic acid sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the nucleic acid sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The nucleic acid sequences of the invention uniquely represent portions of the human genome. Allelic variation occurs to some degree in the coding regions of these sequences, and to a greater degree in the noncoding regions. It is estimated that allelic variation between individual humans occurs with a frequency at about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:1 are used, a more appropriate number of primers for positive individual identification would be 500–2,000.

If a panel of reagents from the nucleic acid sequences described herein is used to generate a unique identification database for an individual, those same reagents can later be used to identify tissue from that individual. Using the unique identification database, positive identification of the individual, living or dead, can be made from extremely small tissue samples.

Use of Partial Gene Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique. Examples of polynucleotide reagents include the nucleic acid sequences of the invention or portions thereof, e.g., fragments derived from noncoding regions having a length of at least 20 or 30 bases.

The nucleic acid sequences described herein can further be used to provide polynucleotide reagents, e.g., labeled or labelable probes which can be used in, for example, an in situ hybridization technique, to identify a specific tissue, e.g., spleen tissue or liver tissue. This can be very useful in cases where a forensic pathologist is presented with a tissue of unknown origin. Panels of such probes can be used to identify tissue by species and/or by organ type.

Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining FAIL protein and/or nucleic acid expression as well as FAIL activity, in the context of a biological sample (e.g., blood, serum, cells, and tissue) to thereby determine whether an individual is afflicted with a disease or disorder, or is at risk of developing a disorder, associated with aberrant or unwanted FAIL expression or activity. The invention also provides for prognostic (or predictive) assays for determining whether an individual is at risk of developing a disorder associated with FAIL protein, nucleic acid expression or activity. For example, mutations in a FAIL gene can be assayed in a biological sample. Such assays can be used for prognostic or predictive purpose to thereby prophylactically treat an individual prior to the onset of a disorder characterized by or associated with FAIL protein and/or nucleic acid expression or activity.

As an alternative to making determinations based on the absolute expression level of selected genes, determinations may be based on the normalized expression levels of these genes. Expression levels are normalized by correcting the absolute expression level of a FAIL gene by comparing its expression to the expression of a gene that is not a FAIL gene, e.g., a housekeeping gene that is constitutively expressed. Suitable genes for normalization include housekeeping genes such as the actin gene. This normalization allows the comparison of the expression level in one sample, e.g., a patient sample, to another sample, e.g., a sample from an individual without a particular disease or disorder, or a sample from a healthy individual, or between samples from different sources.

Alternatively, the expression level can be provided as a relative expression level. To determine a relative expression level of a gene, the level of expression of the gene is determined for 10 or more samples of different cell isolates (e.g., immune cell isolates such as T cells), preferably 50 or more samples, prior to the determination of the expression level for the sample in question. The mean expression level of each of the genes assayed in the larger number of samples is determined and this is used as a baseline expression level for the gene(s) in question. The expression level of the gene determined for the test sample (absolute level of expression) is then divided by the mean expression value obtained for that gene. This provides a relative expression level and aids in identifying extreme cases of diseases and disorders such as immune disorders (e.g., inflammatory bowel disease (e.g., Crohn's disease and ulcerative colitis), autoimmune disorders (e.g., multiple sclerosis) inflammatory disorders (e.g., rheumatoid arthritis and asthma), and chronic obstructive pulmonary disorders).

Preferably, the samples used in the baseline determination will be from diseased or from non-diseased cells of the appropriate cell type or tissue. The choice of the cell source is dependent on the use of the relative expression level. Using expression found in normal tissues as a mean expression score aids in validating whether the FAIL gene assayed is specific (versus normal cells). Such a use is particularly important in identifying whether a FAIL gene can serve as a target gene. In addition, as more data is accumulated, the mean expression value can be revised, providing improved relative expression values based on accumulated data. Expression data from cells provides a means for grading the severity of the disease or disorder state.

Another aspect of the invention pertains to monitoring the influence of agents (e.g., drugs or compounds) on the expression or activity of FAIL in clinical trials. These and other agents are described in further detail in the following sections.

Diagnostic Assays

An exemplary method for detecting the presence or absence of a polypeptide or nucleic acid of the invention in a biological sample involves obtaining a biological sample from a test subject and contacting the biological sample with a compound or an agent capable of detecting a polypeptide or nucleic acid (e.g., mRNA, genomic DNA) of the invention such that the presence of a polypeptide or nucleic acid of the invention is detected in the biological sample. A preferred agent for detecting mRNA or genomic DNA encoding a polypeptide of the invention is a labeled nucleic acid probe capable of hybridizing to mRNA or genomic DNA encoding a polypeptide of the invention. The nucleic acid probe can be, for example, a full-length cDNA, such as the nucleic acid of SEQ ID NO:1, or a portion thereof, such as an oligonucleotide of at least 15, 30, 50, 100, 250 or 500 nucleotides in length and sufficient to specifically hybridize under stringent conditions to a mRNA or genomic DNA encoding a polypeptide of the invention. Other suitable probes for use in the diagnostic assays of the invention are described herein.

A preferred agent for detecting a polypeptide of the invention is an antibody capable of binding to a polypeptide of the invention, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect mRNA, protein, or genomic DNA in a biological sample in vitro as well as in vivo. For example, in vitro techniques for detection of mRNA include Northern hybridizations and in situ hybridizations. In vitro techniques for detection of a polypeptide of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide of the invention include introducing into a subject a labeled antibody directed against the polypeptide. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a polypeptide of the invention or mRNA or genomic DNA encoding a polypeptide of the invention, such that the presence of the polypeptide or mRNA or genomic DNA encoding the polypeptide is detected in the biological sample, and comparing the presence of the polypeptide or mRNA or genomic DNA encoding the polypeptide in the control sample with the presence of the polypeptide or mRNA or genomic DNA encoding the polypeptide in the test sample.

The invention also encompasses kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention as discussed, for example, in sections above relating to uses of the sequences of the invention.

For example, kits can be used to determine if a subject is suffering from or is at increased risk of disorders such as lung disorders (e.g., asthma, bronchitis, bronchiolitis, cystic fibrosis, sacrcoidosis, idiopathic pulmonary fibrosis, hypersensitivity pneumontis, pneumonia, emphysema, and lung cancer), liver disorders (e.g., jaundice, hepatic failure, hereditary hyperbiliruinemias, hepatic circulatory disorders (e.g., hepatic vein thrombosis and portal vein obstruction and thrombosis), hepatitis (e.g., chronic active hepatitis, acute viral hepatitis, and toxic and drug-induced hepatitis), cirrhosis (e.g., alcoholic cirrhosis, biliary cirrhosis, and hemochromatosis), and malignant tumor), bone marrow disorders, splenic disorders (e.g., splenic lymphoma, splenomegaly, and phagocytotic disorders, e.g., those inhibiting macrophage engulfment of bacteria and viruses in the bloodstream), and immune disorders such as inflammatory bowel disease (e.g., Crohn's disease and ulcerative colitis), autoimmune disorders (e.g., multiple sclerosis), inflammatory disorders (e.g., rheumatoid arthritis and asthma), and chronic obstructive pulmonary disorders, which are associated with aberrant FAIL expression. The kit, for example, can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (e.g., attached to a solid support) which binds to a polypeptide of the invention; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or (2) a pair of primers useful for amplifying a nucleic acid molecule encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

Prognostic Assays

The methods described herein can furthermore be utilized as diagnostic or prognostic assays to identify subjects having or at risk of developing a disease or disorder associated with aberrant expression or activity of a polypeptide of the invention. For example, the assays described herein, such as the preceding diagnostic assays or the following assays, can be utilized to identify a subject having or at risk of developing a disorder associated with aberrant expression or activity of a polypeptide of the invention, e.g., an immunologic disorder, or embryonic disorders. Alternatively, the prognostic assays can be utilized to identify a subject having or at risk for developing such a disease or disorder. Thus, the present invention provides a method in which a test sample is obtained from a subject and a polypeptide or nucleic acid (e.g., mRNA, genomic DNA) of the invention is detected, wherein the presence of the polypeptide or nucleic acid is diagnostic for a subject having or at risk of developing a disease or disorder associated with aberrant expression or activity of the polypeptide. As used herein, a "test sample" refers to a biological sample obtained from a subject of interest. For example, a test sample can be a biological fluid (e.g., serum), cell sample, or tissue.

The prognostic assays described herein, for example, can be used to identify a subject having or at risk of developing disorders such as disorders discussed, for example, in sections above relating to uses of the sequences of the invention. For example, such disorders can include lung disorders (e.g., asthma, bronchitis, bronchiolitis, cystic fibrosis, sarcoidosis, idiopathic pulmonary fibrosis, hypersensitivity pneumontis, pneumonia, emphysema, and lung cancer), liver disorders (e.g., jaundice, hepatic failure, hereditary hyperbiliruinemias, hepatic circulatory disorders (e.g., hepatic vein thrombosis and portal vein obstruction and thrombosis), hepatitis (e.g., chronic active hepatitis, acute viral hepatitis, and toxic and drug-induced hepatitis), cirrhosis (e.g., alcoholic cirrhosis, biliary cirrhosis, and hemochromatosis), and malignant tumor), bone marrow disorders, splenic disorders (e.g., splenic lymphoma, splenomegaly, and phagocytotic disorders, e.g., those inhibiting macrophage engulfment of bacteria and viruses in the bloodstream), and immune disorders such as inflammatory bowel disease (e.g., Crohn's disease and ulcerative colitis), autoimmune disorders (e.g., multiple sclerosis), inflammatory disorders (e.g., rheumatoid arthritis and asthma), and chronic obstructive pulmonary disorders, which are associated with aberrant FAIL expression.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a polypeptide of the invention. For example, such methods can be used to determine whether a subject can be effectively treated with a specific agent or class of agents (e.g., agents of a type which decrease activity of the polypeptide). Thus, the present invention provides methods for determining whether a subject can be effectively treated with an agent for a disorder associated with aberrant expression or activity of a polypeptide of the invention in which a test sample is obtained and the polypeptide or nucleic acid encoding the polypeptide is detected (e.g., wherein the presence of the polypeptide or nucleic acid is diagnostic for a subject that can be administered the agent to treat a disorder associated with aberrant expression or activity of the polypeptide).

The methods of the invention can also be used to detect genetic lesions or mutations in a gene of the invention, thereby determining if a subject with the lesioned gene is at risk for a disorder characterized by aberrant expression or activity of a polypeptide of the invention. In preferred embodiments, the methods include detecting, in a sample of cells from the subject, the presence or absence of a genetic lesion or mutation characterized by at least one of an alteration affecting the integrity of a gene encoding the polypeptide of the invention, or the mis-expression of the gene encoding the polypeptide of the invention. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) *Proc. Natl. Acad. Sci. USA* 91:360–364), the latter of which can be particularly useful for detecting point mutations in a gene (see, e.g., Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a selected gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotides probes (Cronin et al. (1996)

*Human Mutation* 7:244–255; Kozal et al. (1996) *Nature Medicine* 2:753–759). For example, genetic mutations can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the selected gene and detect mutations by comparing the sequence of the sample nucleic acids with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in a selected gene include methods in which protection from cleavage agents is used to detect mismatched bases in RNA/RNA or RNA/DNA heteroduplexes (Myers et al. (1985) *Science* 230:1242). In general, the technique of "mismatch cleavage" entails providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to basepair mismatches between the control and sample strands. RNA/DNA duplexes can be treated with RNase to digest mismatched regions, and DNA/DNA hybrids can be treated with S1 nuclease to digest mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a selected sequence, e.g., a wild-type sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in genes. For example, single strand conformation polymorphism (SSCP) may be used to detect differences in electrophoretic mobility between mutant and wild type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). Single-stranded DNA fragments of sample and control nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a 'GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe, nucleic acid or antibody reagent described herein, which may be conveniently used, e.g., in clinical settings to diagnose patients exhibiting symptoms or family history of a disease or illness involving a gene encoding a polypeptide of the invention. Furthermore, any cell type or tissue, e.g., chondrocytes, in which the polypeptide of the invention is expressed may be utilized in the prognostic assays described herein.

Pharmacogenomics

Agents or modulators which have a stimulatory or inhibitory effect on activity or expression of a polypeptide of the invention as identified by a screening assay described herein can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a polypeptide of the invention, expression of a nucleic acid of the invention, or mutation content of a gene of the invention in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a polypeptide of the invention, expression of a nucleic acid encoding the polypeptide, or mutation content of a gene encoding the polypeptide in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

Monitoring of Fail Modulator Effects

Monitoring the influence of agents (e.g., drugs, compounds) on the expression or activity of a polypeptide of the invention (e.g., the ability to modulate aberrant cell proliferation chemotaxis, and/or differentiation) can be applied in basic drug screening, preclinical studies, clinical trials and during therapeutic treatment regimens.

For example, the effectiveness of an agent, as determined by a screening assay as described herein, to increase gene expression, protein levels or protein activity, can be monitored in clinical trials of subjects exhibiting decreased gene expression, protein levels, or protein activity. Alternatively, the effectiveness of an agent, as determined by a screening assay, to decrease gene expression, protein levels or protein activity, can be monitored in clinical trials of subjects exhibiting increased gene expression, protein levels, or protein activity. In such clinical trials, expression or activity of a polypeptide of the invention and preferably, that of other polypeptides that have been implicated in, for example, a cellular proliferation disorder, can be used as a marker of the immune responsiveness of a particular cell.

For example, and not by way of limitation, genes, including those of the invention, that are modulated in cells by treatment with an agent (e.g., compound, drug or small molecule) which modulates activity or expression of a polypeptide of the invention (e.g., as identified in a screening assay described herein) can be identified. Thus, to study the effect of agents on cellular proliferation disorders, for example, in a clinical trial, cells can be isolated and RNA prepared and analyzed for the levels of expression of a gene of the invention and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of a gene of the invention or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of the polypeptide or nucleic acid of the invention in the preadministration sample; (iii) obtaining one or more post-administration samples from the subject; (iv) detecting the level the of the polypeptide or nucleic acid of the invention in the post-administration samples; (v) comparing the level of the polypeptide or nucleic acid of the invention in the pre-administration sample with the level of the polypeptide or nucleic acid of the invention in the post-administration sample or samples; and (vi) altering the administration of the agent to the subject accordingly. For example, increased administration of the agent may be desirable to increase the expression or activity of the polypeptide to higher levels than detected, i.e., to increase the effectiveness of the agent. Alternatively, decreased administration of the agent may be desirable to decrease expression or activity of the polypeptide to lower levels than detected, i.e., to decrease the effectiveness of the agent.

In yet another embodiment, a method of the invention includes a method for determining the therapeutic dosage of a FAIL modulator to be administered to an individual in need of treatment for a FAIL-related disorder, comprising: administering a dose of a FAIL modulator to a non-human animal model of a FAIL-related disorder, and assaying FAIL function and/or assaying a symptom of the FAIL-related disorder in the animal, so that if FAIL function and/or symptom in the animal is modulated in a manner that more closely resembles a corresponding animal not exhibiting the FAIL disorder, a therapeutic dosage of the FAIL modulator is determined, e.g., by extrapolating to the corresponding dosage in a human.

Methods of Treatment

The present invention provides for both prophylactic and therapeutic methods of treating a subject at risk of (or susceptible to) a disorder or having a disorder associated with aberrant expression or activity of a polypeptide of the invention, as discussed, for example, in sections above relating to uses of the sequences of the invention. For example, disorders characterized by aberrant expression or activity of the polypeptides of the invention include lung disorders (e.g., asthma, bronchitis, bronchiolitis, cystic fibrosis, sacrcoidosis, idiopathic pulmonary fibrosis, hypersensitivity pneumontis, pneumonia, emphysema, and lung cancer), liver disorders (e.g., jaundice, hepatic failure, hereditary hyperbiliruinemias, hepatic circulatory disorders (e.g., hepatic vein thrombosis and portal vein obstruction and thrombosis), hepatitis (e.g., chronic active hepatitis, acute viral hepatitis, and toxic and drug-induced hepatitis), cirrhosis (e.g., alcoholic cirrhosis, biliary cirrhosis, and hemochromatosis), and malignant tumor), bone marrow disorders, splenic disorders (e.g., splenic lymphoma, splenomegaly, and phagocytotic disorders, e.g., those inhibiting macrophage engulfment of bacteria and viruses in the bloodstream), and immune disorders such as inflammatory bowel disease (e.g., Crohn's disease and ulcerative colitis), autoimmune disorders (e.g., multiple sclerosis), inflammatory disorders (e.g., rheumatoid arthritis and asthma), and chronic obstructive pulmonary disorders. The nucleic acids, polypeptides, and modulators thereof of the invention can be used to treat lung disorders (e.g., asthma, bronchitis, bronchiolitis, cystic fibrosis, sacrcoidosis, idiopathic pulmonary fibrosis, hypersensitivity pneumontis, pneumonia, emphysema, and lung cancer), liver disorders (e.g., jaundice, hepatic failure, hereditary hyperbiliruinemias, hepatic circulatory disorders (e.g., hepatic vein thrombosis and portal vein obstruction and thrombosis), hepatitis (e.g., chronic active hepatitis, acute viral hepatitis, and toxic and drug-induced hepatitis), cirrhosis (e.g., alcoholic cirrhosis, biliary cirrhosis, and hemochromatosis), and malignant tumor), bone marrow disorders, splenic disorders (e.g., splenic lymphoma, splenomegaly, and phagocytotic disorders, e.g., those inhibiting macrophage engulfment of bacteria and viruses in the bloodstream), and immune disorders such as inflammatory bowel disease (e.g., Crohn's disease and ulcerative colitis), autoimmune disorders (e.g., multiple sclerosis), inflammatory disorders (e.g., rheumatoid arthritis and asthma), and chronic obstructive pulmonary disorders. In various embodiments, such modulation can be achieved via administration of FAIL modulators prior to, during, or subsequent to a given procedure (e.g., a transfusion). In a preferred embodiment, such administration can be utilized to prevent immune disorders such as inflammatory bowel disease (e.g., Crohn's disease and ulcerative colitis), autoimmune disorders (e.g., multiple sclerosis) inflammatory disorders (e.g., rheumatoid arthritis and asthma), and chronic obstructive pulmonary disorders, as well as other disorders described herein.

Prophylactic Methods

In one aspect, the invention provides a method for preventing in a subject, a disease or condition associated with an aberrant expression or activity of a polypeptide of the invention, by administering to the subject an agent which modulates expression or at least one activity of the polypeptide. Subjects at risk for a disease which is caused or contributed to by aberrant expression or activity of a polypeptide of the invention can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject. For example, an antagonist of a FAIL protein may be used to treat an immune disorder, e.g., inflammatory bowel disease, inflammatory disorders (e.g., asthma and rheumatoid arthritis), autoimmune disorders (e.g., multiple sclerosis), and chronic obstructive pulmonary disease. The appropriate agent can be determined based on screening assays described herein.

Therapeutic Methods

Another aspect of the invention pertains to methods of modulating expression or activity of a polypeptide of the invention for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, or a small molecule such as a peptide, a peptidomimetic, or other small organic molecule. In one embodiment, the agent stimulates one or more of the biological activities of the polypeptide. Examples of such stimulatory agents include the active polypeptide of the invention and a nucleic acid molecule encoding the polypeptide of the invention that has been introduced into the cell. In another embodiment, the agent inhibits one or more of the biological activities of the polypeptide of the invention. Examples of such inhibitory agents include antisense nucleic acid molecules and antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a polypeptide of the invention. In one embodiment, the method involves administering an agent (e.g., an agent identified by a screening assay described herein), or combination of agents that modulates (e.g., upregulates or downregulates) expression or activity. In another embodiment, the method involves administering a polypeptide of the invention or a nucleic acid molecule of the invention as therapy to compensate for reduced or aberrant expression or activity of the polypeptide.

Stimulation of activity is desirable in situations in which activity or expression is abnormally low or downregulated and/or in which increased activity is likely to have a beneficial effect. Conversely, inhibition of activity is desirable in situations in which activity or expression is abnormally high or upregulated and/or in which decreased activity is likely to have a beneficial effect.

Deposit of Clones

A clone containing a cDNA molecule encoding human FAIL was deposited with the American Type Culture Collection, 10801 University Boulevard, Manassas, Va., 20110-2209, on Jul. 21, 2000 as PTA-2266.

Equivalents

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

What is claimed is:

1. An isolated nucleic acid molecule or its entire complement, wherein the nucleic acid molecule
encodes a polypeptide comprising an amino acid sequence of at least 95% identical to the amino acid sequence of SEQ ID NO:3, SEQ ID NO:5, or the amino acid sequence encoded by the cDNA insert of the plasmid deposited with the ATCC® as patent deposit Number PTA-2266;
wherein the polypeptide comprises an amino acid sequence selected from the group consisting of:
   a) amino acid residues 27–80 of SEQ ID NO:3;
   b) amino acid residues 120–177 of SEQ ID NO:3; and
   c) amino acid residues 216–273 of SEQ ID NO:3;
and wherein the polypeptide binds to the Fc portion of the antibody.

2. The nucleic acid molecule of claim 1 further comprising vector nucleic acid sequences.

3. The nucleic acid molecule of claim 1 further comprising nucleic acid sequences encoding a heterologous polypeptide.

4. A host cell in culture wherein the host cell is genetically engineered to express the nucleic acid molecule of claim 1.

5. The host cell of claim 4 which is a mammalian host cell.

6. A method for producing a polypeptide
comprising an amino acid sequence of at least 95% identical to the amino acid sequence SEQ ID NO:3, SEQ ID NO;5, or the amino acid sequence encoded by the cDNA insert of the plasmid deposited with the ATCC® as patent deposit Number PTA-2266;
wherein the polypeptide comprises an amino acid sequence selected from the group consisting of:
   a) amino acid residues 27–80 of SEQ ID NO:3;
   b) amino acid residues 120–177 of SEQ ID NO:3; and
   c) amino acid residues 216–273 of SEQ ID NO:3;
and wherein the polypeptide binds to the Fc portion of the antibody, comprising culturing the host cell of claim 4 under condition in which the nucleic acid molecule is expressed.

7. The nucleic acid molecule of claim 1, wherein the nucleic acid molecule encodes a polypeptide comprising the Ig domain of FALL (amino acids 27–80 of SEQ ID NO:3).

8. The nucleic acid molecule of claim 1, wherein the nucleic acid molecule encodes a polypeptide comprising an Ig-like domain of FAIL (amino acids 120–177 or 216–273 of SEQ ID NO:3).

9. The nucleic acid molecule of claim 1, wherein the nucleic acid molecule encodes a polypeptide comprising the extracellular domain of FAIL (amino acids 28–305 of SEQ ID NO:3).

10. The nucleic acid molecule of claim 2, wherein the vector sequences regulate expression of the nucleic acid molecule.

11. A host cell in culture wherein the host cell comprises the vector of claim 10.

12. The host cell of claim 11 which is a mammalian host cell.

13. A method of producing a polypeptide comprising: culturing the host cell of claim 12 under conditions in which the nucleic arid molecule is expressed to produce said polypeptide.

14. An isolated nucleic acid molecule comprising a nucleic acid sequence selected from the group consisting of:
   (a) the nucleotide sequence of SEQ ID NO:1, or an entire complement thereof:
   (b) the nucleotide sequence of SEQ II) NO:2, or an entire complement thereof; and
   (c) the nucleotide sequence of the cDNA insert of the plasmid deposited with the ATCC® as patent deposit Number PTA-2266, or an entire complement thereof.

15. An isolated nucleic acid molecule comprising a nucleic acid sequence selected from the group consisting of:
   (a) a nucleotide sequence which encodes a polypeptide comprising the amino acid sequence of SEQ ID NO:3;
   (b) a nucleotide sequence which encodes a polypeptide comprising the amino acid sequence of SEQ ID NO:5; and
   (c) a nucleotide sequence which encodes a polypeptide comprising the amino acid sequence encoded by the cDNA insert of the plasmid deposited with the ATCC as patent deposit Number PTA-2266.

16. A host cell in culture wherein the host cell is genetically engineered to express the nucleic acid molecule of claim 15.

17. A method for producing a polypeptide selected from the group consisting of:
   a) a polypeptide comprising the amino acid sequence of SEQ ID NO:3;
   b) a polypeptide comprising the amino acid sequence of SEQ ID NO:5; and
   c) a polypeptide comprising the amino acid sequence encoded by the cDNA insert of the plasmid deposited with the ATCC® as patent deposit Number PTA-2266, comprising culturing the host cell of claim 16 under conditions in which the nucleic acid molecule is expressed.

18. The nucleic acid molecule of claim 15 further comprising vector nucleic acid sequences.

19. The nucleic acid molecule of claim 15 further comprising nucleic acid sequences encoding a heterologous polypeptide.

20. The nucleic acid molecule of claim 1, wherein the nucleic acid molecule is selected from the group consisting of:
   (a) a nucleic acid which comprises a nucleic acid sequence of SEQ ID NO:22, SEQ ID NO:23, SEQ ID NO:24, SEQ ID NO:25, SEQ ID NO:26, SEQ ID NO:27, SEQ ID NO:28, or SEQ ID NO:29; and
   (b) a nucleic acid which encodes SEQ ID NO:30, SEQ ID NO:31, SEQ ID NO:32 or SEQ ID NO:33.

* * * * *